United States Patent
Wuts et al.

(10) Patent No.: US 8,906,848 B2
(45) Date of Patent: Dec. 9, 2014

(54) AUREOBASIDIN DERIVATIVES AND METHODS OF SYNTHESIS

(75) Inventors: Peter Wuts, Kalamazoo, MI (US); Ake P. Elhammer, Kalamazoo, MI (US)

(73) Assignee: AureoGen Biosciences, inc., Kalamazoo, MI (US)

( * ) Notice: Subject to any disclaimer, the term of this patent is extended or adjusted under 35 U.S.C. 154(b) by 0 days.

(21) Appl. No.: 14/006,493

(22) PCT Filed: Mar. 23, 2012

(86) PCT No.: PCT/US2012/030269
§ 371 (c)(1),
(2), (4) Date: Oct. 9, 2013

(87) PCT Pub. No.: WO2012/134989
PCT Pub. Date: Oct. 4, 2012

(65) Prior Publication Data
US 2014/0024578 A1    Jan. 23, 2014

Related U.S. Application Data

(60) Provisional application No. 61/470,750, filed on Apr. 1, 2011, provisional application No. 61/535,018, filed on Sep. 15, 2011.

(51) Int. Cl.
*A61K 38/12* (2006.01)
*C07K 11/02* (2006.01)
*C07K 1/113* (2006.01)
*A61K 38/00* (2006.01)

(52) U.S. Cl.
CPC ............... *C07K 1/113* (2013.01); *C07K 11/02* (2013.01); *A61K 38/00* (2013.01)
USPC ............ 514/3.6; 514/3.3; 514/21.6; 530/317; 530/323; 530/328; 530/345

(58) Field of Classification Search
None
See application file for complete search history.

(56) References Cited

FOREIGN PATENT DOCUMENTS

| EP | 0510271 A1 | * | 4/1991 |
| EP | 0510271 | | 10/1992 |
| EP | 0581429 | | 2/1994 |
| EP | 0687686 | | 12/1995 |

OTHER PUBLICATIONS

Ikai, Katsushige, et al., "Structures of Aureobasidins B to R", The Journal of Antibiotics, Japan Antibiotics Research Association, vol. 44, No. 11, Nov. 1, 1991, pp. 1187-1198.
International Search Report for PCT/US2012/030269 dated Jul. 6, 2012.
Kurome, Toru, et al., "Structure-Activity Relationship of Antifungal Aureobasidin A, Inhibitor of Sphingolipid Biosynthesis: Synthesis of New Active Aureobasidins against *Aspergillus fumigatus*", Peptide Science, vol. 36, Dec. 31, 1999, pp. 197-200.
Meyer, Falco-Magnus, et al., "Functionalization of Aromatic Amino Acids via Direct C-H Activation: Generation of Versatile Building Blocks for Accessing Novel Peptide Space", Organic Letters, vol. 12, No. 17, Sep. 3, 2010, pp. 3870-3873.
Tiberghien, Françoise, et al. "Aureobasidins: Structure-Activity Relationships for the Inhibition of the Human MDR1 P-Glycoprotein ABC-Transporter", Journal of Medicinal Chemistry, vol. 43, No. 13, 200-06-01, pp. 2547-2556.

\* cited by examiner

*Primary Examiner* — James H Alstrum Acevedo
*Assistant Examiner* — Fred Reynolds
(74) *Attorney, Agent, or Firm* — Honigman Miller Schwartz & Cohn LLP; Andrew N. Weber; Jonathan P. O'Brien

(57) ABSTRACT

In general, the invention relates to methods of synthesizing AbA derivatives that are useful for treating infection and amenable to further chemical elaboration. These novel methods are scalable for industrial production and employ safer, simpler, and more efficient process conditions. Furthermore, the invention also provides novel compounds and intermediates useful for implementing the methods described herein and/or for the treatment of infection.

30 Claims, 5 Drawing Sheets

AUREOBASIDIN DERIVATIVES AND METHODS OF SYNTHESIS

CROSS-REFERENCE TO PRIOR APPLICATIONS

This application claims the benefit of PCT Application No. PCT/US2012/030269, filed Mar. 23, 2013, which claims priority to U.S. Provisional Application No. 61/470,750, filed Apr. 1, 2011, and U.S. Provisional Application No. 61/535,018, filed Sep. 15, 2011. Each of these references is hereby incorporated by reference in its entirety.

FIELD OF THE INVENTION

The present invention provides novel methods for synthesizing broad spectrum antibiotic compounds, e.g., Aureobasidin A derivatives, that are useful for preventing and/or treating infections.

BACKGROUND

As the population of cancer, transplantation, abdominal surgery, and other immunocompromised patients continues to grow, there is a concomitant increase in the number of patients needing treatment for systemic fungal infections. Traditionally, systemic mycoses antibiotics are dominated by just three classes of drugs, polyenes, most notably Amphotericin B and Nystatin; azoles, such as Flucanazole, Itraconazole, Ketoconazole, and Voriconazole; and echinocandins, such as Caspofungin, Micafungin, and Anidulafungin. Each of these drug classes possess significant limitations in terms of efficacy, toxicity, drug-drug interactions, and the generation of resistant organisms (e.g. Barrett, 2002; Fishman, 2002; Girmenia and Martino, 2003; Gupta and Thomas, 2003; Park et al., 2005; Pavie et al., 2005; Balashov et al., 2006; Perlin et al., 2007; Choi et al., 2008). Consequently, there is an urgent need for new drugs with novel modes of action to treat of systemic mycoses.

The *Aureobasidium pullulans* strain BP-1938 produces a 9-amino acid cyclic peptide, referred to as Aureobasidin A ("AbA"). This compound is a potent, fungicidal drug that is very well tolerated in animals and humans (Takesako et al., 1993). AbA also has a unique mode of action that targets inositol phosphorylceramide ("IPC") synthase; an enzyme in the fungal sphingolipid biosynthesis pathway. Attempts to develop spontaneous resistance mutants to AbA has, to date, been unsuccessful, suggesting that resistance development in clinical settings with this compound will be very slow. Resistance mutants can be generated by chemical mutagenesis; however, the viability of the resulting organism is highly compromised. (Heidler et al., 1995; Hashida-Okado et al., 1996). Unfortunately, native AbA does not have a perfect target spectrum: it is very efficacious against virtually all *Candida* species, including *C. albicans*. It is also efficacious against most *Cryptococcus* species, including *C. neoformans*. However, it shows little activity towards most *Aspergilli*, and most notably *A. fumigatus*. (Takesako et al., (1993) *J. Antibiot*. 46, 1414-1420). Since *Candida* and *Aspergillus* are the two most common human pathogens and broad-spectrum antibiotics are preferred in the clinic, AbA's lack of efficacy against aspergilli has hampered its development into a marketed drug (Takesako et al., 1993). The reason for *A. fumigatus'* resistance to AbA is not that the target enzyme, inositol phosphorylceramide (IPC) synthase in *A. fumigatus* is resistant to the compound, but rather that this organism has one or more pumps capable of efficiently clearing the drug (Ogawa et al., 1998; Zhong et al., 2000). Thus, the development of AbA derivative(s) capable of avoiding or blocking the *A. fumigatus* pumps would greatly enhance the development potential and marketability of the compound.

A small number of AbA derivatives have been prepared by synthetic chemistry (reviewed in Kurome and Takesako, 2000) and evaluation of these compounds has demonstrated that AbA's pharmacological properties can be altered significantly by modifying and/or exchanging amino acids in the sequence. Most importantly, AbA derivatives have been generated that appear to have similar antifungal activity against *A. fumigatus* and *C. albicans* (Kurome and Takesako, 2000). Specifically, substitution of the N-methyl-L-phenylalanine residue at position 4 with a N-methyl-D-alanine or a sarcosine residue results in a compound with significant activity against *A. fumigatus*; and combining this substitution with substitution of the L-phenylalanine residue at position 3 with derivatized L-tyrosine, phenylalanine or alanine residues, results in compounds with *A. fumigatus* minimum inhibitory concentrations (MICs) in the single digit microgram/ml range. Importantly, while gaining considerable activity against *A. fumigatus*, these compounds retain their activity against *C. albicans* and *Cryptococcus neoformans*. Nonetheless, the synthetic chemistry approach that was used for the synthesis of these compounds was very complex. The entire synthesis process included 21 steps and the overall yield was less than 1%. In addition, the one or more of the 21 steps constitutes a high risk procedure that is not amenable for industrial production. During the late 1990s and early 2000s, Pharmacia, and later Pfizer, Inc., attempted to improve Takara's 21 step synthesis. However, these attempts were unsuccessful and Pfizer abandoned the project in 2005.

SUMMARY OF THE INVENTION

In general, the invention relates to AbA derivatives, methods of synthesizing AbA derivatives, and intermediates that are useful for treating infection and amenable to further chemical elaboration. The novel methods presented herein are scalable for industrial production and employ safer, simpler, and more efficient process conditions.

In one aspect, the invention provides a method of generating a compound of Formula I

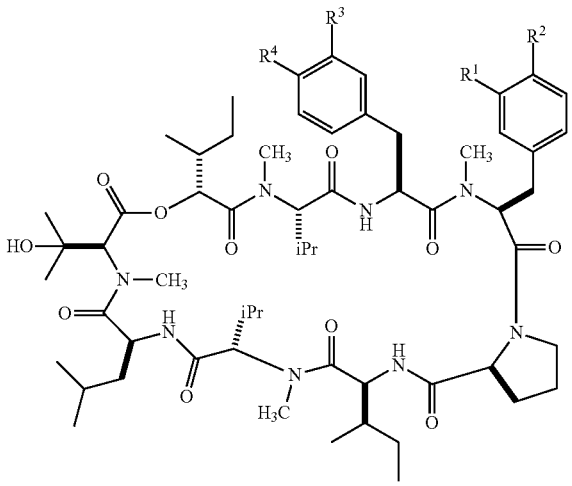

wherein one of $R^1$, $R^2$, $R^3$, or $R^4$ is —X, and the remainder are —H, wherein X is a halogen; comprising reacting a compound of Formula V with a halogenating reagent in the presence of a first solvent to form the compound of Formula I

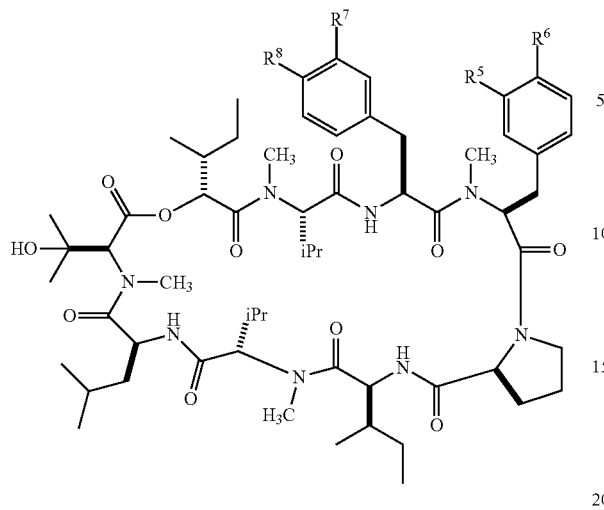

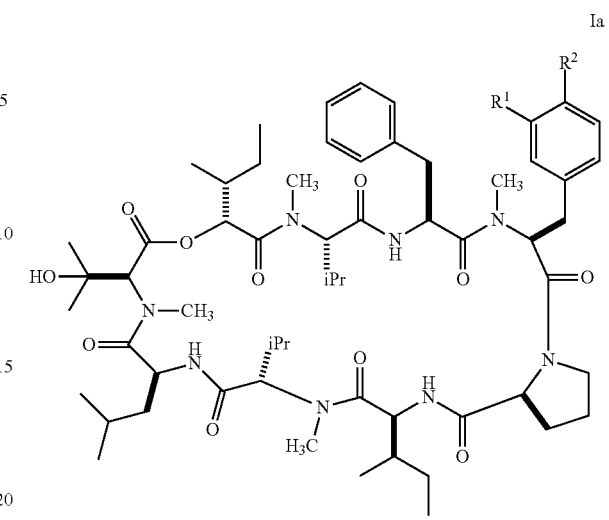

wherein one of R⁵, R⁶, R⁷, or R⁸ is

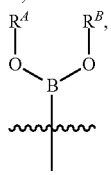

and the remainder are —H; and each of $R^A$ and $R^B$ are independently —$C_{1-4}$ alkyl, —$C_{3-6}$ cycloalkyl; or $R^A$ and $R^B$ together with the oxygen atoms to which they are attached form a 5-6 membered ring optionally substituted with 1-4 of —$C_{1-3}$ alkyl, —$C_{1-3}$ alkoxycarbonyl, —$C_{1-3}$ alkylaminocarbonyl, or any combination thereof; or $R^A$ and $R^B$ together with the oxygen atoms to which they are attached form a 7-10 membered bicyclic or tricyclic ring optionally substituted with 1-4 of —$C_{1-3}$ alkyl, —$C_{1-3}$ alkoxycarbonyl, —$C_{1-3}$ alkylaminocarbonyl, or any combination thereof.

In some implementations, the method further comprises reacting a compound of Formula 2

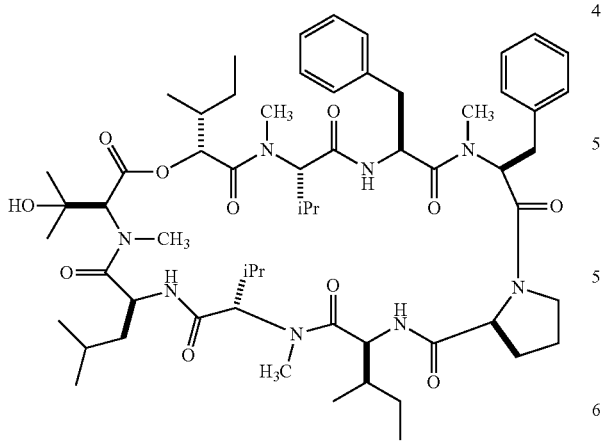

with a borylating reagent in the presence of a catalyst and a second solvent to generate a compound of Formula V.

In other implementations, the compound of Formula I is a compound of Formula Ia wherein one of R¹ or R² is —X, and the remainder is —H.

In some implementations, —X is selected from —Cl, —Br, or —I.

In other implementations, the halogenating reagent comprises copper(II)halide. For instance, the halogenating reagent comprises copper(II)iodide, copper(II)bromide, or copper(II)chloride.

In some implementations, the compound of Formula V is a compound of Formula Va

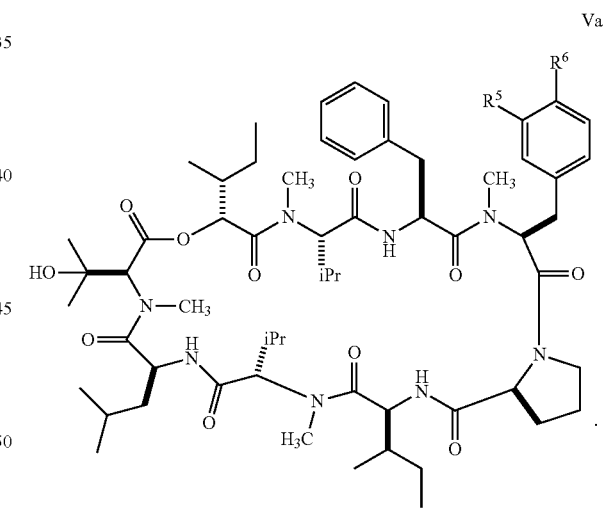

In other implementations, one of R⁵ or R⁶ is

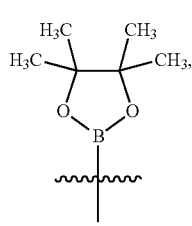

and the remainder is —H.

In some implementations, the first solvent comprises a polar solvent. For example, the polar solvent comprises an alcohol. In some instances, the alcohol comprises methanol, ethanol, iso-propanol, tert-butanol, or any combination thereof. In other instances, the first solvent further comprises water.

In some implementations, the reaction is conducted under heat (e.g., from about 35° C. to about 100° C. or from about 40° C. to about 80° C.).

In some implementations, the borylating reagent comprises 4,4,5,5-tetramethyl-1,3,2-dioxaborolane, catecholborane, bis(neopentyl glycolato)diboron, bis(pinacolato)diboron, bis(hexylene glycolato)diboron, bis(catecholato) diboron, bis[(+)-pinanediolato]diboron, bis[(−)-pinanediolato]diboron, bis(diethyl-D-tartrate glycolato) diboron, bis(diethyl-L-tartrate glycolato)diboron, bis (diisopropyl-D-tartrate glycolato)diboron, bis(diisopropyl-L-tartrateglycolato)diboron, bis(N,N,N',N'-tetramethyl-D-tartaramideglycolato)diboron, bis(N,N,N',N'-tetramethyl-L-tartaramideglycolato)diboron, or any combination thereof. For example, the borylating reagent comprises bis(pinacolato)diboron.

In some implementations, the catalyst is a transition metal catalyst. For example, the transition metal catalyst comprises Ir, Re, Rh, Pd, Pt, Ni, or any combination thereof. In other examples, the transition metal catalyst comprises Ir. For instance, the transition metal catalyst comprises di-μ-methoxybis(1,5-cyclooctadiene)diiridium(I), bis(1,5-cyclooctadiene)diiridium(I)dichloride, or any combination thereof.

In some implementations, the second solvent comprises an aprotic nonpolar solvent. For example, the aprotic nonpolar solvent comprises pentane, cyclopentane, hexane, cyclohexane, heptane, diethyl ether, or any combination thereof. In other examples, the second solvent further comprises MTBE. In some implementations, the method further comprises sparging the second solvent with an inert gas. And, in some examples, the inert gas comprises argon, nitrogen, xenon, or any combination thereof.

Another aspect of the present invention provides a method of generating a compound of Formula Ia

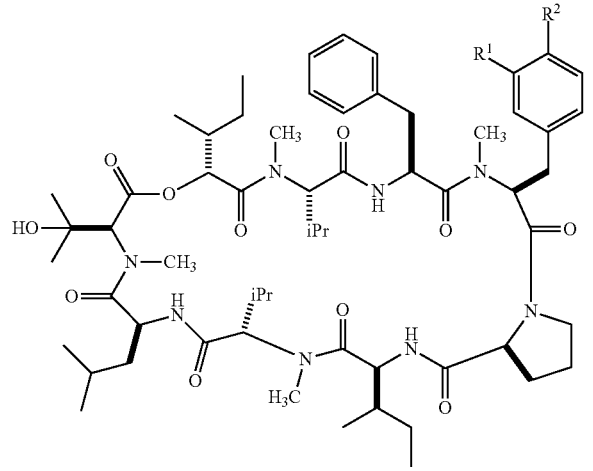

wherein one of $R^1$ or $R^2$ is —Br or —I, and the remainder is —H, comprising reacting a compound of Formula Va with a brominating reagent or iodinating reagent in the presence of a first solvent to form a compound of Formula Ia

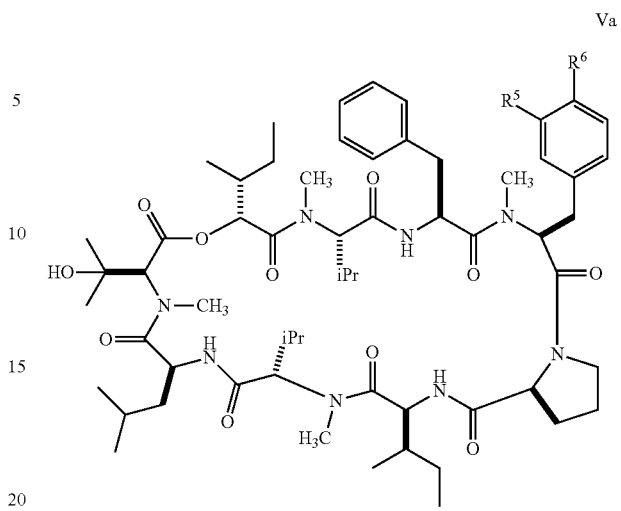

wherein one of $R^5$ or $R^6$ is

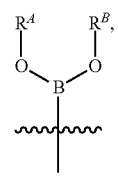

and the remainder is —H; and each of $R^A$ and $R^B$ are independently —$C_{1-4}$ alkyl, —$C_{3-6}$ cycloalkyl; or $R^A$ and $R^B$ together with the oxygen atoms to which they are attached form a 5-6 membered ring optionally substituted with 1-4 of —$C_{1-3}$ alkyl, —$C_{1-3}$ alkoxycarbonyl, —$C_{1-3}$ alkylaminocarbonyl, or any combination thereof; or $R^A$ and $R^B$ together with the oxygen atoms to which they are attached form a 7-10 membered bicyclic or tricyclic ring optionally substituted with 1-4 of —$C_{1-3}$ alkyl, —$C_{1-3}$ alkoxycarbonyl, —$C_{1-3}$ alkylaminocarbonyl, or any combination thereof.

In some implementations, the method further comprises reacting a compound of Formula 2

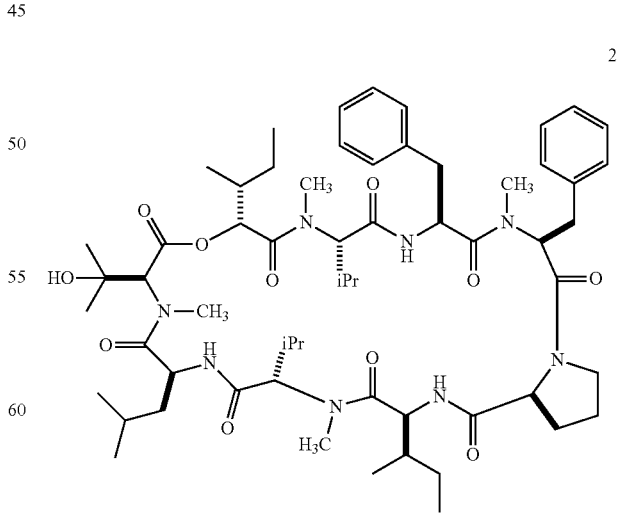

with a borylating reagent in the presence of a catalyst and a second solvent to generate a compound of Formula Va.

In some implementations, the compound of Formula Ia is

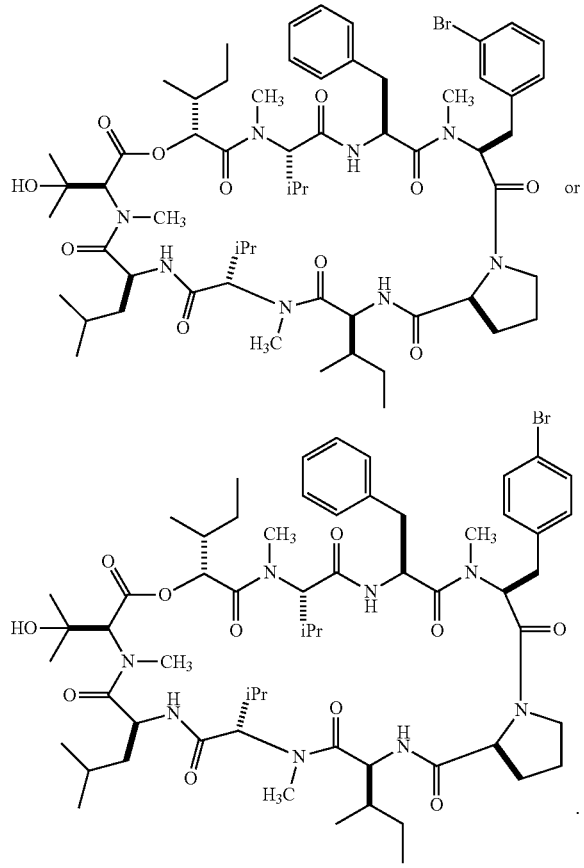

In some implementations, the brominating reagent comprises copper(II)bromide.

In some implementations, the compound of Formula Ia is

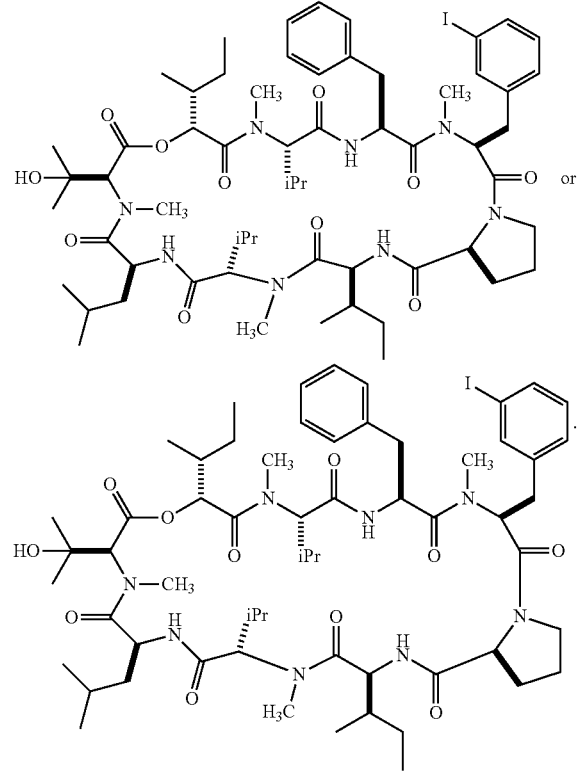

In some implementations, the iodinating reagent comprises copper(II)iodide.

In other implementations, one of $R^5$ or $R^6$ is

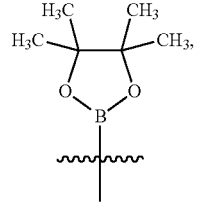

and the remainder is —H.

In some implementations, the first solvent comprises a polar solvent. For example, the polar solvent comprises an alcohol. In some instances, the alcohol comprises methanol, ethanol, iso-propanol, tert-butanol, or any combination thereof. In other instances, the first solvent further comprises water.

In some implementations, the reaction is conducted under heat (e.g., from about 35° C. to about 100° C. or from about 40° C. to about 80° C.).

In other implementations, the reaction is conducted at room temperature.

In some implementations, the borylating reagent comprises bis(pinacolato)diboron, bis(neopentylglycolato)diboron, 1,3,2-dioxaborolane, 4,5-dimethyl-1,3,2-dioxaborolane, bis(N,N,N',N'-tetramethyl-L-tartaramide glycolato)diboron, bis(diethyl-D-tartrate glycolato)diboron, bis(diethyl-L-tartrate glycolato)diboron, bis(diisopropyl-D-tartrate glycolato) diboron, bis[(+)-pinanediolato]diboron, or any combination thereof. For example, the borylating reagent comprises bis (pinacolato)diboron.

In some implementations, the catalyst is a transition metal catalyst. For example, the transition metal catalyst comprises Ir, Re, Rh, Pd, Pt, Ni, or any combination thereof. In other examples, the transition metal catalyst comprises Ir. For instance, the transition metal catalyst comprises di-β-methoxybis(1,5-cyclooctadiene)diiridium(I), bis(1,5-cyclooctadiene)diiridium(I)dichloride, or any combination thereof.

In some implementations, the second solvent comprises an aprotic nonpolar solvent. For example, the aprotic nonpolar solvent comprises pentane, cyclopentane, hexane, cyclohexane, heptane, diethyl ether, or any combination thereof. In other examples, the second solvent further comprises MTBE. In some implementations, the method further comprises sparging the second solvent with an inert gas. And, in some examples, the inert gas comprises argon, nitrogen, xenon, or any combination thereof.

Another aspect of the present invention provides a method of generating a compound of Formula II

II

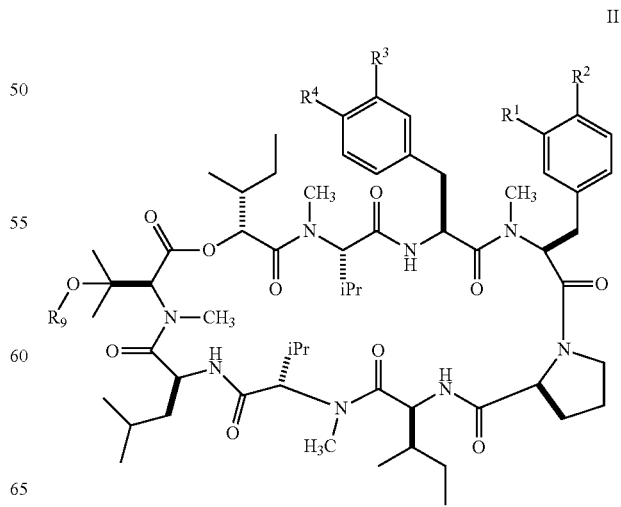

wherein one of R¹, R², R³, or R⁴ is —X, and the remainder are —H, wherein X is a halogen, and R⁹ is —Si(R¹⁰)₃, wherein each R¹⁰ is independently selected from an unsubstituted linear or branched $C_{1-6}$ alkyl; comprising reacting a compound of Formula I with Si(R¹⁰)₃X¹, wherein X¹ is a halogen, —OTf, —OTs, or —OMs, in the presence of a first solvent and a base to form a compound of Formula II

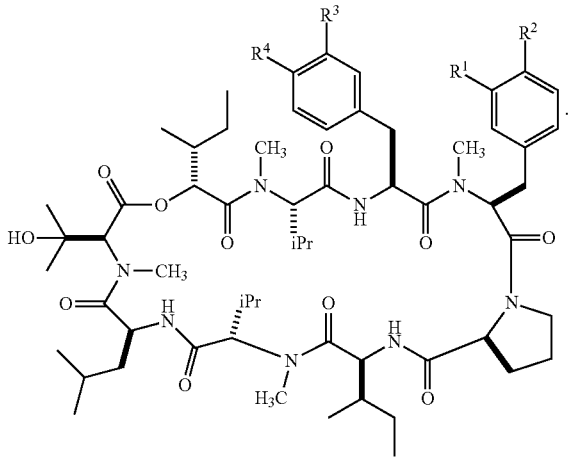

I

In some implementations, R⁹, is —Si(R¹⁰)₃, and each R¹⁰ is independently selected from methyl, ethyl, propyl, isopropyl, butyl, sec-butyl, or tert-butyl.

In some implementations, the first solvent comprises a polar solvent. For example, the polar solvent comprises dimethylformamide, dichloromethane, tetrahydrofuran, ethyl acetate, acetone, acetonitrile, dimethylsulfoxide, or any combination thereof.

In some implementations, the base comprises a tertiary amine base. For example, the tertiary amine base comprises imidazole, trimethylamine, triethylamine, N,N-dimethylpiperizine, N-methylpiperidine, N-methylpyrrolidine, or any combination thereof.

In some implementations, the method further comprises reacting a compound of Formula V with a halogenating reagent in the presence of a second solvent to form a compound of Formula I

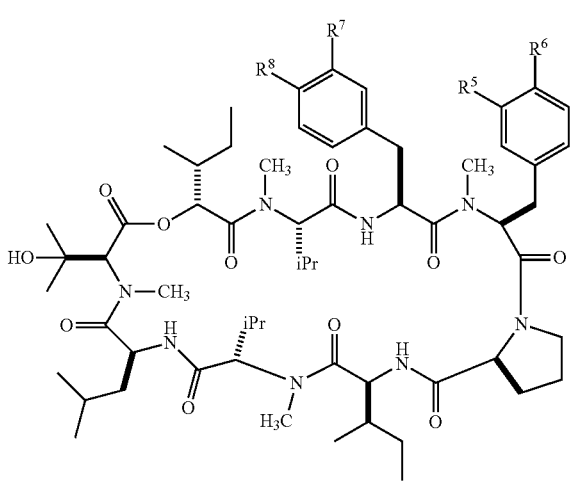

V wherein one of R⁵, R⁶, R⁷, or R⁸ is

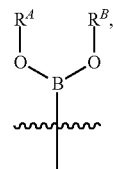

and the remainder are —H; and each of $R^A$ and $R^B$ are independently —$C_{1-4}$ alkyl, —$C_{3-6}$ cycloalkyl; or $R^A$ and $R^B$ together with the oxygen atoms to which they are attached form a 5-6 membered ring optionally substituted with 1-4 of —$C_{1-3}$ alkyl, —$C_{1-3}$ alkoxycarbonyl, —$C_{1-3}$ alkylaminocarbonyl, or any combination thereof; or $R^A$ and $R^B$ together with the oxygen atoms to which they are attached form a 7-10 membered bicyclic or tricyclic ring optionally substituted with 1-4 of —$C_{1-3}$ alkyl, —$C_{1-3}$ alkoxycarbonyl, —$C_{1-3}$ alkylaminocarbonyl, or any combination thereof.

In other implementations, the method further comprises reacting a compound of Formula 2

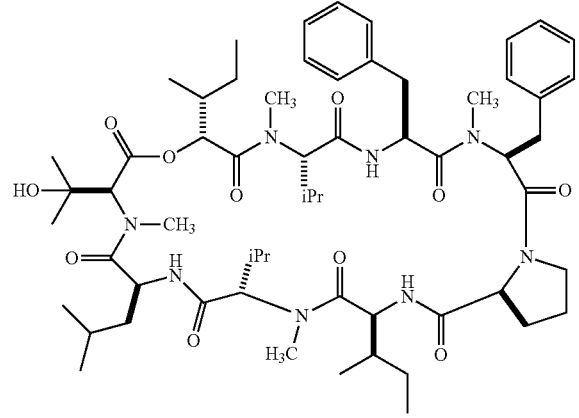

2 with a borylating reagent in the presence of a catalyst and a third solvent to generate a compound of Formula V.

In some implementations, the compound of Formula I is a compound of Formula Ia

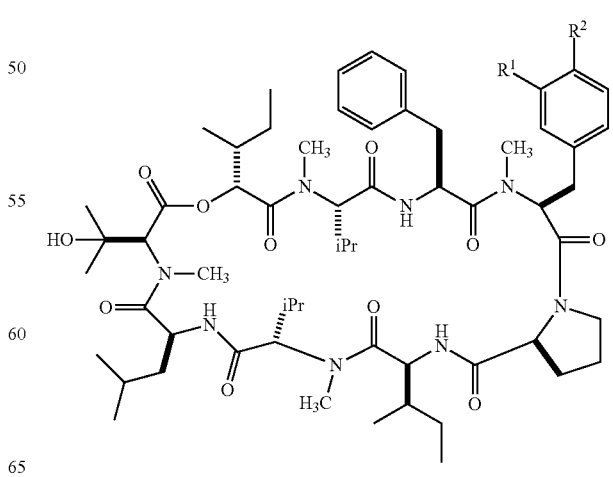

Ia wherein one of R¹ or R² is —X, and the remainder is —H.

In some implementations, —X is selected from —Cl, —Br, or —I.

In some implementations, the halogenating reagent comprises copper(II)halide. For example, the halogenating reagent comprises copper(II)bromide, copper(II)iodide, or copper(II)chloride.

In some implementations, the compound of Formula V is a compound of Formula Va

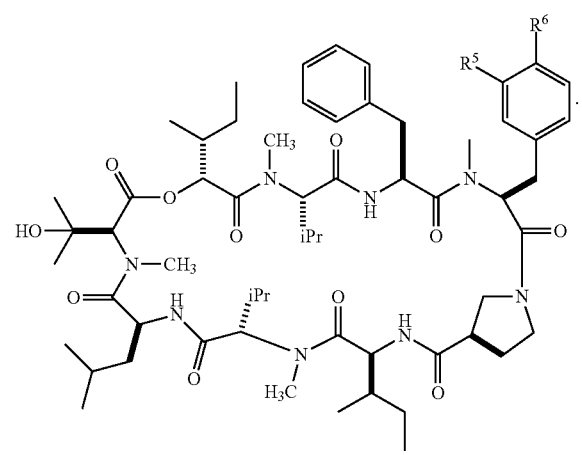

In some implementations, one of $R^5$ or $R^6$ is

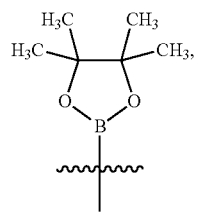

and the remainder is —H.

In some implementations, the second solvent comprises a polar solvent. For example, the polar solvent comprises an alcohol. In other examples, the alcohol comprises methanol, ethanol, iso-propanol, tert-butanol, or any combination thereof. And, in some examples, the first solvent further comprises water.

In some implementations, the reaction is conducted at room temperature.

In some implementations, the borylating reagent comprises 4,4,5,5-tetramethyl-1,3,2-dioxaborolane, catecholborane, bis(neopentyl glycolato)diboron, bis(pinacolato)diboron, bis(hexylene glycolato)diboron, bis(catecholato) diboron, bis[(+)-pinanediolato]diboron, bis[(−)-pinanediolato]diboron, bis(diethyl-D-tartrate glycolato) diboron, bis(diethyl-L-tartrate glycolato)diboron, bis (diisopropyl-D-tartrate glycolato)diboron, bis(diisopropyl-L-tartrateglycolato)diboron, bis(N,N,N',N'-tetramethyl-D-tartaramideglycolato)diboron, bis(N,N,N',N'-tetramethyl-L-tartaramideglycolato)diboron, or any combination thereof. For example, the borylating reagent comprises bis(pinacolato)diboron.

In some implementations, the catalyst is a transition metal catalyst. For example, the transition metal catalyst comprises Ir, Re, Rh, Pd, Pt, Ni, or any combination thereof. In some instances, the transition metal catalyst comprises Ir. For example, the transition metal catalyst comprises di-µ-methoxybis(1,5-cyclooctadiene)diiridium(I), bis(1,5-cyclooctadiene)diiridium(I)dichloride, or any combination thereof.

In some implementations, the third solvent comprises an aprotic nonpolar solvent. For example, the aprotic nonpolar solvent comprises pentane, cyclopentane, hexane, cyclohexane, heptane, diethyl ether, or any combination thereof. In other examples, the third solvent further comprises MTBE. And, in some examples, the third solvent is sparged with an inert gas (e.g., argon, nitrogen, or xenon).

Another aspect of the present invention provides a method of generating a compound of Formula IV

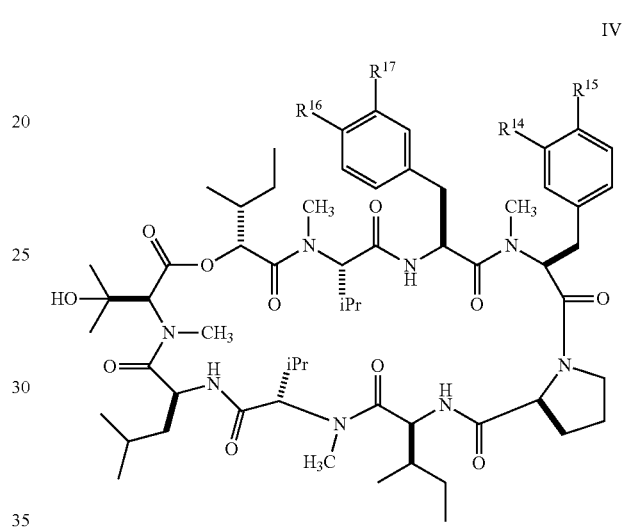

wherein one of $R^{14}$, $R^{15}$, $R^{16}$, or $R^{17}$ is optionally substituted aryl or optionally substituted heteroaryl, and the remainder are —H, comprising reacting a compound of Formula I

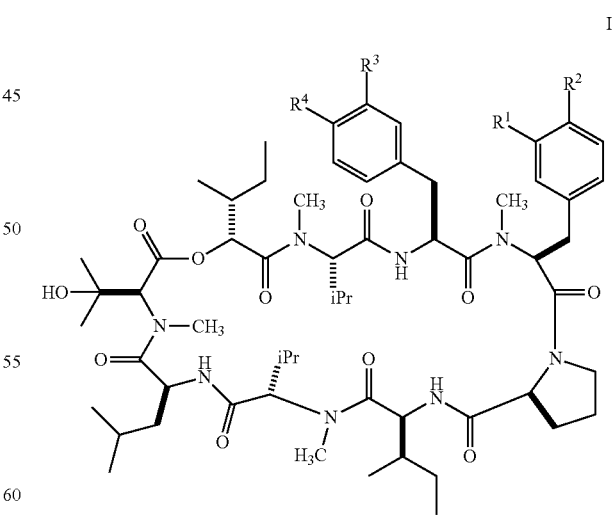

wherein one of $R^1$, $R^2$, $R^3$, or $R^4$ is —X, and the remainder are —H, and X is a halogen, with $R^{18}$—B(OH)$_2$, in the presence of a catalyst comprising Pd, wherein $R^{18}$ is an aryl or heteroaryl that is optionally substituted with one or more additional moieties.

In some implementations, the compound of Formula IV is a compound of Formula IVA

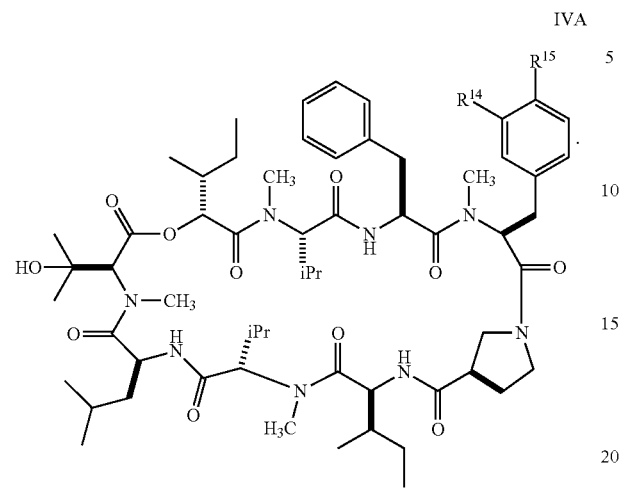

IVA

In some implementations, one of $R^{14}$, $R^{15}$, $R^{16}$, or $R^{17}$ is

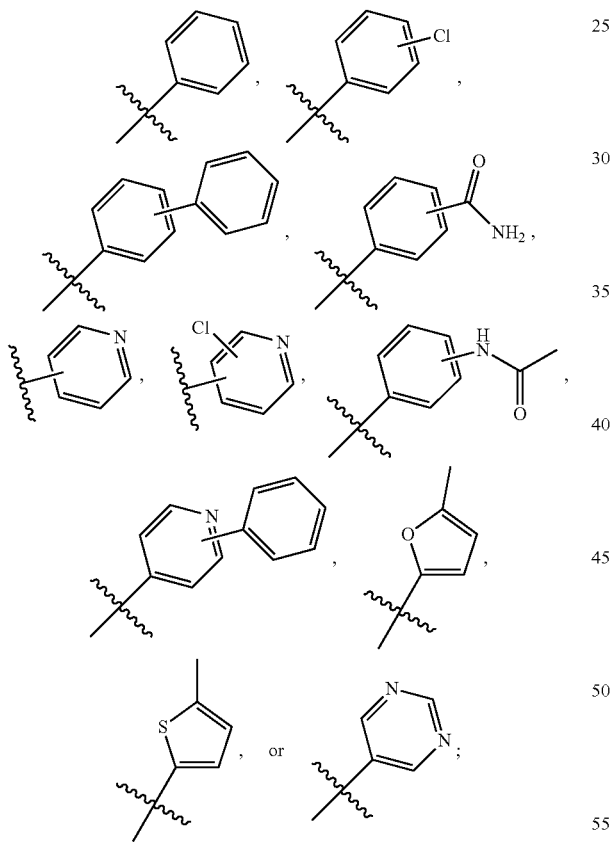

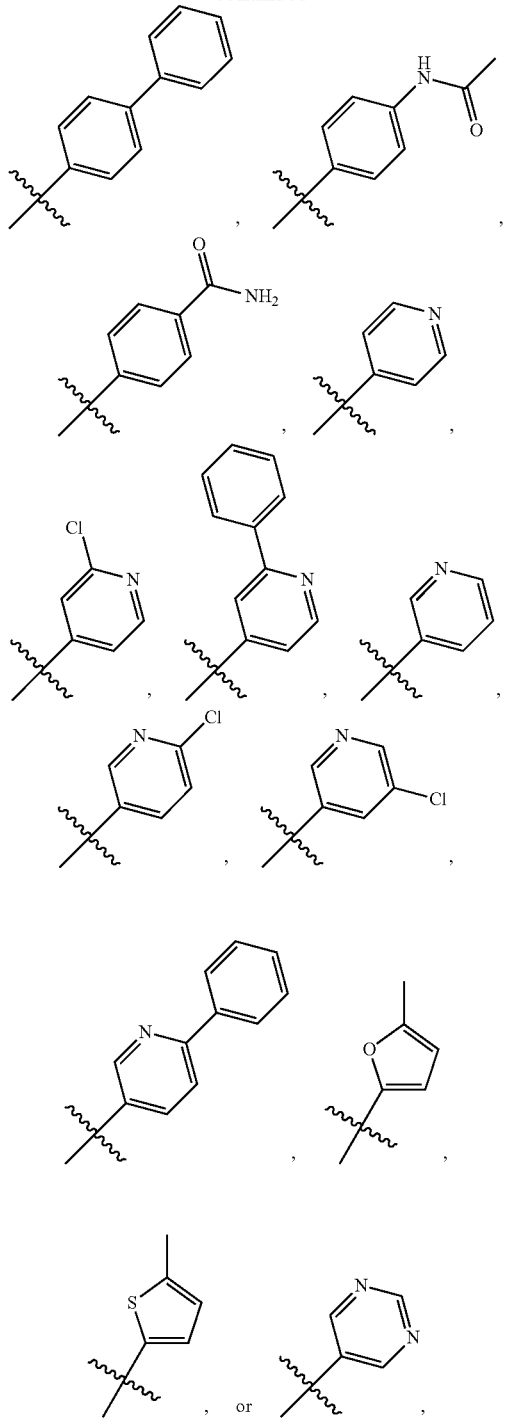

and the remainder are —H.

In other implementations, one of $R^{14}$ or $R^{15}$ is

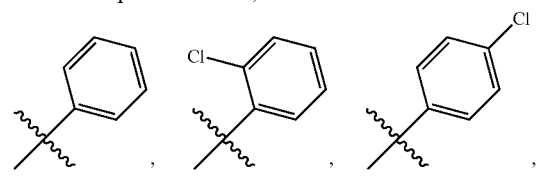

and the remainder are —H.

In some implementations, $R^{14}$ is —H.

In some implementations, the catalyst comprising Pd is selected from Pd(PPh$_3$)$_4$, Pd$_2$(dba)$_3$, PdCl$_2$(dppf), or any combination thereof.

Another aspect of the present invention provides a compound selected from

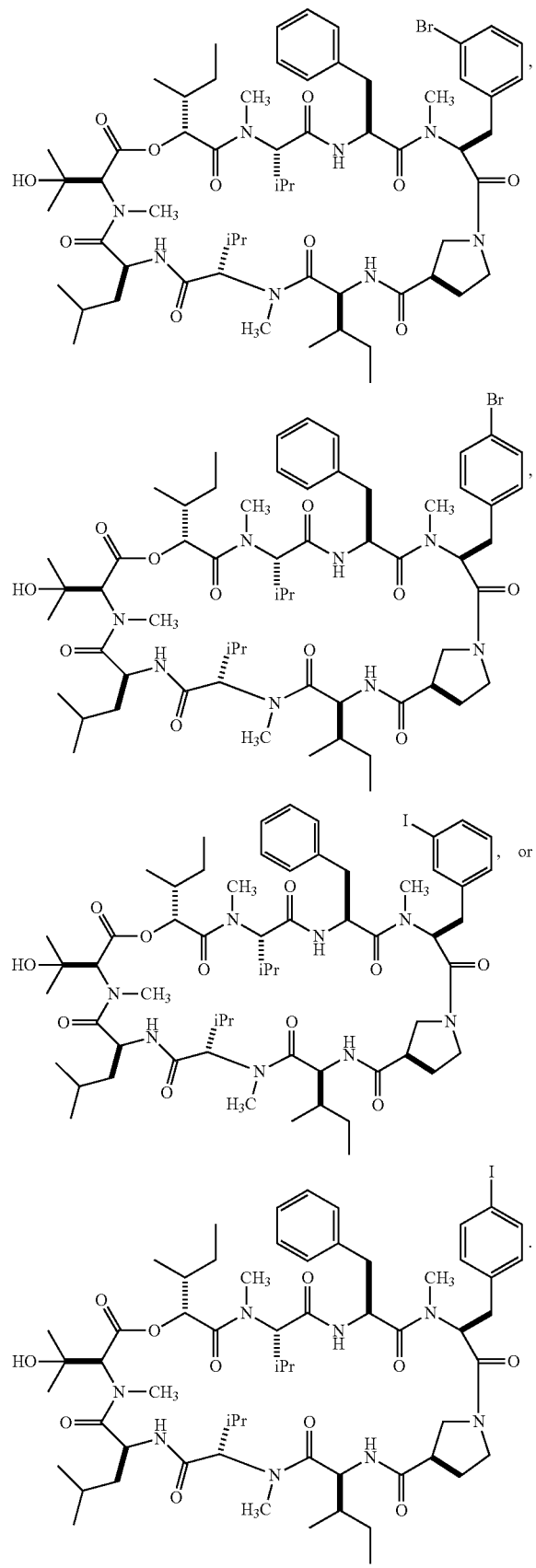

Another aspect of the present invention provides a compound of Formula Va

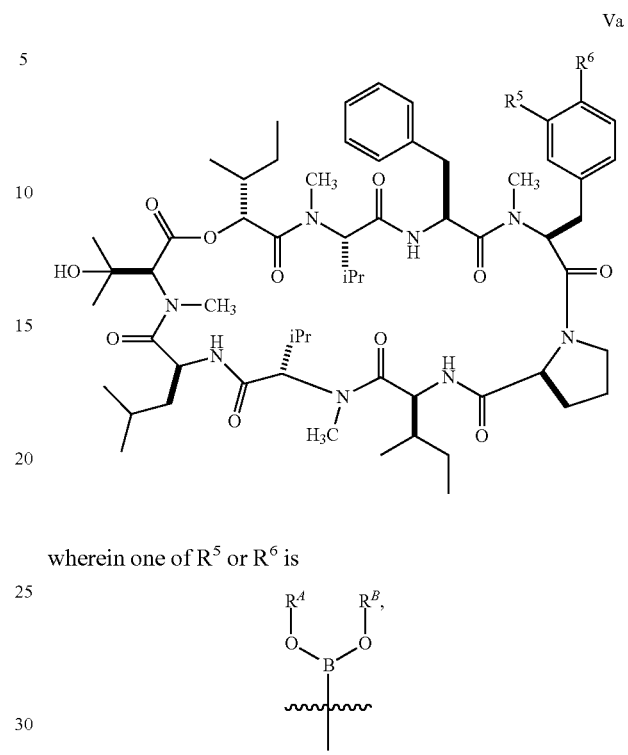

wherein one of $R^5$ or $R^6$ is

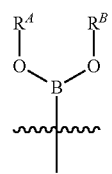

and the remainder is —H; and each of $R^A$ and $R^B$ are independently —$C_{1-4}$ alkyl, —$C_{3-6}$ cycloalkyl; or $R^A$ and $R^B$ together with the oxygen atoms to which they are attached form a 5-6 membered ring optionally substituted with 1-4 of —$C_{1-3}$ alkyl, —$C_{1-3}$ alkoxycarbonyl, —$C_{1-3}$ alkylaminocarbonyl, or any combination thereof; or $R^A$ and $R^B$ together with the oxygen atoms to which they are attached form a 7-10 membered bicyclic or tricyclic ring optionally substituted with 1-4 of —$C_{1-3}$ alkyl, —$C_{1-3}$ alkoxycarbonyl, —$C_{1-3}$ alkylaminocarbonyl, or any combination thereof.

In some embodiments, the

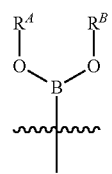

group is selected from

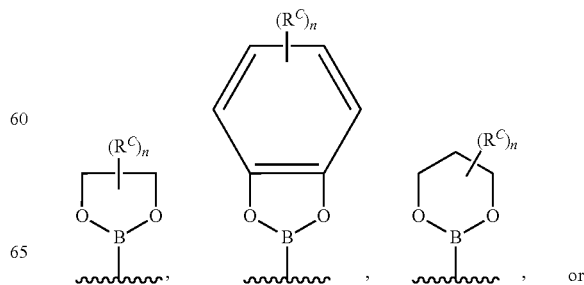

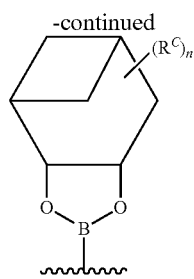

wherein each $R^C$ is independently selected from —H, —$C_{1-3}$ alkyl, —$C_{1-3}$ alkoxycarbonyl, —$C_{1-3}$ alkylaminocarbonyl, or any combination thereof, and n is 1-4.

Another aspect of the present invention provides a compound selected from

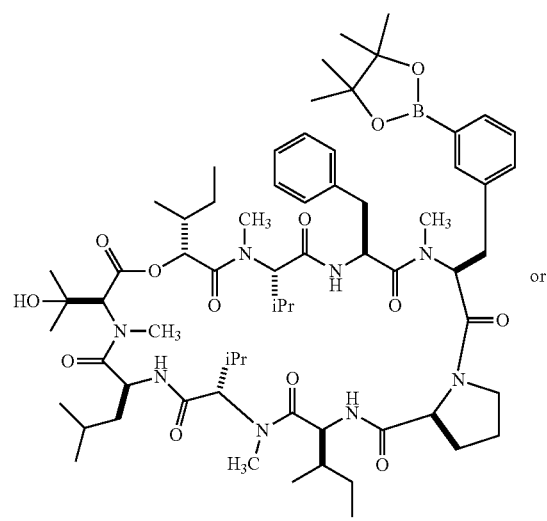

or

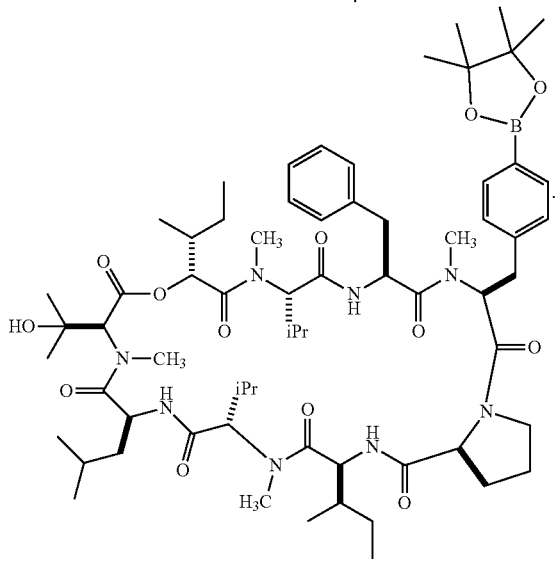

Another aspect of the present invention provides a compound of Formula II

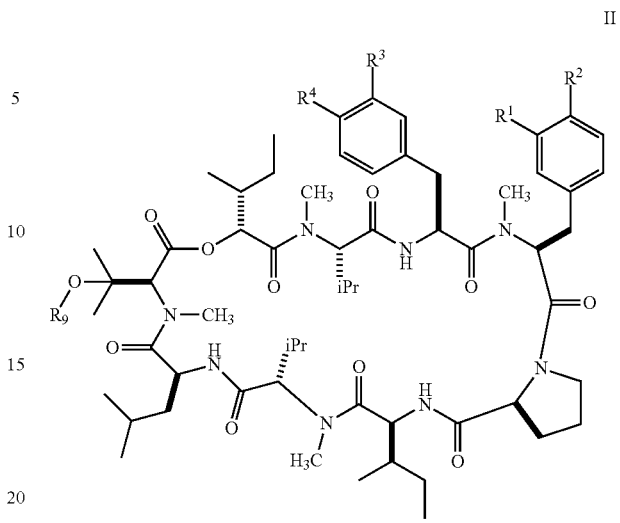

wherein one of $R^1$, $R^2$, $R^3$, or $R^4$ is —X, and the remainder are —H, wherein X is a halogen, and $R^9$ is —Si($R^{10}$)$_3$, wherein each $R^{10}$ is independently selected from an unsubstituted linear or branched $C_{1-6}$ alkyl.

Another aspect of the present invention provides a compound of Formula III

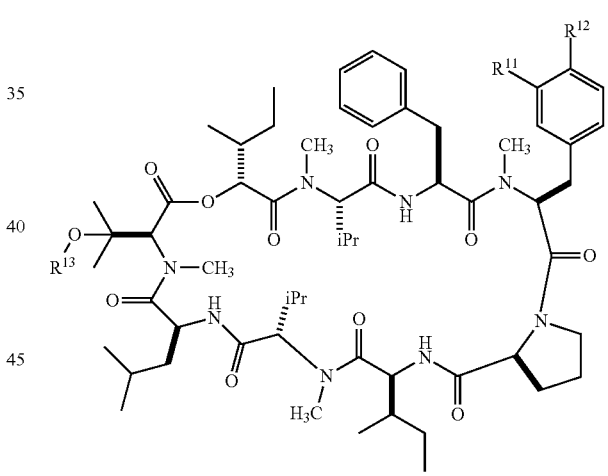

wherein one of $R^{11}$ and $R^{12}$ is —H, and the remainder is —I, —Cl, —B(OH)$_2$,

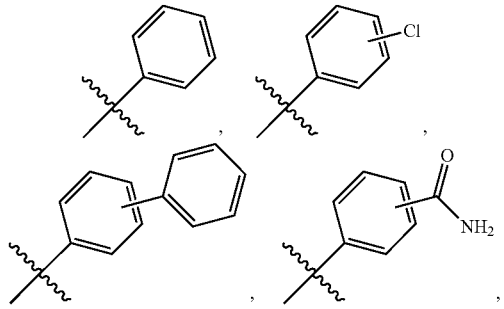

-continued

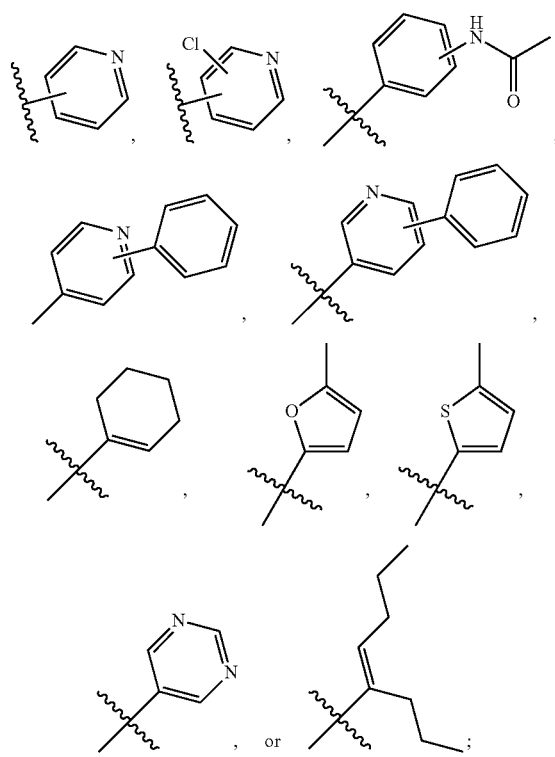

and $R^{13}$ is —H or —Si$(R^{10})_3$, wherein each $R^{10}$ is independently selected from an unsubstituted linear or branched $C_{1-6}$ alkyl.

In some embodiments, one of $R^{11}$ and $R^{12}$ is —H, and the remainder is —I, —Cl, —B(OH)$_2$,

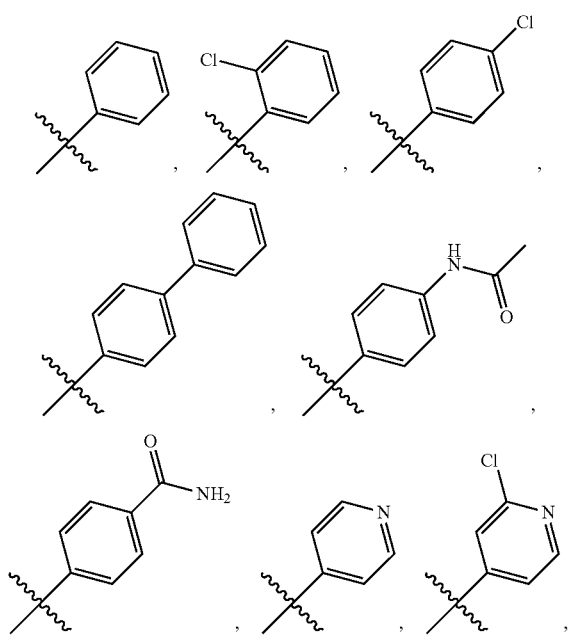

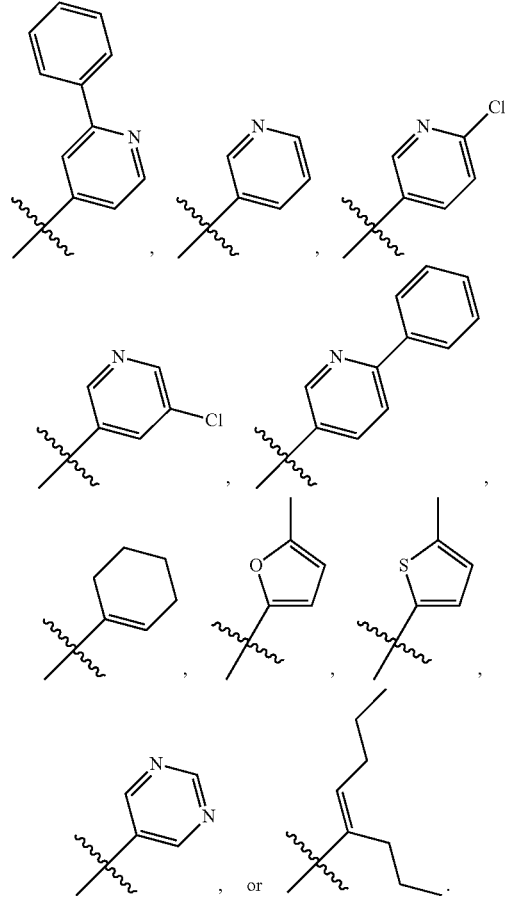

In other embodiments, $R^{13}$ is —H.

In some embodiments, $R^{12}$ is —H.

Another aspect of the present invention provides a method of inhibiting IPC synthase in a biological sample comprising contacting said sample with a compound selected from any of the AbA analogues described herein.

Another aspect of the present invention provides a method of treating a fungal infection in a patient, comprising administering to a patient in need thereof a compound selected from any of the AbA analogues described herein.

Another aspect of the present invention provides a method of reducing a population of *Candida*, *Cryptococcus*, *Aspergillus*, or any combination thereof comprising contacting said population with a compound selected from any of the AbA analogues described herein.

DETAILED DESCRIPTION

Figure 1:
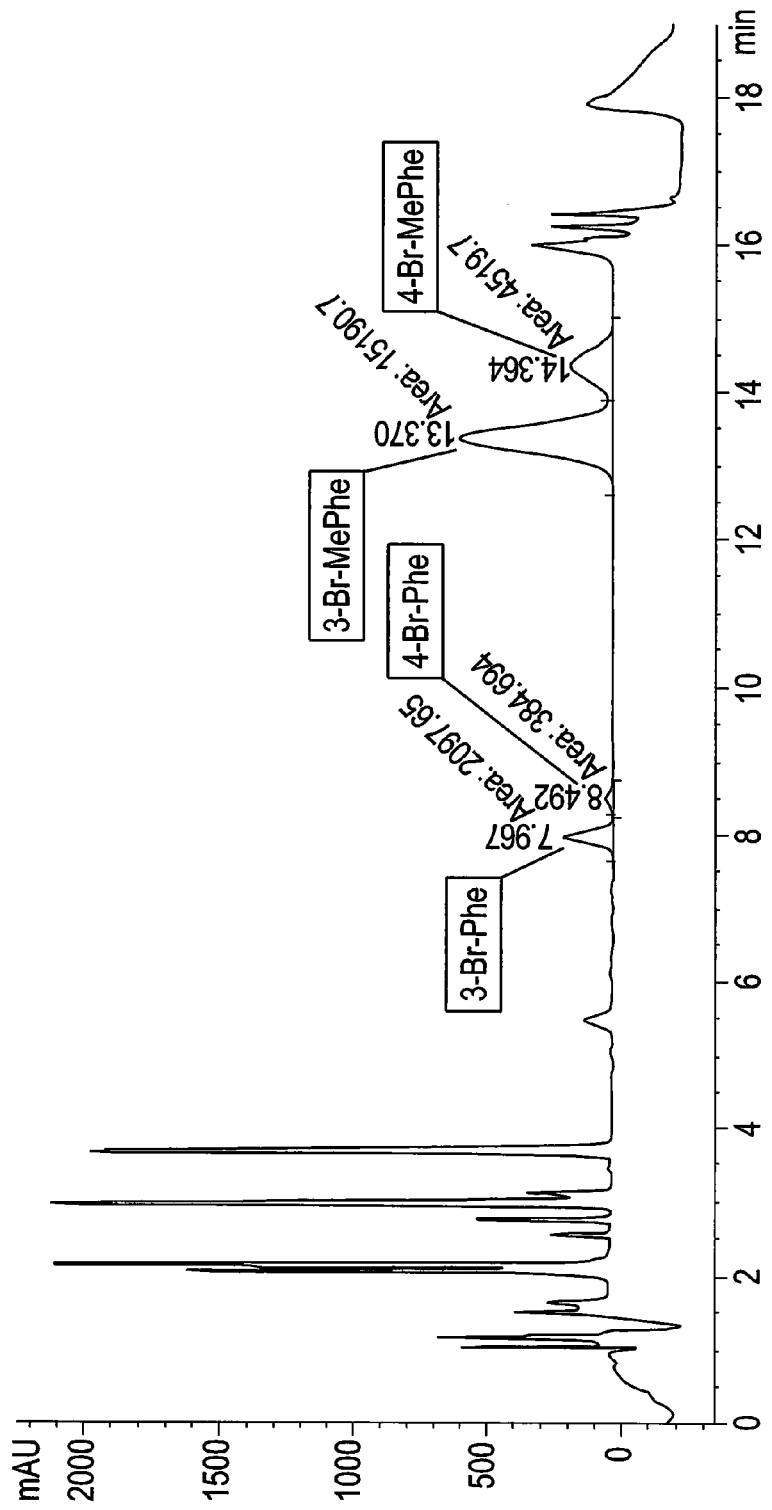
FIG. 1 presents an HPLC chromatogram for exemplary reaction products in accordance with one aspect of the present invention.

The present invention provides novel methods and compounds for preparing Aureobasidin A ("AbA") derivatives useful for treating infection.

As used herein, the following definitions shall apply unless otherwise indicated.

I. DEFINITIONS

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, "protecting group" refers to a moiety or functionality that is introduced into a molecule by chemical modification of a functional group in order to obtain chemoselectivity in a subsequent chemical reaction. Standard protecting groups are provided in Wuts and Greene: "Greene's Protective Groups in Organic Synthesis" 4th Ed, Wuts, P. G. M. and Greene, T. W., Wiley-Interscience, New York: 2006.

As described herein, compounds of the invention may optionally be substituted with one or more substituents, such as are illustrated generally above, or as exemplified by particular classes, subclasses, and species of the invention.

As used herein, the term "hydroxyl" or "hydroxy" refers to an —OH moiety.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-12 (e.g., 1-8, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-$SO_2$-], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-$SO_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-12, 2-6, or 2-4) carbon atoms and at least one double bond. Like an alkyl group, an alkenyl group can be straight or branched. Examples of an alkenyl group include, but are not limited to, allyl, 1- or 2-isopropenyl, 2-butenyl, and 2-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-$SO_2$—, cycloaliphatic-$SO_2$—, or aryl-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$SO_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-12, 2-6, or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-$SO_2$—, aliphaticamino-$SO_2$—, or cycloaliphatic-$SO_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refer to an amido group such as —N($R^X$)—C(O)—$R^Y$ or —C(O)—N($R^X$)$_2$, when used terminally, and —C(O)—N($R^X$)— or —N($R^X$)—C(O)— when used internally, wherein $R^X$ and $R^Y$ can be aliphatic, cycloaliphatic, aryl, araliphatic, heterocycloaliphatic, heteroaryl or heteroaraliphatic. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —NR$^X$R$^Y$ wherein each of R$^X$ and R$^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by —NR$^X$—, where R$^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., (aliphatic)carbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphatic-SO$_2$— or amino-SO$_2$—]; sulfinyl [e.g., aliphatic-S(O)— or cycloaliphatic-S(O)—]; sulfanyl [e.g., aliphatic-S-]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 6-12 (e.g., 8-12 or 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2]decyl, bicyclo[2.2.2]octyl, adamantyl, or ((aminocarbonyl)cycloalkyl)cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, bicyclo[2.2.2]octenyl, or bicyclo[3.3.1]nonenyl.

A cycloalkyl or cycloalkenyl group can be optionally substituted with one or more substituents such as phospho, aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic)

aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-SO$_2$— and aryl-SO$_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, the term "heterocycloaliphatic" encompasses heterocycloalkyl groups and heterocycloalkenyl groups, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo [3.3.1.0$^{3,7}$]nonyl. A monocyclic heterocycloalkyl group can be fused with a phenyl moiety to form structures, such as tetrahydroisoquinoline, which would be categorized as heteroaryls.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phospho, aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (araliphatic) carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic) carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophene-yl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1, 2,5-thiadiazolyl, or 1,8-naphthyridyl.

Without limitation, monocyclic heteroaryls include furyl, thiophene-yl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl) amino)heteroaryl]; (cyanoalkyl)heteroaryl; (alkoxy)heteroaryl; (sulfamoyl)heteroaryl [e.g., (aminosulfonyl) heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; (((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl; or (haloalkyl)heteroaryl [e.g., trihaloalkylheteroaryl].

A "heteroaraliphatic (such as a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" and "cyclic group" refer to mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.3.2]decyl, 2-oxabicyclo[2.2.2]octyl, 1-azabicyclo[2.2.2]octyl, 3-azabicyclo[3.2.1]octyl, and 2,6-dioxa-tricyclo[3.3.1.0$^{3,7}$] nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO—O—R$^Z$, wherein R$^X$ and R$^Y$ have been defined above and R$^Z$ can be aliphatic, aryl, aralphatic, heterocycloaliphatic, heteroaryl, or heteroaraliphatic.

As used herein, a "carboxy" group refers to —COOH, —COOR$^X$, —OC(O)H, —OC(O)R$^X$, when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfamoyl" group refers to the structure —O—S(O)$_2$—NR$^Y$R$^Z$ wherein R$^Y$ and R$^Z$ have been defined above.

As used herein, a "sulfonamide" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)— when used internally, wherein R$^X$ has been defined above. Exemplary sulfinyl groups include aliphatic-S(O)—, aryl-S(O)—, (cycloaliphatic(aliphatic))—S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, (cycloaliphatic(aliphatic))—S(O)$_2$—, cycloaliphatic-S(O)$_2$—, heterocycloaliphatic-S(O)$_2$—, heteroaryl-S(O)$_2$—, (cycloaliphatic(amido(aliphatic)))—S(O)$_2$— or the like.

As used herein, a "sulfoxy" group refers to —O—S(O)—R$^X$ or —S(O)—O—R$^X$, when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, the term "phospho" refers to phosphinates and phosphonates. Examples of phosphinates and phosphonates include —P(O)(R$^P$)$_2$, wherein R$^P$ is aliphatic, alkoxy, aryloxy, heteroaryloxy, (cycloaliphatic)oxy, (heterocycloaliphatic)oxy aryl, heteroaryl, cycloaliphatic or amino.

As used herein, an "aminoalkyl" refers to the structure (R$^X$)$_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

As used herein, a "guanidine" group refers to the structure —N=C(N(R$^X$R$^Y$))N(R$^X$R$^Y$) or —NR$^X$—C(=NR$^X$)NR$^X$R$^Y$ wherein R$^X$ and R$^Y$ have been defined above.

As used herein, the term "amidino" group refers to the structure —C=(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., $R^XO(O)C$-alkyl is an example of a carboxy group used terminally. A group is internal when the group is present in the middle of a substituent of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, an "aliphatic chain" refers to a branched or straight aliphatic group (e.g., alkyl groups, alkenyl groups, or alkynyl groups). A straight aliphatic chain has the structure —$[CH_2]_v$—, where v is 1-12. A branched aliphatic chain is a straight aliphatic chain that is substituted with one or more aliphatic groups. A branched aliphatic chain has the structure —$[CQQ]_v$- where Q is independently a hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^A$, $R^B$, $R^C$ and other variables contained in Formula I, II, III, IV, Ia, 1, 1a, 2 described herein encompass specific groups, such as alkyl and aryl. Unless otherwise noted, each of the specific groups for the variables $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^A$, $R^B$, $R^C$, and other variables contained therein can be optionally substituted with one or more substituents described herein. Each substituent of a specific group is further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen atoms in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an "effective amount" is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays, or as therapeutic agents.

Chemical structures and nomenclature are derived from ChemDraw, version 11.0.1, Cambridge, Mass.

It is noted that the use of the descriptors "first", "second", "third", or the like is used to differentiate separate elements (e.g., solvents, reaction steps, processes, reagents, or the like) and may or may not refer to the relative order or relative chronology of the elements described.

II. METHODS OF SYNTHESIZING AbA DERIVATIVES

One aspect of the present invention provides a novel synthesis for generating AbA derivatives that are useful for the treatment of infections. This synthetic process is useful for preparing a compound of Formula I:

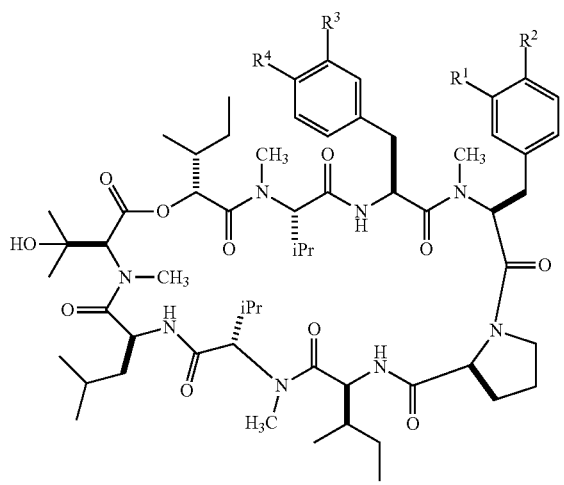

wherein one of $R^1$, $R^2$, $R^3$, or $R^4$ is —X, and the remainder are —H, wherein X is a halogen; comprising reacting a compound of Formula V with a halogenating reagent in the presence of a first solvent, i.e., solvent A, to form a compound of Formula I

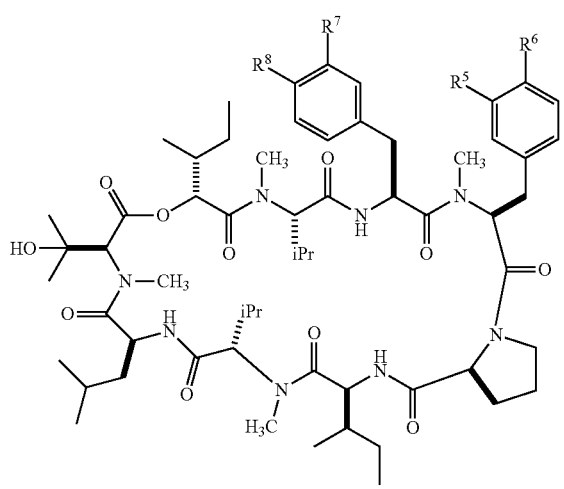

wherein one of $R^5$, $R^6$, $R^7$, or $R^8$ is

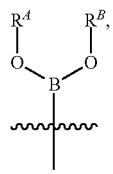

and the remainder are —H; and each of $R^A$ and $R^B$ are independently —$C_{1-4}$ alkyl, —$C_{1-3}$ cycloalkyl; or $R^A$ and $R^B$ together with the oxygen atoms to which they are attached form a 5-6 membered ring optionally substituted with 1-4 of —$C_{1-3}$ alkyl, —$C_{1-3}$ alkoxycarbonyl, —$C_{1-3}$ alkylaminocarbonyl, or any combination thereof; or $R^A$ and $R^B$ together with the oxygen atoms to which they are attached form a 7-10 membered bicyclic or tricyclic ring optionally substituted with 1-4 of —$C_{1-3}$ alkyl, —$C_{1-3}$ alkoxycarbonyl, —$C_{1-3}$ alkylaminocarbonyl, or any combination thereof.

The reaction of the compound of Formula V with the halogenating reagent to generate a compound of Formula I is referred to as the first reaction. And, a mixture comprising the compound of Formula V, solvent A, and the halogenating reagent is referred to as the first reaction mixture.

Halogenating agents useful for this method include those halogenating agents that react with the compound of Formula V to substitute the boryl moiety of $R^5$, $R^6$, $R^7$, or $R^8$ with a halogen (e.g., —Cl, —Br or —I). In some methods, the halogenating reagent comprises copper(II)halide (e.g., $CuBr_2$, $CuI_2$, or $CuCl_2$). For example, the halogenating reagent comprises copper(II)bromide, i.e., $CuBr_2$. In other methods, the halogenating reagent comprises copper(II)iodide, i.e., $CuI_2$.

Solvents useful for this first reaction are referred to as solvent A. Such solvents, i.e., solvent A, at least partially dissolve borylated organic compounds (e.g., borylated AbA) and halogenating reagents (e.g., copper(II)bromide or copper(II)iodide). In some methods, solvent A comprises a polar solvent. For example, solvent A comprises an alcohol. For instance, the alcohol comprises methanol, ethanol, iso-propanol, tert-butanol, or any combination thereof. In some examples, solvent A further comprises water. In other examples, the first solvent comprises a mixture of two or more polar solvents that are substantially miscible. For instance, the first solvent comprises a mixture of water and ethanol. In other instances, the first solvent comprises a mixture of water and ethanol in a ratio of about 0.5:1 to about 4:1 by volume of ethanol to water.

In some methods, the halogenating reagent is present in the first reaction mixture in an amount of about 1:100 to about 50:1 (e.g., 1:50 to about 5:1, 1:1 to about 5:1 or from about 2.5:1 to about 4:1) by moles of the halogenating reagent to moles of the compound of Formula V.

In some methods, the first reaction is performed under heat (e.g., from about 35° C. to about 100° C. or from about 40° C. to about 80° C.).

In other methods, the first reaction is performed at room temperature (e.g., from about 17° C. to about 30° C.).

In some implementations, the method further comprises reacting a compound of Formula 2

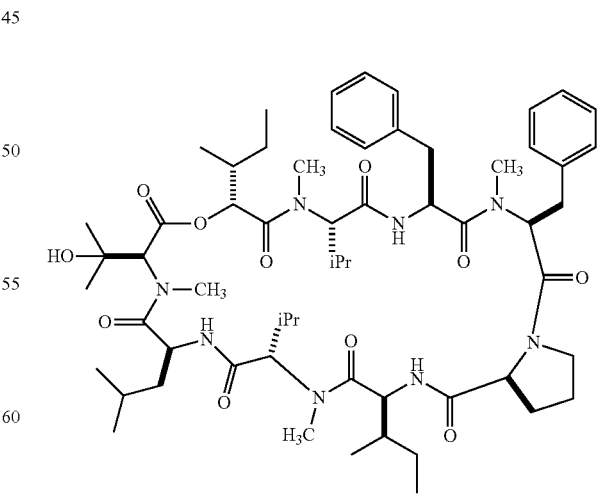

with a borylating reagent in the presence of a catalyst and a second solvent. i.e. solvent B, to generate a compound of Formula V.

The reaction of the compound of Formula 2 with the borylating reagent to generate a compound of Formula V is referred to as the second reaction. And, a mixture comprising the compound of Formula 2, solvent B, and the borylating reagent is referred to as the second reaction mixture.

In some methods, the borylating reagent comprises 4,4,5,5-tetramethyl-1,3,2-dioxaborolane, catecholborane, bis(neopentyl glycolato)diboron, bis(pinacolato)diboron, bis(hexylene glycolato)diboron, bis(catecholato)diboron, bis[(+)-pinanediolato]diboron, bis[(−)-pinanediolato]diboron, bis(diethyl-D-tartrate glycolato)diboron, bis(diethyl-L-tartrate glycolato)diboron, bis(diisopropyl-D-tartrate glycolato)diboron, bis(diisopropyl-L-tartrateglycolato)diboron, bis(N,N,N',N'-tetramethyl-D-tartaramideglycolato)diboron, bis(N,N,N',N'-tetramethyl-L-tartaramideglycolato)diboron, or any combination thereof. For example, the borylating reagent comprises bis(pinacolato)diboron.

In some methods, the borylating reagent is present in the second reaction mixture with AbA in a ratio of from about 1:20 to about 4:1 (e.g., from about 1:1 to about 4:1 or 1.5:1 to about 2.5:1) moles of borylating reagent to moles of AbA.

Catalysts useful in the present method facilitate chemical reactions wherein an aryl hydrogen atom is substituted with a boryl group (e.g., a cross-coupling reaction). In some methods, the catalyst is a transition metal catalyst. For example, the transition metal catalyst comprises Ir, Re, Rh, Pd, Pt, Ni, or any combination thereof. In some instances, the transition metal catalyst comprises Ir (e.g., di-μ-methoxybis(1,5-cyclooctadiene)diiridium(I), bis(1,5-cyclooctadiene)diiridium(I)dichloride, or any combination thereof). In other instances, the transition metal catalyst comprises Re (e.g., Cp*Re(CO)$_3$). And, in some instances, the transition metal catalyst comprises Rh (e.g., Cp*Rh($\eta^4$-C$_6$Me$_6$) or RhCl(PiPr$_3$)$_2$(N$_2$)). In other instances, the transition metal catalyst comprises Pd (e.g., 10% Pd/C).

In some methods, the catalyst further comprises Ir and a chelating reagent. For example, the chelating reagent comprises a bidentate compound. In some examples, the chelating reagent comprises 4,4'-di-tertbutyl-2,2'bipyridine.

In some methods, the catalyst comprises di-μ-methoxybis(1,5-cyclooctadiene)diiridium(I) and a 4,4'-di-tertbutyl-2,2'bipyridine chelating reagent.

In some methods, the catalyst is present in the second reaction mixture with AbA in a ratio of from about 1:7 to about 1:3 (e.g., 1:6 to about 1:4) moles of catalyst to moles of AbA.

Solvents useful for the second reaction, i.e., solvent B, at least partially dissolve the compound of Formula 2 and the borylating reagent. In some methods, the solvent B comprises an aprotic nonpolar solvent. For example, solvent B comprises pentane, cyclopentane, hexane, cyclohexane, heptane, diethyl ether, or any combination thereof. In other examples, the second solvent further comprises methyltertbutylether ("MTBE") (e.g., dry MTBE). For instance, the solvent B comprises a mixture of heptane and MTBE.

The solvent B may be further processed to remove molecular oxygen (O$_2$) from the solvent using any useful method. For example, the second solvent is sparged with an inert gas such as argon, nitrogen, xenon, any combination thereof, or another inert gas.

In some methods, the second reaction is performed under heat (e.g., from about 35° C. to about 100° C. or from about 40° C. to about 80° C.).

In other methods, the second reaction is performed at room temperature.

And, in some methods, the second reaction is performed in an inert environment (e.g., an inert gas (e.g., N$_2$) environment).

In some methods, the compound of Formula I is a compound of Formula Ia

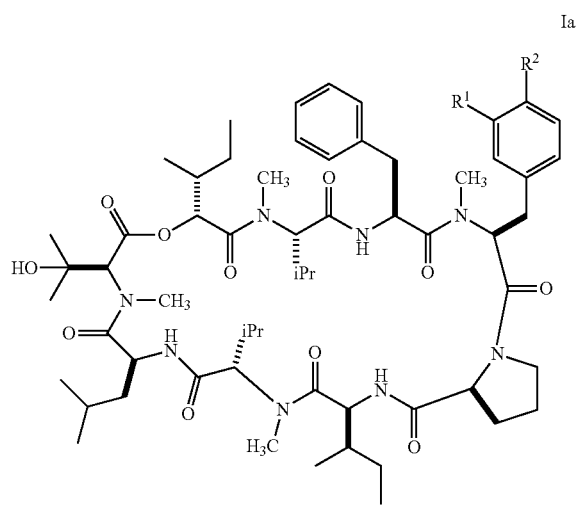

Ia wherein one of R$^1$ or R$^2$ is —X, and the remainder is —H.

In other methods, —X is selected from —Cl, —Br or —I.

In some methods, the compound of Formula V is a compound of Formula Va

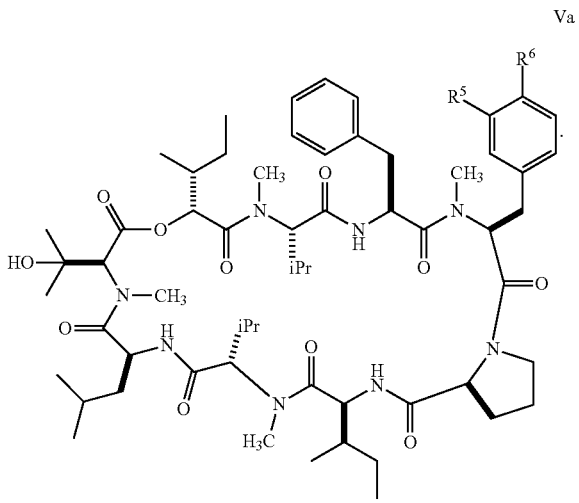

Va

In some methods, one of R$^5$ or R$^6$ is

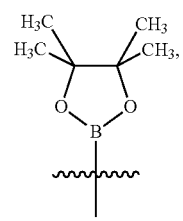 [SMILES: *B1OC(C)(C)C(C)(C)O1]

and the remainder is —H.

In some methods, one or more of the reactions are conducted under heat. For example, the reaction mixture, (e.g., the first reaction mixture, the second reaction mixture, or both) is heated to a temperature of more than about 40° C. (e.g., from about 45° C. to about 95° C.). In other examples, the reaction mixture (e.g., the first reaction mixture, the second reaction mixture, or both) is heated to a temperature of more than about 40° C. (e.g., from about 45° C. to about 95° C.).

Another aspect of the present invention provides a method of generating a compound of Formula Ia

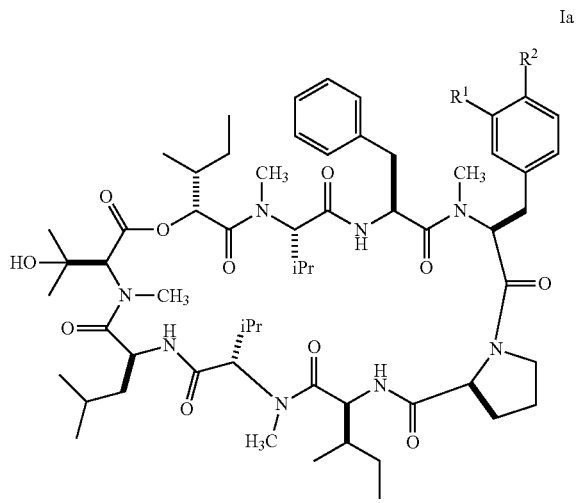

Ia wherein one of $R^1$ or $R^2$ is —Br or —I, and the remainder is —H, comprising:

reacting a compound of Formula Va with a brominating reagent or iodinating reagent in the presence of a first solvent, i.e., solvent A, to form a compound of Formula Ia

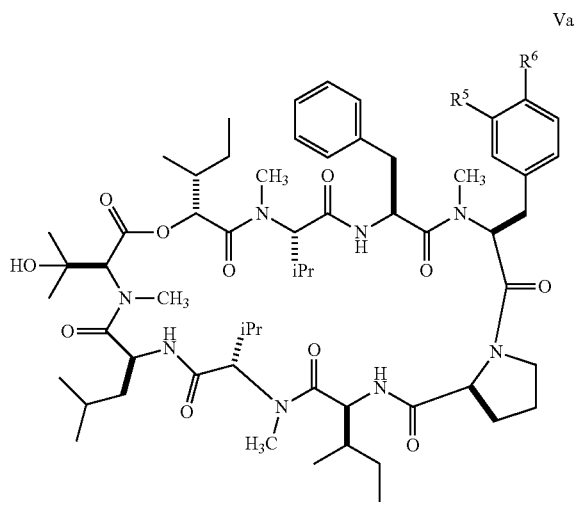

Va wherein one of $R^5$ or $R^6$ is

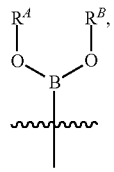

and the remainder is —H; and each of $R^A$ and $R^B$ are independently —$C_{1-4}$ alkyl, —$C_{3-6}$ cycloalkyl; or $R^A$ and $R^B$ together with the oxygen atoms to which they are attached form a 5-6 membered ring optionally substituted with 1-4 of —$C_{1-3}$ alkyl, —$C_{1-3}$ alkoxycarbonyl, —$C_{1-3}$ alkylaminocarbonyl, or any combination thereof; or $R^A$ and $R^B$ together with the oxygen atoms to which they are attached form a 7-10 membered bicyclic or tricyclic ring optionally substituted with 1-4 of —$C_{1-3}$ alkyl, —$C_{1-3}$ alkoxycarbonyl, —$C_{1-3}$ alkylaminocarbonyl, or any combination thereof.

Brominating reagents useful for this method include those brominating reagents that react with the compound of Formula Va to substitute the boryl moiety of $R^5$, $R^6$, $R^7$, or $R^8$ with —Br. In some methods, the brominating reagent comprises copper(II)bromide.

Iodinating reagents useful for this method include those iodinating reagents that react with the compound of Formula Va to substitute the boryl moiety of $R^5$, $R^6$, $R^7$, or $R^8$ with —I. In some methods, the iodinating reagent comprises copper(II)iodide. Note that iodinating reagents useful for this method may be generated in situ.

Solvents useful for this reaction include those solvents referred to as solvent A. Such solvents, i.e., solvent A, at least partially dissolve borylated organic compounds (e.g., borylated AbA), brominating reagents (e.g., copper(II)bromide) or iodinating reagents (e.g., copper(II)iodide). In some methods, solvent A comprises a polar solvent. For example, solvent A comprises an alcohol. For instance, the alcohol comprises methanol, ethanol, iso-propanol, tert-butanol, or any combination thereof. In other examples, solvent A further comprises water. In other examples, the first solvent comprises a mixture of two or more polar solvents that are substantially miscible. For instance, the first solvent comprises a mixture of water and ethanol. In other instances, the first solvent comprises a mixture of water and ethanol in a ratio of about 1:1 to about 4:1 by volume of ethanol to water.

In some methods, the brominating reagent is present in a reaction mixture comprising the compound of Formula V in a ratio of about 1:1 to about 5:1 (e.g., from about 2.5:1 to about 4:1) by moles of the halogenating reagent to moles of the compound of Formula V.

In some methods, this reaction is performed under heat (e.g., from about 35° C. to about 100° C. or from about 40° C. to about 80° C.).

In other methods, this reaction is performed at room temperature (e.g., from about 17° C. to about 30° C.).

In some implementations, the method further comprises reacting a compound of Formula 2

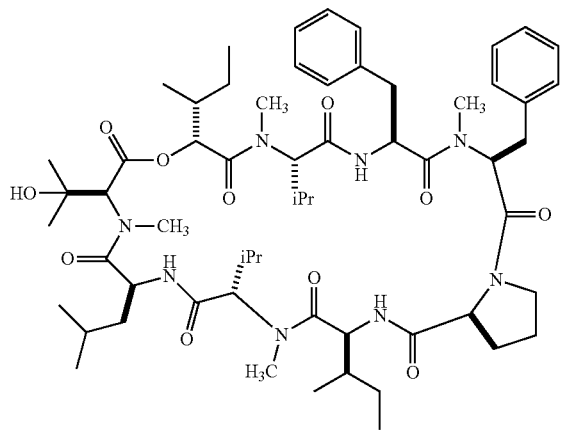

with a borylating reagent in the presence of a catalyst and a second solvent, i.e., solvent B, to generate a compound of Formula Va.

In some methods, the borylating reagent comprises 4,4,5,5-tetramethyl-1,3,2-dioxaborolane, catecholborane, bis(neopentyl glycolato)diboron, bis(pinacolato)diboron, bis(hexylene glycolato)diboron, bis(catecholato)diboron, bis[(+)-pinanediolato]diboron, bis[(−)-pinanediolato]diboron, bis(diethyl-D-tartrate glycolato)diboron, bis(diethyl-L-tartrate glycolato)diboron, bis(diisopropyl-D-tartrate glycolato)diboron, bis(diisopropyl-L-tartrateglycolato)diboron, bis(N,N,N',N'-tetramethyl-D-tartaramideglycolato)diboron, bis(N,N,N',N'-tetramethyl-L-tartaramideglycolato)diboron, or any combination thereof. For example, the borylating reagent comprises bis(pinacolato)diboron.

In some methods, the borylating reagent is present in a reaction mixture comprising AbA in a ratio of from about 1:1 to about 4:1 (e.g., 1.5:1 to about 2.5:1) moles of borylating reagent to moles of AbA.

Catalysts useful in the present method facilitate chemical reactions wherein an aryl hydrogen atom is substituted with a boryl group (e.g., a cross-coupling reaction). In some methods, the catalyst is a transition metal catalyst. For example, the transition metal catalyst comprises Ir, Re, Rh, Pd, Pt, Ni, or any combination thereof. In some instances, the transition metal catalyst comprises Ir (e.g., di-μ-methoxybis(1,5-cyclooctadiene)diiridium(I), bis(1,5-cyclooctadiene)diiridium(I)dichloride, or any combination thereof). In other instances, the transition metal catalyst comprises Re (e.g., Cp*Re(CO)$_3$). And, in some instances, the transition metal catalyst comprises Rh (e.g., Cp*Rh(η$^4$-C$_6$Me$_6$) or RhCl(PiPr$_3$)$_2$ (N$_2$)). In other instances, the transition metal catalyst comprises Pd (e.g., 10% Pd/C).

In some methods, the catalyst further comprises Ir and a chelating reagent. For example, the chelating reagent comprises a bidentate compound. In some examples, the chelating reagent comprises 4,4'-di-tertbutyl-2,2'bipyridine.

In some methods, the catalyst comprises di-μ-methoxybis(1,5-cyclooctadiene)diiridium(I) and a 4,4'-di-tertbutyl-2,2'bipyridine chelating reagent.

In some methods, the catalyst is present in the second reaction mixture with AbA in a ratio of from about 1:7 to about 1:3 (e.g., 1:6 to about 1:4) moles of catalyst to moles of AbA.

Solvents useful for reactions of Aba with a borylating reagent include those solvents referred to as solvent B. In some methods, the solvent B comprises an aprotic nonpolar solvent. For example, solvent B comprises pentane, cyclopentane, hexane, cyclohexane, heptane, diethyl ether, or any combination thereof. In other examples, the second solvent further comprises methyltertbutylether ("MTBE") (e.g., dry MTBE). For instance, the solvent B comprises a mixture of heptane and MTBE.

The solvent B may be further processed to remove molecular oxygen (O$_2$) from the solvent using any useful method. For example, the second solvent is sparged with argon, nitrogen, xenon, any combination thereof, or another inert gas.

In some methods, this reaction is performed under heat (e.g., from about 35° C. to about 100° C. or from about 40° C. to about 80° C.).

In other methods, this reaction is performed at room temperature.

And, in some methods, this reaction is performed in an inert environment (e.g., an inert gas (e.g., N$_2$) environment).

In some methods, the compound of Formula Ia is

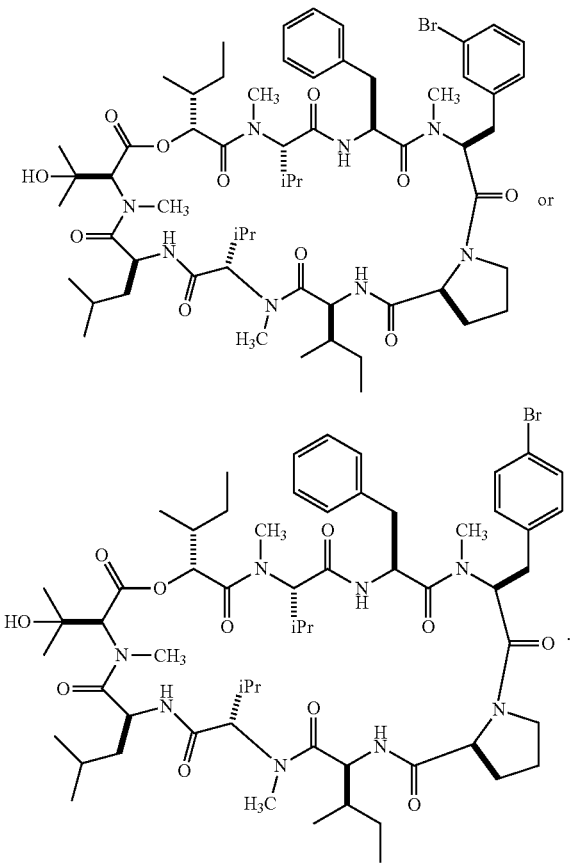

In some methods, the halogenating reagent comprises copper(II)halide (e.g., CuCl$_2$, or CuBr$_2$).

In some methods, the compound of Formula Ia is

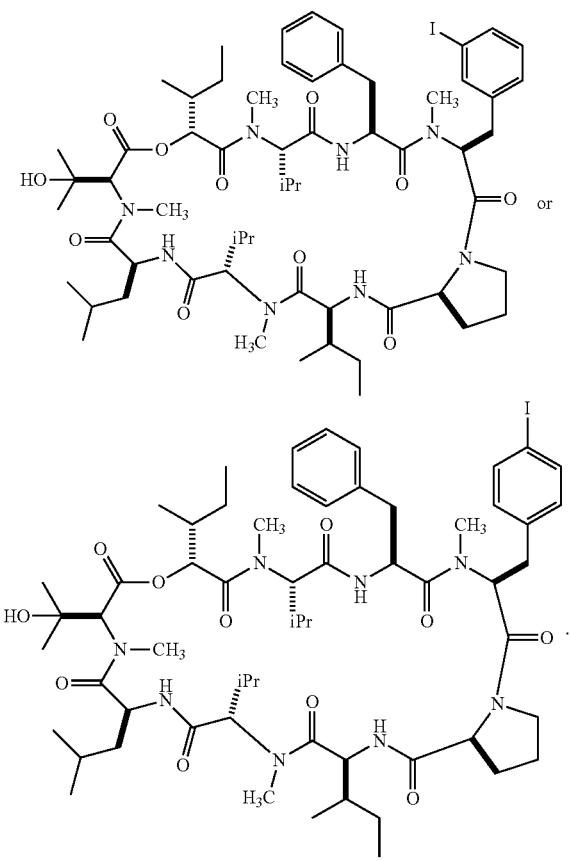

or

In some methods, the iodinating reagent comprises copper (II)iodide (e.g., CuI₂, or CuI₂).

In other methods, one of $R^5$ or $R^6$ in Formula Va is

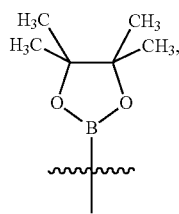

and the remainder is —H.

In some methods, one or more of the reactions are conducted under heat. For example, the reaction mixture, (e.g., the first reaction mixture, the second reaction mixture, or both) is heated to a temperature of more than about 40° C. (e.g., from about 45° C. to about 95° C.). In other examples, the reaction mixture (e.g., the first reaction mixture, the second reaction mixture, or both) is heated to a temperature of more than about 40° C. (e.g., from about 45° C. to about 95° C.).

Additional Elaboration of Halogenated AbA

Halogenated AbA is amenable to further elaboration. Examples of methods of elaborating halogenated AbA are provided below.

Another aspect of the present invention provides a method of generating a compound of Formula II

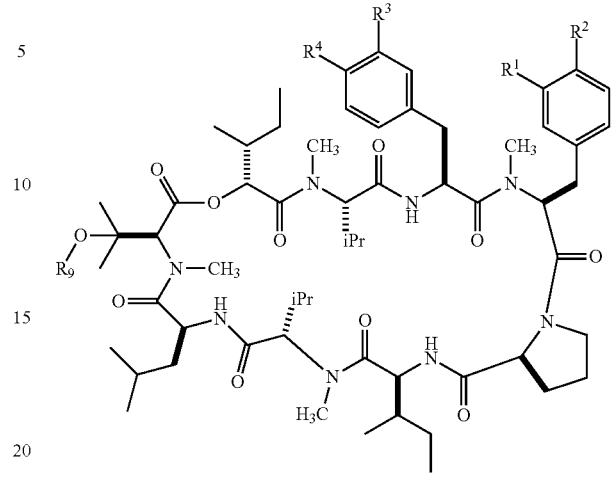

wherein one of $R^1$, $R^2$, $R^3$, or $R^4$ is —X, and the remainder are —H, wherein X is a halogen, and $R^9$ is —Si($R^{10}$)₃, wherein each $R^{10}$ is independently selected from an unsubstituted linear or branched $C_{1-5}$ alkyl; comprising:

reacting a compound of Formula I with Si($R^{10}$)₃$X^1$, wherein $X^1$ is a halogen, —OTf, —OTs, or —OMs, in the presence of a first solvent, i.e., solvent C, and a base to form a compound of Formula II

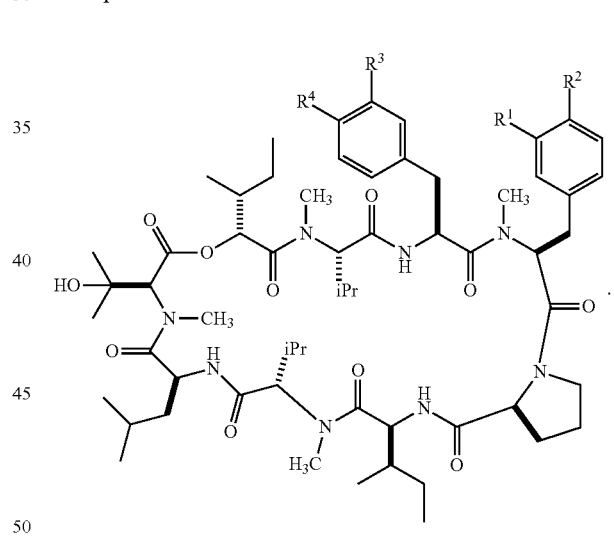

In some methods, $R^9$ is —Si($R^{10}$)₃, and each $R^{10}$ is independently selected from methyl, ethyl, propyl, isopropyl, butyl, sec-butyl, or tert-butyl.

Solvents useful for this reaction are referred to as solvent C. In some methods, solvent C comprises a polar solvent. For example, solvent C comprises dimethylformamide, dichloromethane, tetrahydrofuran, ethyl acetate, acetone, acetonitrile, dimethylsulfoxide, or any combination thereof.

In some methods, the base comprises a tertiary amine base. For example, the amine base comprises imidazole, trimethylamine, triethylamine, or an N-substituted or N,N-substituted piperizine (e.g., N,N-dimethylpiperazine), piperidine (e.g., N-methylpiperidine), pyrrolidine (e.g., N-methylpyrrolidine), or any combination thereof.

In some implementations, the method further comprises reacting a compound of Formula V with a halogenating reagent in the presence of a second solvent. i.e., solvent A, to form a compound of Formula I

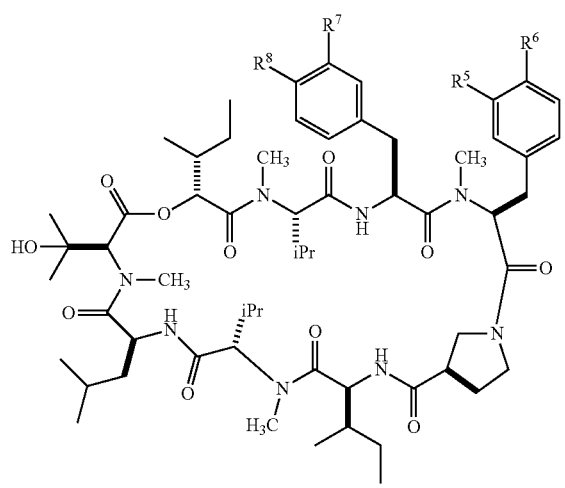

wherein one of $R^5$, $R^6$, $R^7$, or $R^8$ is

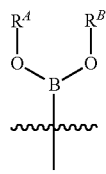

and the remainder are —H; and each of $R^A$ and $R^B$ are independently —$C_{1-4}$ alkyl, —$C_{1-4}$ cycloalkyl; or $R^A$ and $R^B$ together with the oxygen atoms to which they are attached form a 5-6 membered ring optionally substituted with 1-4 of —$C_{1-3}$ alkyl, —$C_{1-3}$ alkoxycarbonyl, —$C_{1-3}$ alkylaminocarbonyl, or any combination thereof; or $R^A$ and $R^B$ together with the oxygen atoms to which they are attached form a 7-10 membered bicyclic or tricyclic ring optionally substituted with 1-4 of —$C_{1-3}$ alkyl. —$C_{1-3}$ alkoxycarbonyl, —$C_{1-3}$ alkylaminocarbonyl, or any combination thereof.

In some implementations, the method further comprises reacting a compound of Formula 2

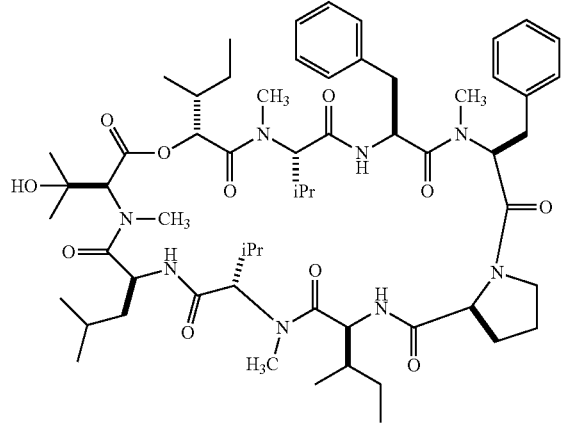

with a borylating reagent in the presence of a catalyst and a third solvent, i.e., solvent B, to generate a compound of Formula V.

In some methods, the compound of Formula I is a compound of Formula Ia

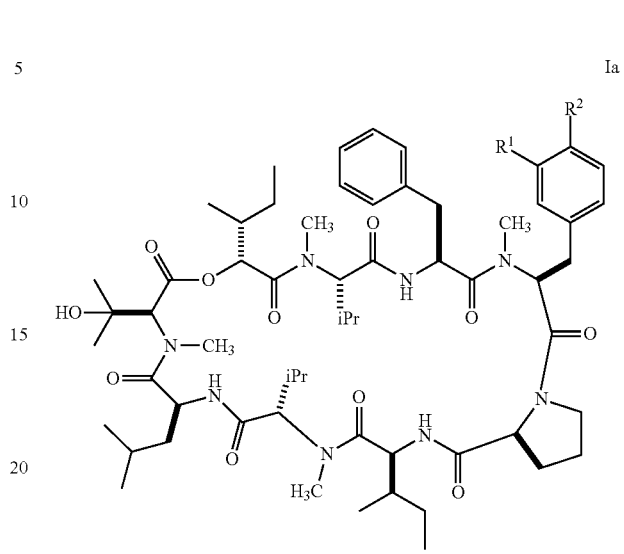

wherein one of $R^1$ or $R^2$ is —X, and the remainder is —H.

In other methods, —X is selected from —Cl, —Br, or —I.

In some methods, the halogenating reagent is as described above.

In some methods, the compound of Formula V is a compound of Formula Va

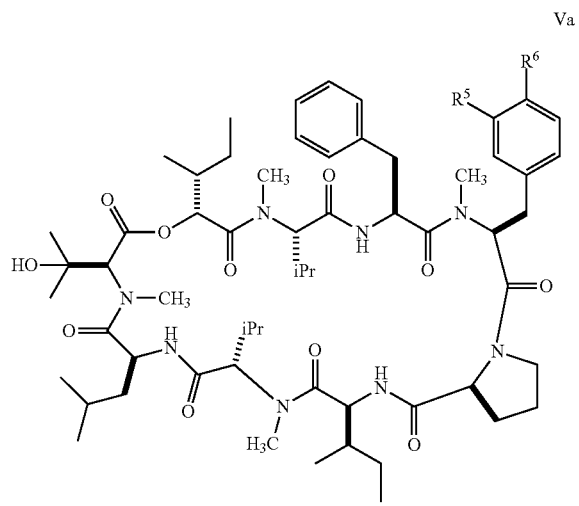

In some methods, one of $R^5$ or $R^6$ is

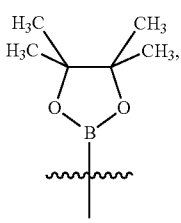

and the remainder is —H.

In some methods, solvent B comprises a polar solvent, such as any of those described above.

In some methods, the borylating reagent is as described above.

In some methods, the catalyst is as described above.

In some methods, solvent B comprises an aprotic nonpolar solvent such as those described above.

Compounds of Formula I may be further derivatized via cross-coupling reaction schemes (e.g., Suzuki cross-coupling).

Another aspect of the present invention provides a method of generating a compound of Formula IV

IV

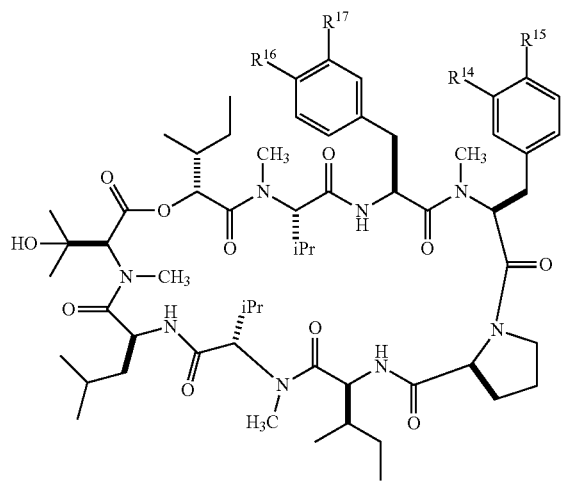

wherein one of $R^{14}$, $R^{15}$, $R^{16}$, or $R^{17}$ is optionally substituted aryl or optionally substituted heteroaryl, and the remainder are —H, comprising:

reacting a compound of Formula I

I

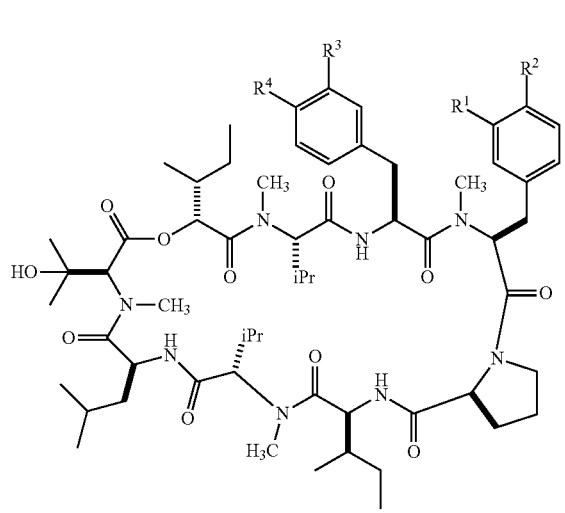

wherein one of $R^1$, $R^2$, $R^3$, or $R^4$ is —X, and the remainder are —H, wherein X is a halogen, with $R^{18}$—B(OH)$_2$, in the presence of a catalyst comprising Pd, wherein $R^{18}$ is an aryl or heteroaryl that is optionally substituted with one or more additional moieties.

In some methods, the compound of Formula IV is

IVA

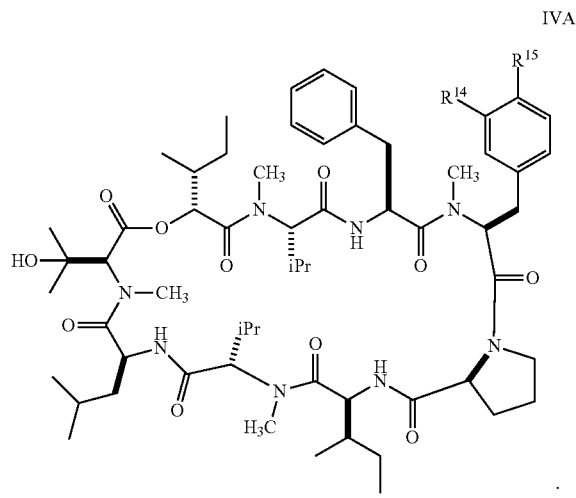

In some methods, one of $R^{14}$, $R^{15}$, $R^{16}$, or $R^{17}$ is

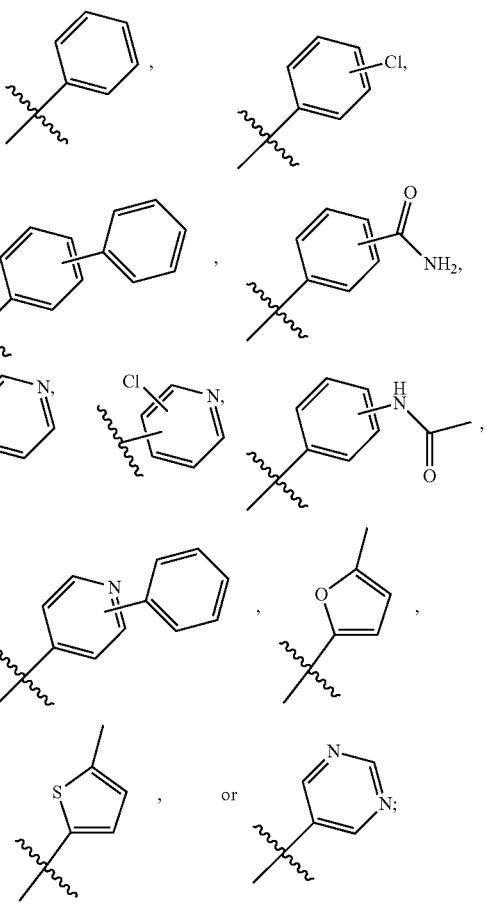

and the remainder are —H. For example, one of $R^{14}$, $R^{15}$, $R^{16}$, or $R^{17}$ is

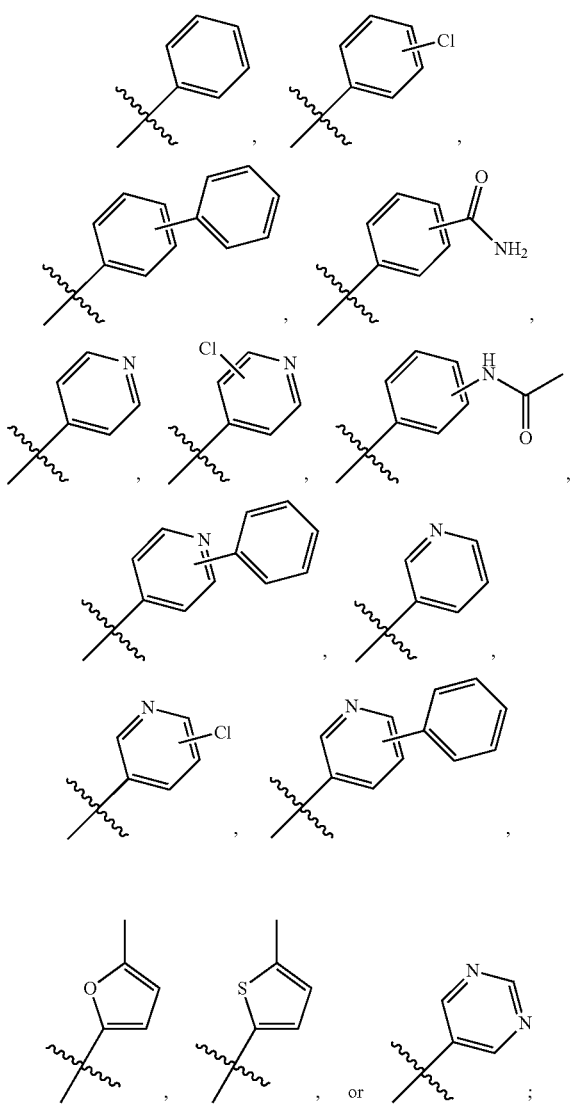
and the remainder are —H. In other examples, one of $R^{14}$ or $R^{15}$ is
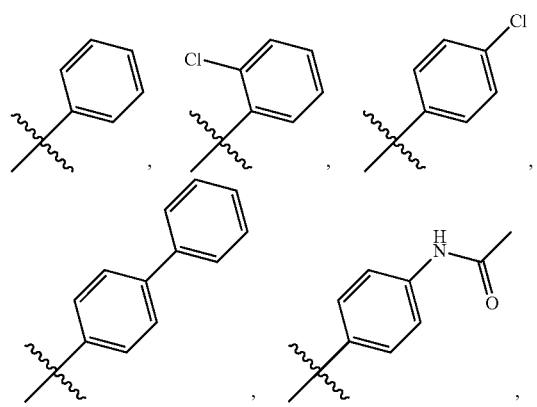
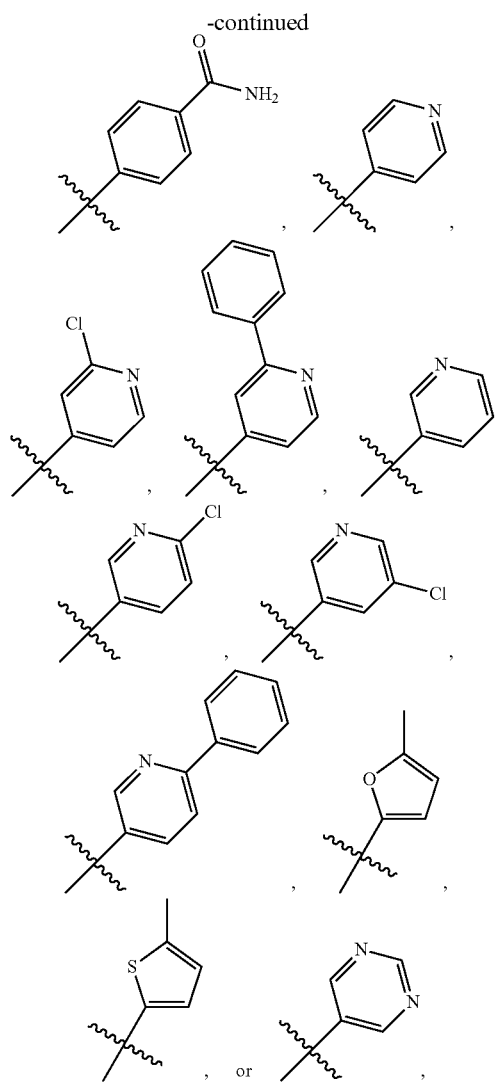
and the remainder is are —H. For example, $R^{14}$ is —H.
In some methods, the catalyst comprising Pd is selected from Pd(PPh$_3$)$_4$, Pd$_2$(dba)$_3$, or PdCl$_2$(dppf).
III. NOVEL COMPOUNDS
Another aspect of the present invention provides a compound selected from
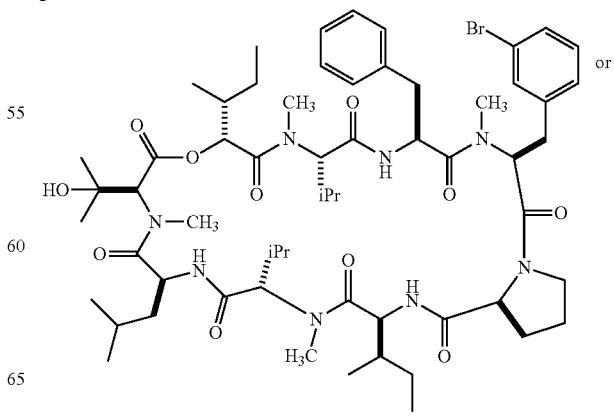

Another aspect of the present invention provides a compound selected from

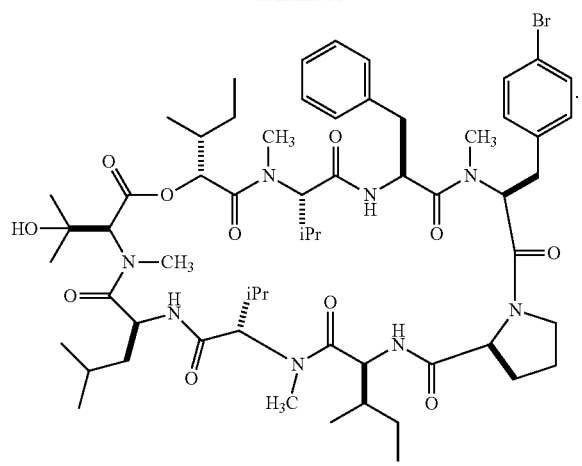

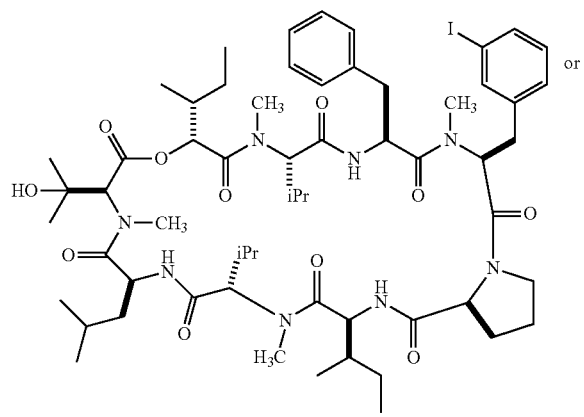

or

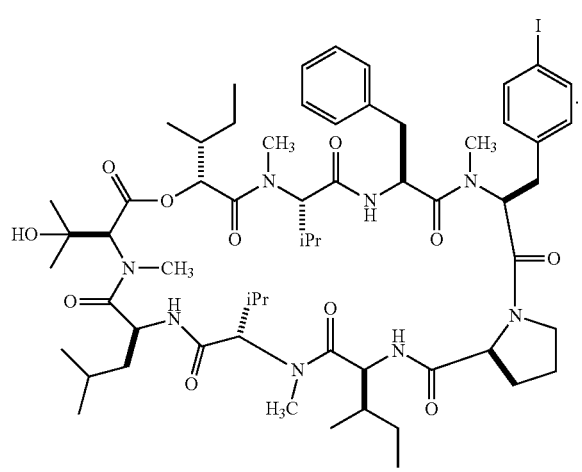

Another aspect of the present invention provides a compound of Formula Va

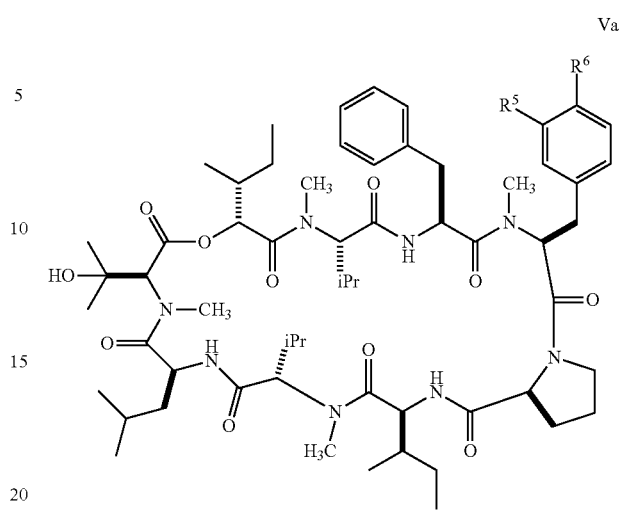

wherein one of $R^5$ or $R^6$ is

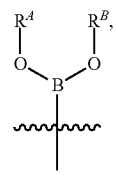

and the remainder is —H; and each of $R^A$ and $R^B$ are independently —$C_{1-4}$ alkyl, —$C_{3-6}$ cycloalkyl; or $R^A$ and $R^B$ together with the oxygen atoms to which they are attached form a 5-6 membered ring optionally substituted with 1-4 of —$C_{1-3}$ alkyl, —$C_{1-3}$ alkoxycarbonyl, —$C_{1-3}$ alkylaminocarbonyl, or any combination thereof; or $R^A$ and $R^B$ together with the oxygen atoms to which they are attached form a 7-10 membered bicyclic or tricyclic ring optionally substituted with 1-4 of —$C_{1-3}$ alkyl, —$C_{1-3}$ alkoxycarbonyl, —$C_{1-3}$ alkylaminocarbonyl, or any combination thereof.

In some embodiments, the

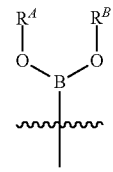

group is selected from

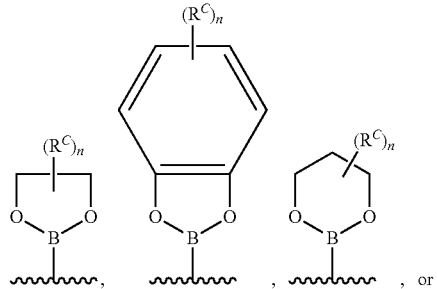

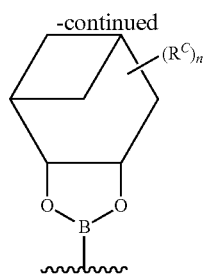

wherein each $R^C$ is independently selected from —H, —$C_{1-3}$ alkyl, —$C_{1-3}$ alkoxycarbonyl, —$C_{1-3}$ alkylaminocarbonyl, or any combination thereof, and n is 1-4.

Another aspect of the present invention provides a compound selected from

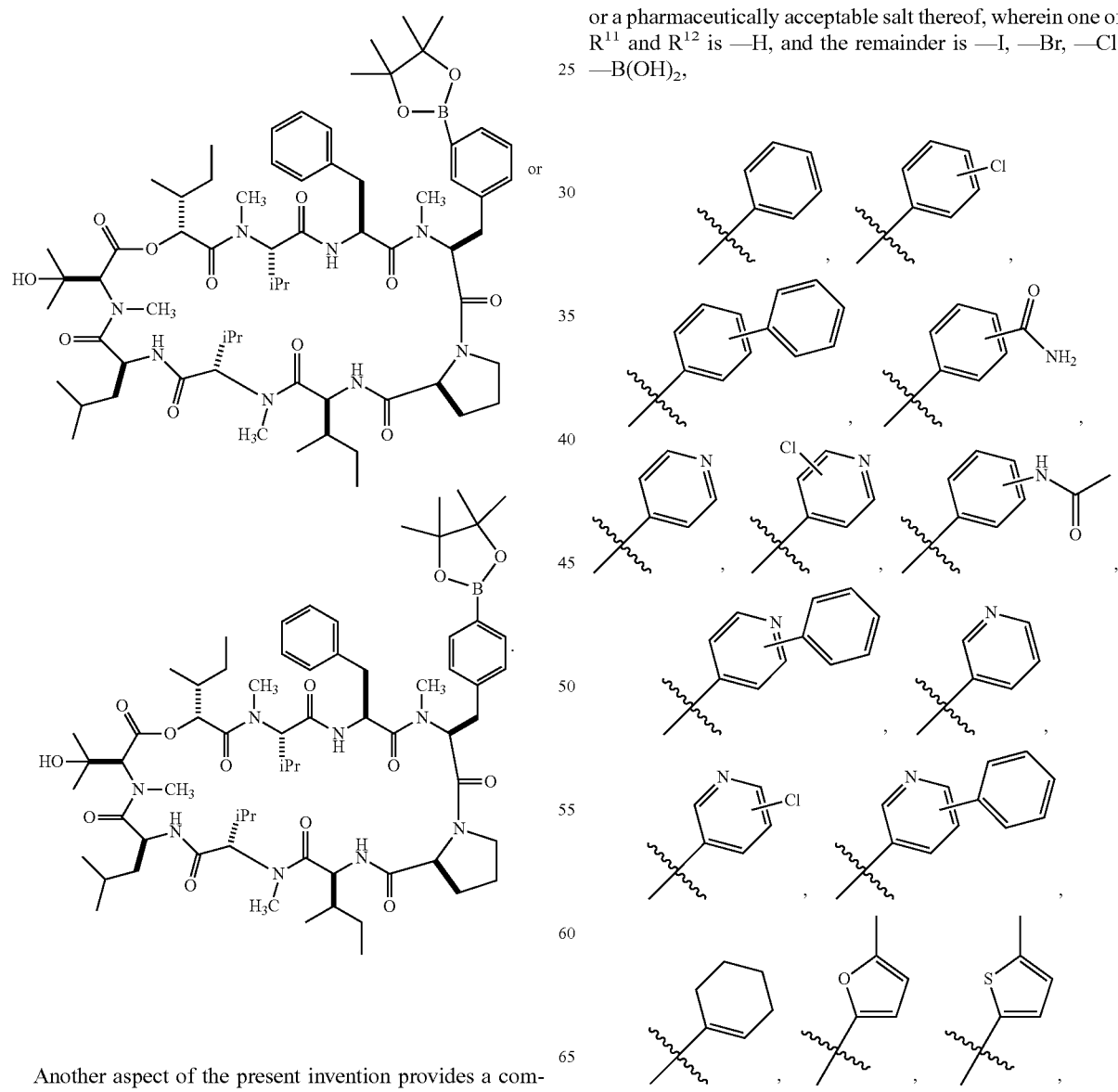

Another aspect of the present invention provides a compound of Formula III

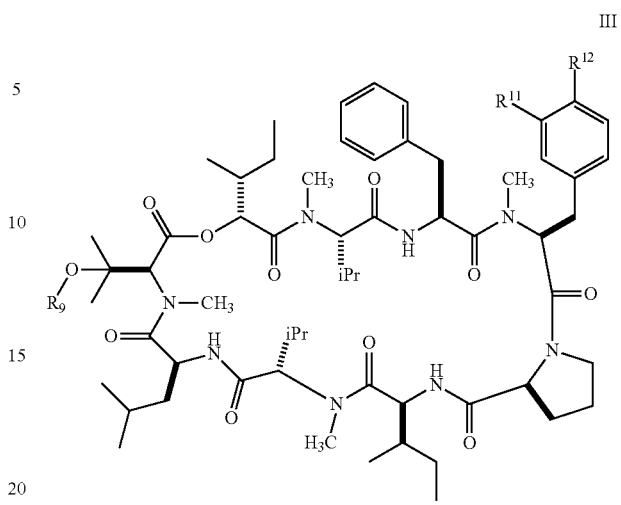

or a pharmaceutically acceptable salt thereof, wherein one of $R^{11}$ and $R^{12}$ is —H, and the remainder is —I, —Br, —Cl, —B(OH)$_2$, -continued

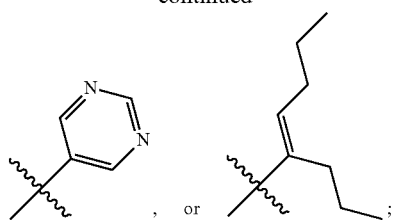
, or ;

and R[13] is —H or —Si(R[10])$_3$, wherein each R[10] is independently selected from an unsubstituted linear or branched C$_{1-6}$ alkyl.

In some embodiments, one of R[11] and R[12] is —H, and the remainder is —I, —Cl, —Br, —B(OH)$_2$,

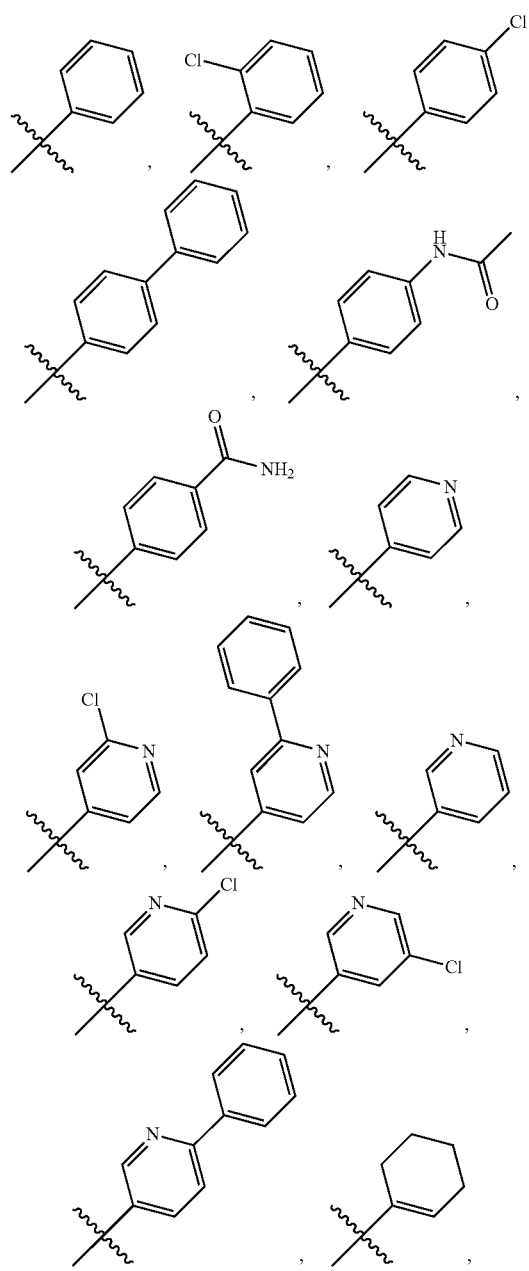

-continued

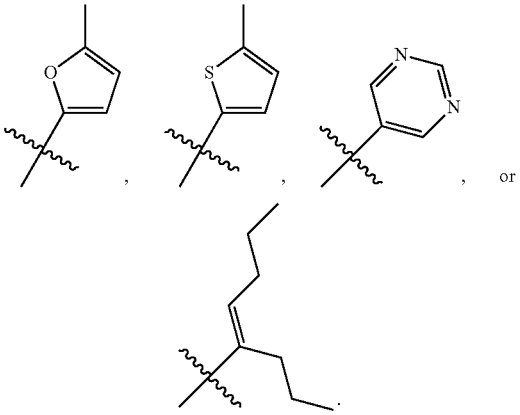

In some embodiments, R[12] is —H.

IV. PHARMACEUTICAL COMPOSITIONS

Another aspect of the present invention provides a pharmaceutical composition comprising a compound of Formula III

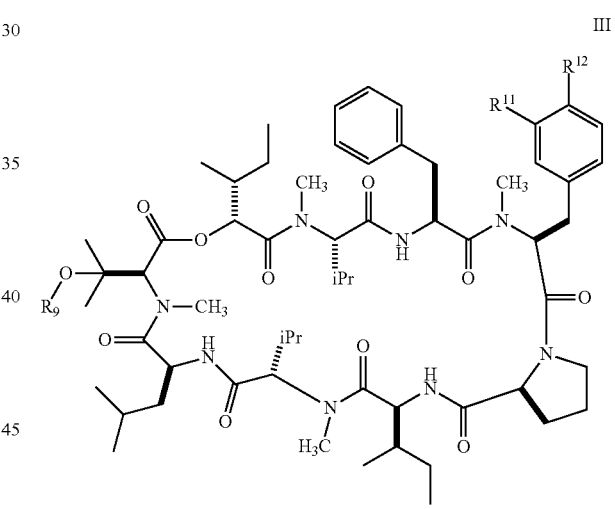

III or a pharmaceutically acceptable salt thereof, wherein one of R[11] and R[12] is —H, and the remainder is —I, —I, —Cl, —B(OH)$_2$,

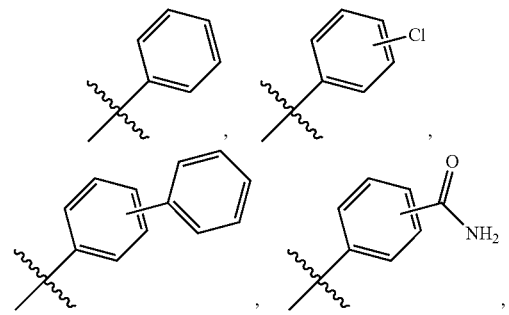

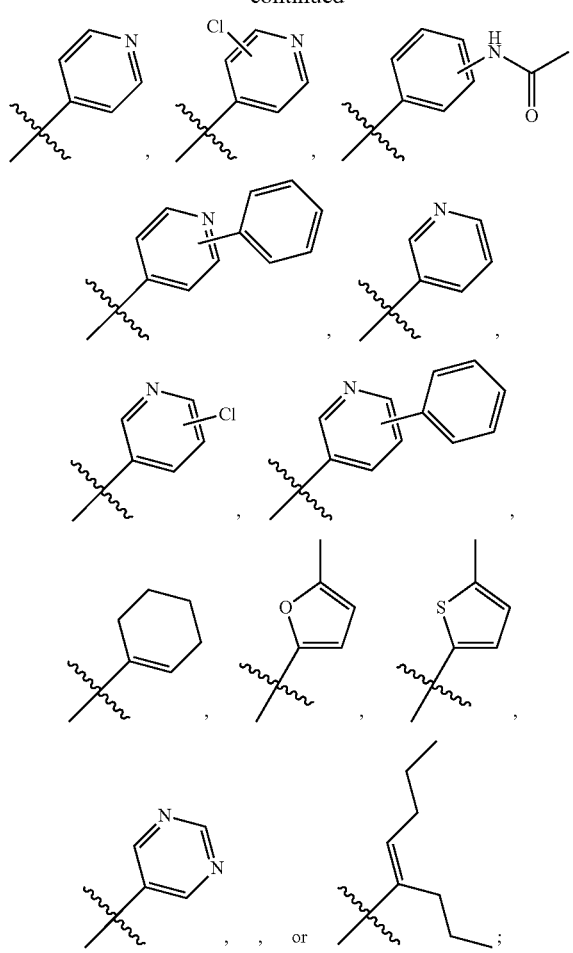

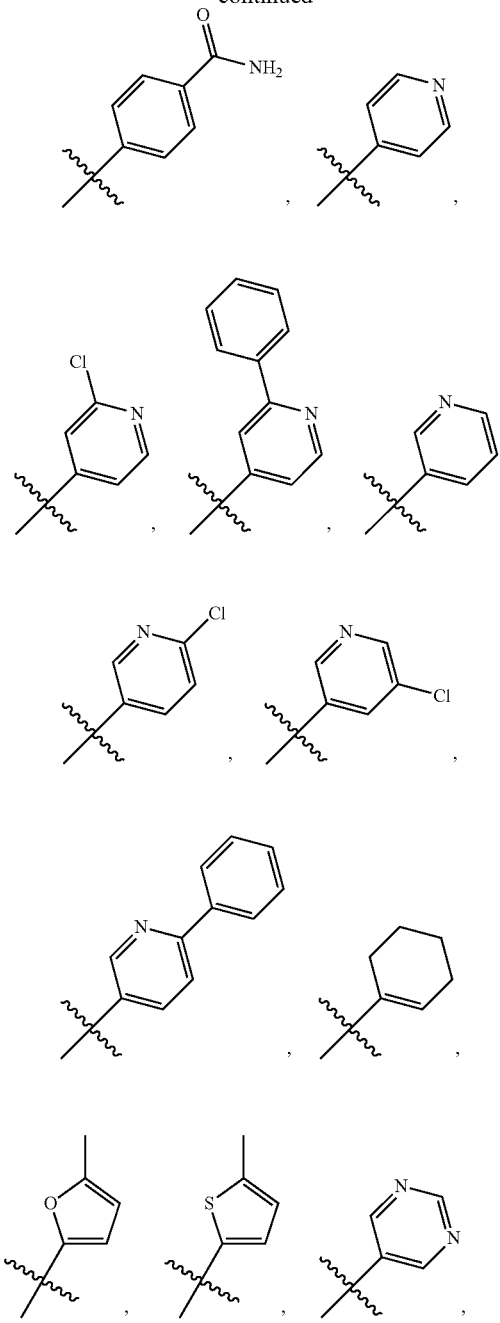

and $R^{13}$ is —H or —Si$(R^{10})_3$, wherein each $R^{10}$ is independently selected from an unsubstituted linear or branched $C_{1-6}$ alkyl; or pharmaceutically acceptable salt thereof, and a pharmaceutically acceptable vehicle, carrier, or adjuvant.

In some embodiments, one of $R^{11}$ and $R^{12}$ is —H, and the remainder is —I, —Cl, —Br, —B(OH)$_2$,

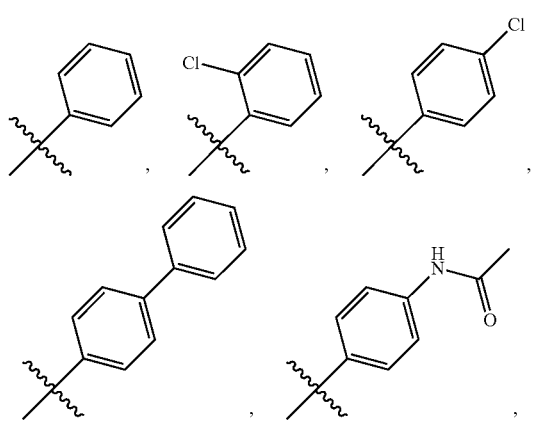

In some embodiments, $R^{12}$ is —H.

Another aspect of the present invention provides a pharmaceutical composition comprising a compound selected from

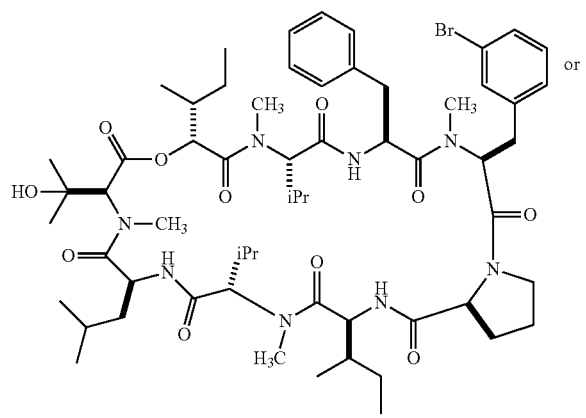

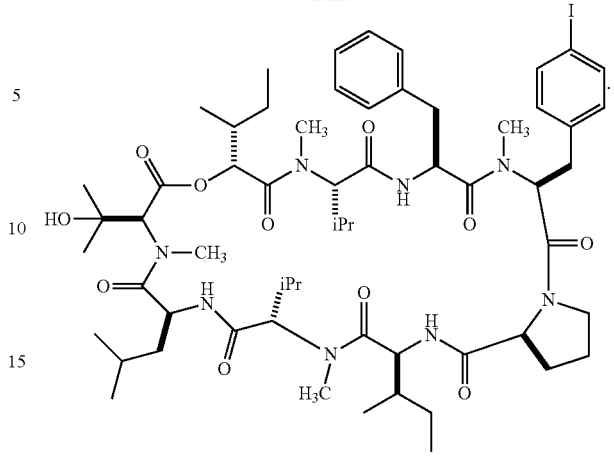

or a pharmaceutically acceptable salt thereof, and a pharmaceutically acceptable vehicle, carrier, or adjuvant.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion (e.g., spray dry dispersion) or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium

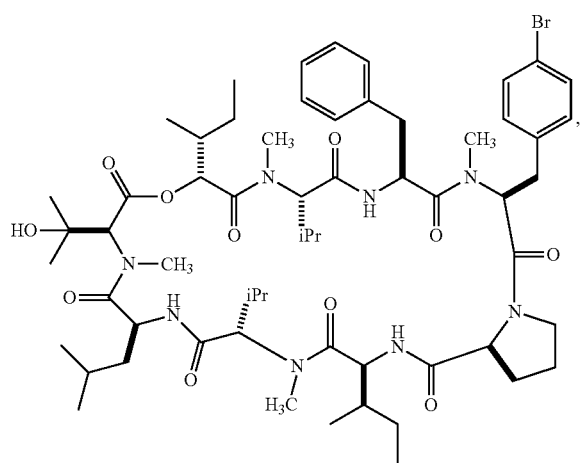

or a pharmaceutically acceptable salt thereof, and a pharmaceutically acceptable vehicle, carrier, or adjuvant.

Another aspect of the present invention provides a pharmaceutical composition comprising a compound selected from

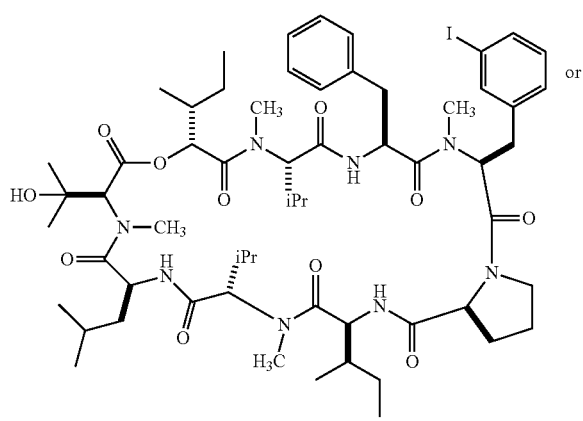

lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, the present invention provides a method of treating infection comprising administering one or more novel compounds, as described above, or a pharmaceutical composition comprising one or more of these novel compounds, preferably to a mammal, in need thereof.

According to the invention an "effective amount" of the compound or pharmaceutically acceptable composition is that amount effective for treating or lessening the severity of infection (e.g., a bacterial or fungal infection).

The pharmaceutical compositions, according to the present invention, may be administered using any amount and any route of administration effective for treating or lessening the severity of an infection.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors known in the medical arts. The term "patient", as used herein, means an animal, for example, a mammal, and more specifically a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect. Alternatively, the compounds of the invention may be administered orally or parenterally at dosage levels of between 10 mg/kg and about 120 mg/kg.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes: Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121, each of which is incorporated by reference. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

According to yet another embodiment, the present invention provides a method of treating or reducing the severity of infection.

Another aspect of the invention relates to treating infection in a biological sample or a patient (e.g., in vitro or in vivo), which method comprises administering to the patient, or contacting said biological sample with a pharmaceutical composition comprising a novel compound as described above. The term "biological sample", as used herein, includes, without limitation, cell cultures or extracts thereat biopsied material obtained from a mammal or extracts thereof; and blood, saliva, urine, feces, semen, tears, or other body fluids or extracts thereof.

In order that the invention described herein may be more fully understood, the following examples are set forth. It should be understood that these examples are for illustrative purposes only and are not to be construed as limiting this invention in any manner.

V. EXEMPLARY SYNTHESES

The compounds of Formula I and Ia may be readily synthesized from commercially available or known starting materials according to exemplary synthetic routes provided in the Schemes below.

In Scheme 1, AbA undergoes sequential borylation and halogenation to generate a compound of Formula I, which may include a mixture of compounds of Formula Ia1, Ia2, Ia3, Ia4, or any combination thereof. One example of this presented in Schemes 1a and 1b:

Scheme 1:

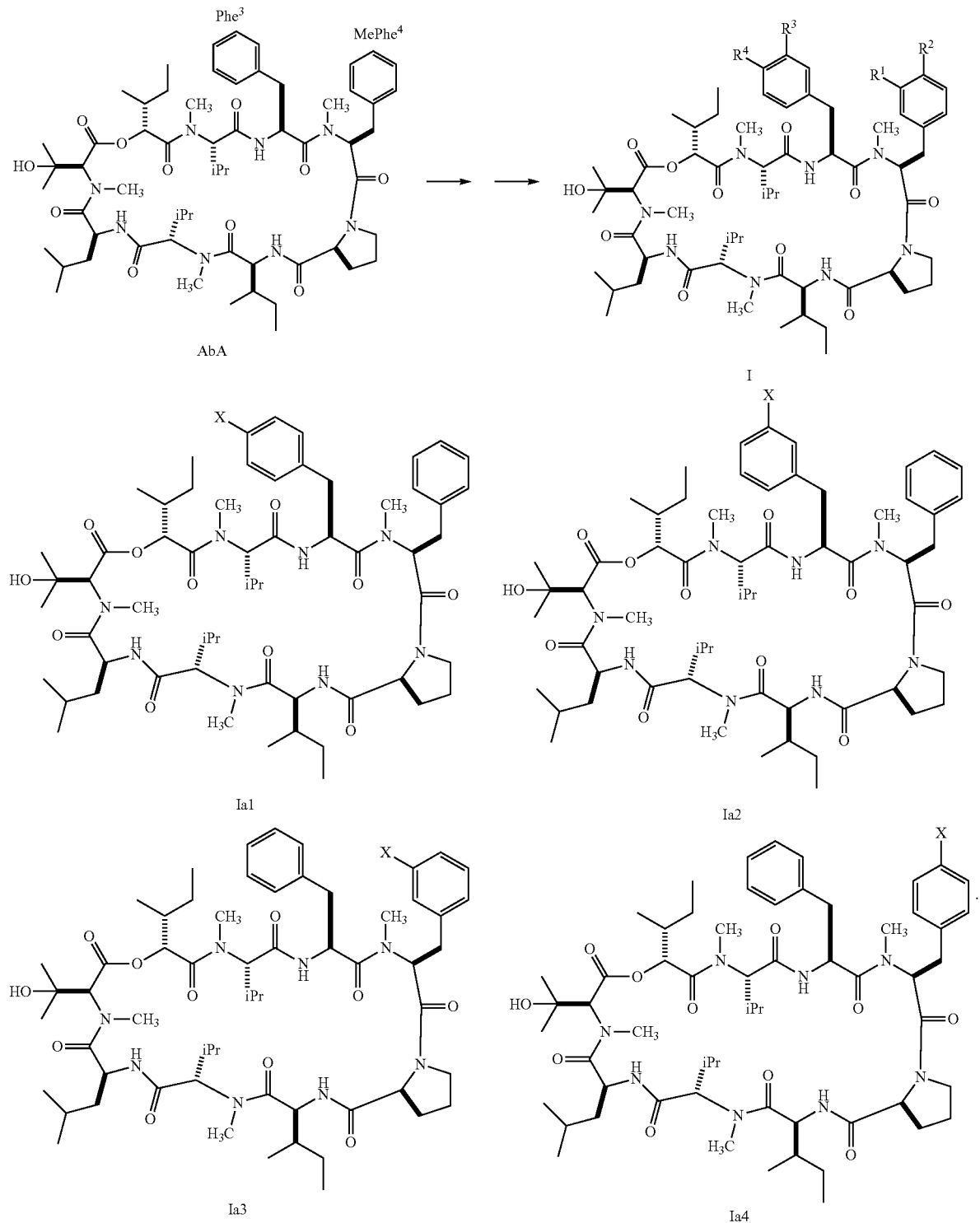

Scheme 1a:
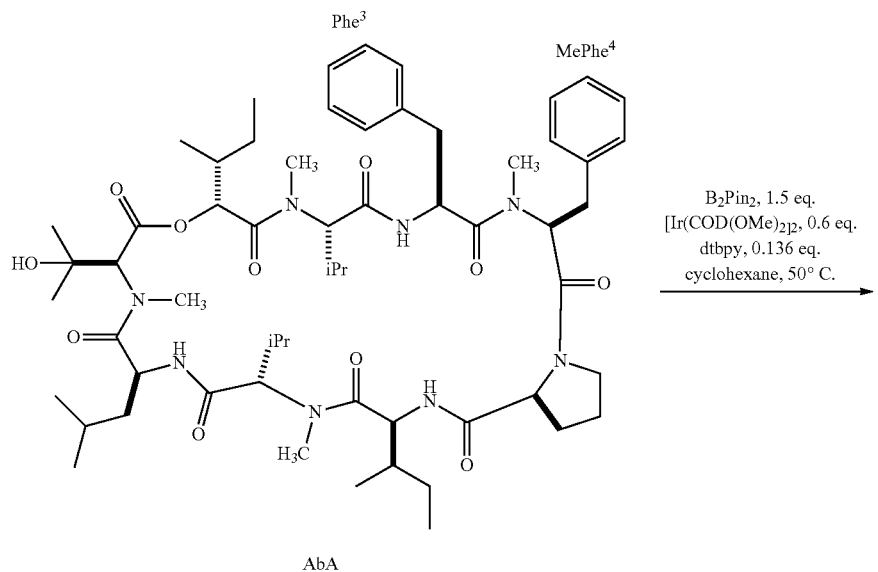
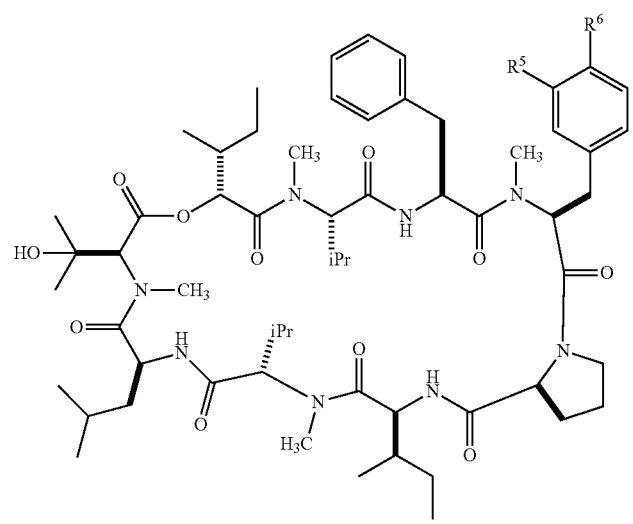

Scheme 1b:
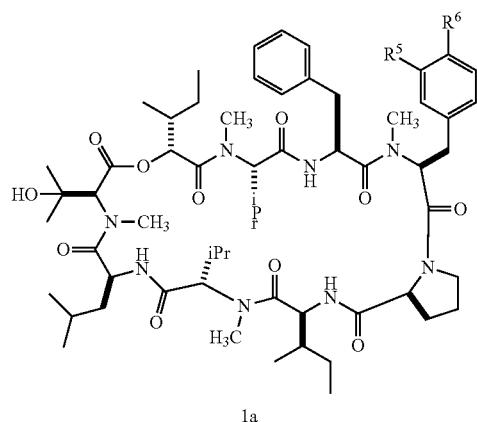
Ia
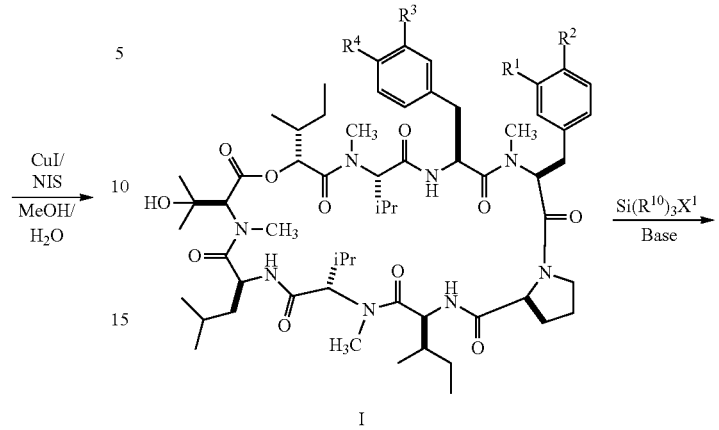
Scheme 2
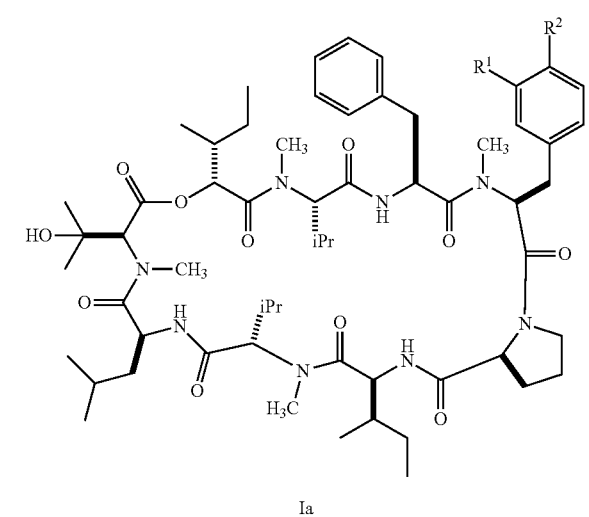
Ia
II
In Scheme 2, an alcohol moiety on halogenated AbA is protected by forming the silyl ether of compound II, wherein $R^1$-$R^4$, $R^9$, $R^{10}$, and $X^1$ are defined above.
Scheme 3 presents an exemplary synthetic route for further elaborating a halogenated AbA.

Scheme 3:

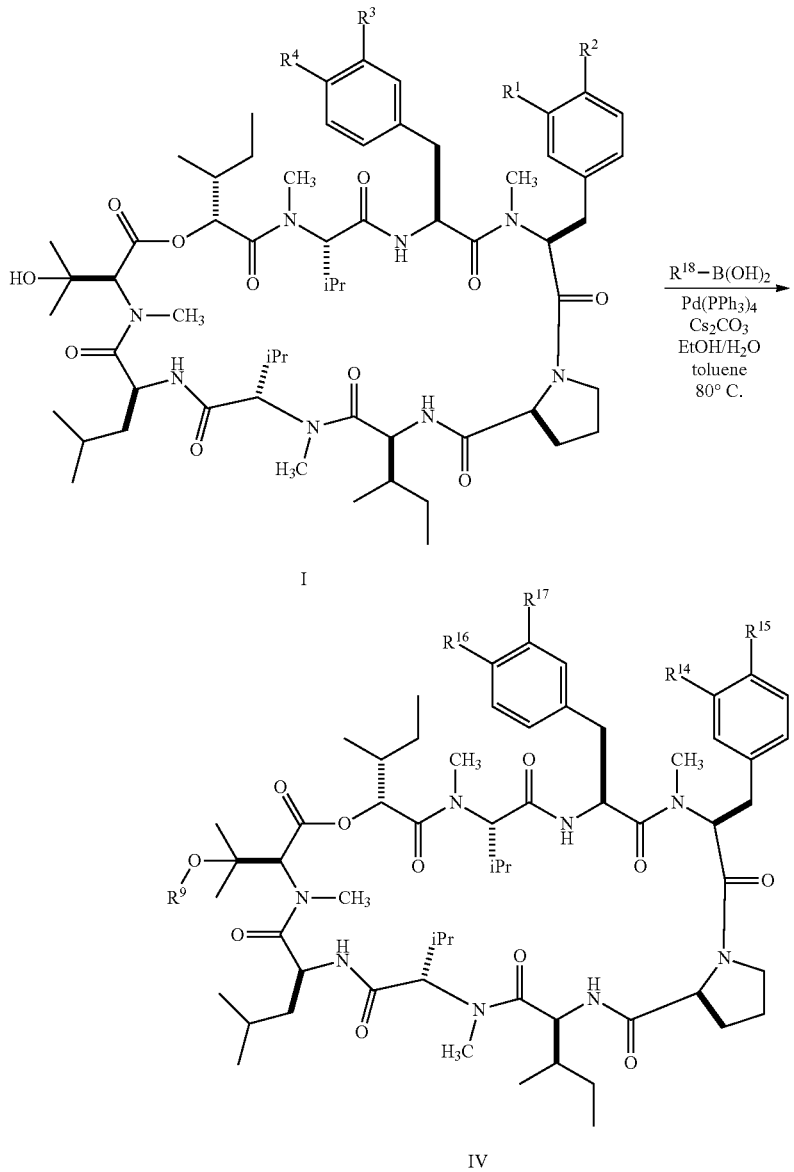

The AbA boronate may also be coupled with a variety of boronic acids to give desired adducts. This method is less considered to be less efficient, because typically an excess of the boronic acid is used in the Suzuki reaction. Therefore, from a material throughput and cost perspective, it is better to convert the boronate to the halide and use an excess of the low cost boronic acids in the coupling reaction.

VI. EXAMPLES

In order that the invention described herein may be more fully understood, the following examples are set forth. It should be understood that these examples are for illustrative purposes only and are not to be construed as limiting this invention in any manner.

Exemplary Syntheses

Example No. 1

Halogenated AbA

Aureobasidin Boronate—
4,4'-di-tert-butyl-2,2'-bipyridine (43.7 mg, 0.163 mmol) aureobasidin (0.50 g, 0.45 mmol), bis(pinacolato)diboron (0.181 g, 0.713 mmol) and 6 mL 1:1 mix of dry MTBE and heptane (argon sparged) were added to a dry 50 mL 3-necked flask that had been flushed with argon. The mixture was sparged with argon for 10 min. di-mu-methoxybis(1,5-cyclooctadiene)diiridium(I) (54 mg, 0.082 mmol) was added to the reaction and the reaction was heated to 70° C. At approximately 50° C., the reaction color turned red and after about 15 min at 70° C., the color changed to brown. The reaction was checked by HPLC after 30 min and determined to be 70% complete. The reaction was allowed to stir at 70° C. overnight. The reaction mixture was cooled to room temperature and diluted with dichloromethane. The mixture was filtered through magnesol (20 g) and flushed through with 200 mL of 25% acetone in dichloromethane. The solvent was removed en vacuo and the crude material was purified by silica gel chromatography (120 g) using 20-25% acetone in hexanes as the elutant. 195 mg (35%) the desired product was isolated as a white solid. HPLC retention time 6.674 min.

Aureobasidin Bromide—

Aureobasidin boronate (0.35 g, 0.28 mmol) was dissolved in methanol (6 mL) at room temperature in a 40 mL vial. The mixture was treated with a solution of copper(II) bromide (0.191 g, 0.855 mmol) in water (3 mL) and heated to 70° C. overnight. The pale blue solution was diluted with ethyl acetate (50 mL) and water (10 mL). The layers were separated and washed with brine. The organic layer was dried over anhydrous sodium sulfate, filtered and concentrated. The crude material was purified by silica gel chromatography (90 g) using 25% acetone in hexane as the elutant. The fractions containing the product were combined and concentrated to give 290 mg (86%) of the desired product as a white solid.

HPLC retention time 6.321 min. MS (ESI+) for $C_{60}H_{91}BrN_8O_{11}$ m/z 1179.6, 1181.6 (M+H)+.

Aureobasidin Iodide—

Aureobasidin MePhe boronate (8.2 g, 3.3 mmol) was dissolved in methanol (35 mL, 880 mmol) and water (3.5 mL, 2.0E2 mmol) at room temperature and treated with copper(I) iodide (1.19 g, 6.26 mmol) and N-iodosuccinimide (1.41 g, 6.26 mmol) and heated to 80° C. for 5 h at which point HPLC shows complete reaction. The heat was turned off and the mixture was filtered through solka floc the next day and the product isolated with MTBE from aqueous sodium bisulfite. The solution was dried over $MgSO_4$, filtered and concentrated to a foam. The crude product was used directly in Suzuki reactions described in Example No. 2, below.

Example No. 2

Elaboration of Halogenated AbA

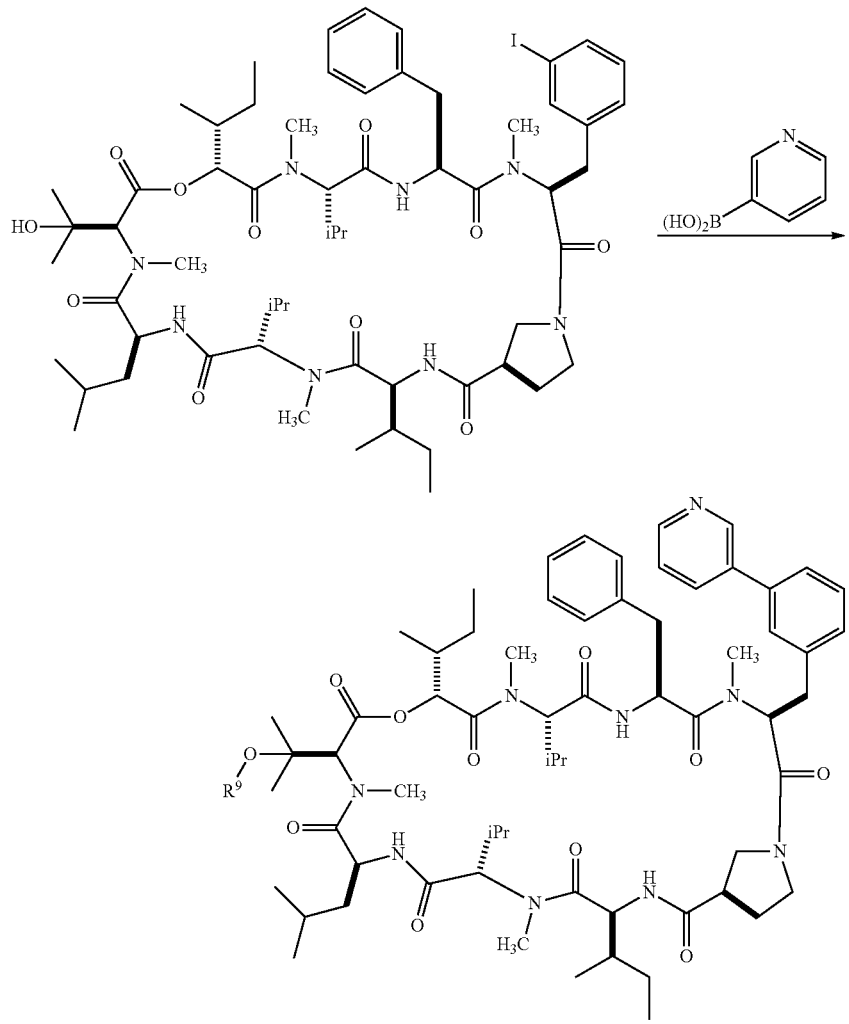

Iodated AbA was elaborated to generate a 3-pyridyl-mPhe[4]-AbA following the reaction conditions provided in Table 1:

TABLE 1

Reaction conditions for generating pyridine-3-yl-AbA.

| Conditions | Yield (%) |
|---|---|
| 3-Pyridylboronic acid, K₂CO₃, Pd₂(dba)₃, S-Phos, dioxane/water, 90° C., o/n. | ~32 |
| 3-Pyridylboronic acid, K₂CO₃, Pd₂(dba)₃, tri(tert-butylphosphonium) tetrafluoroborate, dioxane/water, 90° C., o/n. | ~43 |
| 3-Pyridylboronic acid, K₂CO₃, PdCl₂(dppf), dioxane/water, 90° C., o/n. | ~40 |
| 3-Pyridylboronic acid, Cs₂CO₃, Pd(PPh₃)₄, EtOH, toluene/water, 90° C., o/n. | N/A |

The reactions were performed using 0.025 g of starting material, and the yields were determined via HPLC analysis.

Analytical Techniques

Example No. 3

Hydrolysis of AbA-Br 12M hydrochloric acid (0.6 mL) and trifluoroacetic acid (0.2 mL) were added to a microwave reaction vessel containing Aureobasidin A bromide (20 m g, 0.02 mmol). The mixture was heated in the microwave for 25 min at 145° C. (maximum pressure 200 psi). The mixture was allowed to cool to room temperature and analyzed by mass spectroscopy, as described below. The pH of the entire mixture was adjusted to 12 with 30% potassium hydroxide. Acetic anhydride (0.031 mL, 0.33 mmol, 20 eq.) was added to the mixture and the pH was re-adjusted to 12 with additional 30% potassium hydroxide. After 30 min, the mixture was assayed by mass spectroscopy and HPLC. All of the brominated amino acid products were converted to their corresponding acetamides. Referring to FIG. 1, the HPLC data indicated that the brominated product was a mixture of four compounds. The composition of the mixture was 62% N-acetyl-3-bromo-N-methylphenylalanine (13.370 min), 27% N-acetyl-4-bromo-N-methylphenylalanine (14.364 min), 9% N-acetyl-3-bromophenylalanine (7.967 min) and 2% N-acetyl-4-bromophenylalanine (8.492 min). These results were based on synthesized standards and calculation of response factors of a known mixture of the standards.

HPLC Conditions:

Agilent 1100 HPLC; Eclipse XDB-C18 50×4.6 mm 1.8 micron column; Gradient—5 min 95% water (0.10% TFA) to 95% acetonitrile (0.07% TFA); 1.5 mL/min; UV Detection @ 210 nm.

Example 4

Mass Spectroscopy

Figure 2:
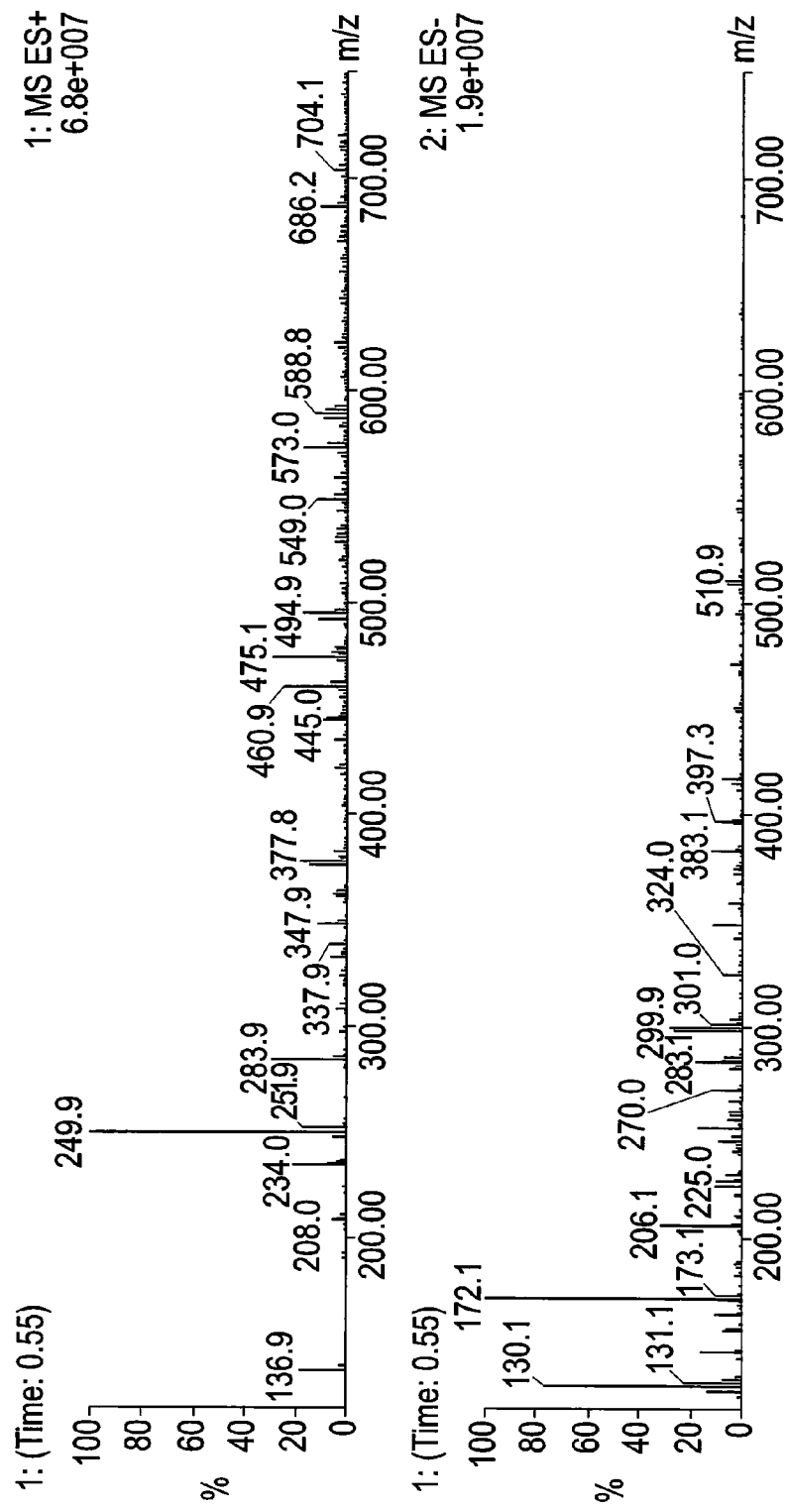
FIG. 2 presents a mass spectrum for exemplary reaction products in accordance with one aspect of the present invention.

Referring to FIG. 2, MS-MS analysis of the brominated AbA generated number of fragments. The analysis focused on fragments containing the isotopic bromine signature, i.e., fragments that show the two mass units split into two peaks of about equal abundancy, reflecting the about 50:50 abundancy of the two natural isotopes, $^{79}$Br and $^{81}$Br. Such fragments are relevant because they contain the brominated amino acid. Fragments that are brominated and also generated by a split between Phe³ and mPhe⁴ are diagnostic of which of the two amino acids in the AbA-Br are substituted. To simplify the analysis only fragments generated by cleavage of the peptide bonds without any additional degradation of the peptide structure were studied. Three such fragments were unequivocally identified.

Thus the major AbA bromination product (89%) is substituted on mPhe⁴, essentially randomly at the meta and para positions (2:1 ratio). No 2-Br-mPhe-Ac compound was detected.

About 11% of the AbA bromination product was substituted on Phe³, again essentially randomly at the meta and para positions (2:1 ratio). And, again no 2-Br-Phe-Ac compound (i.e. substitution in the ortho position) was detected.

Example 5

¹H NMR Mass Spectroscopy

Figure 3:
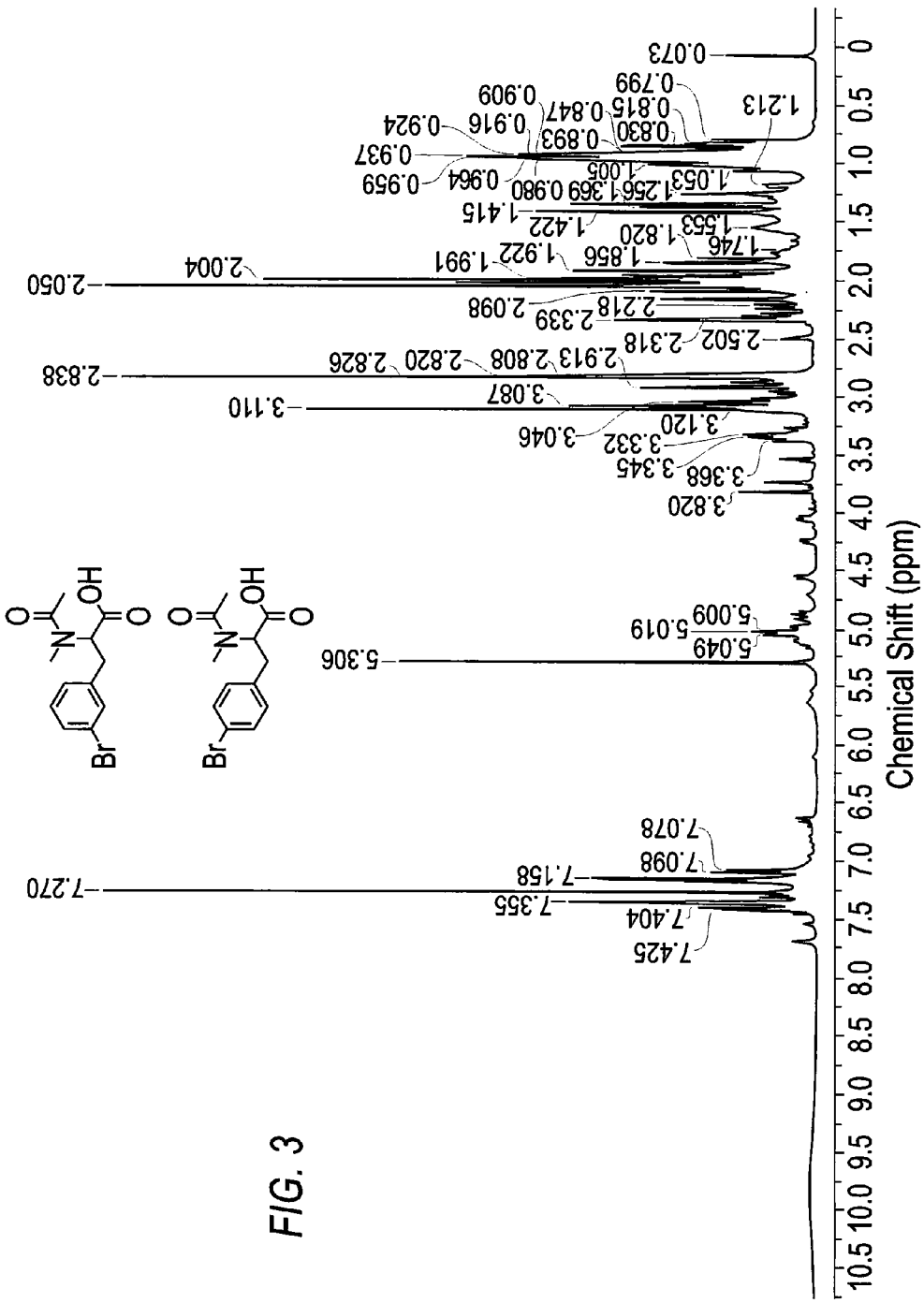
FIG. 3 presents an $^1$H NMR spectrum for exemplary acetamide fragments of reaction products in accordance with one aspect of the present invention.
Figure 4:
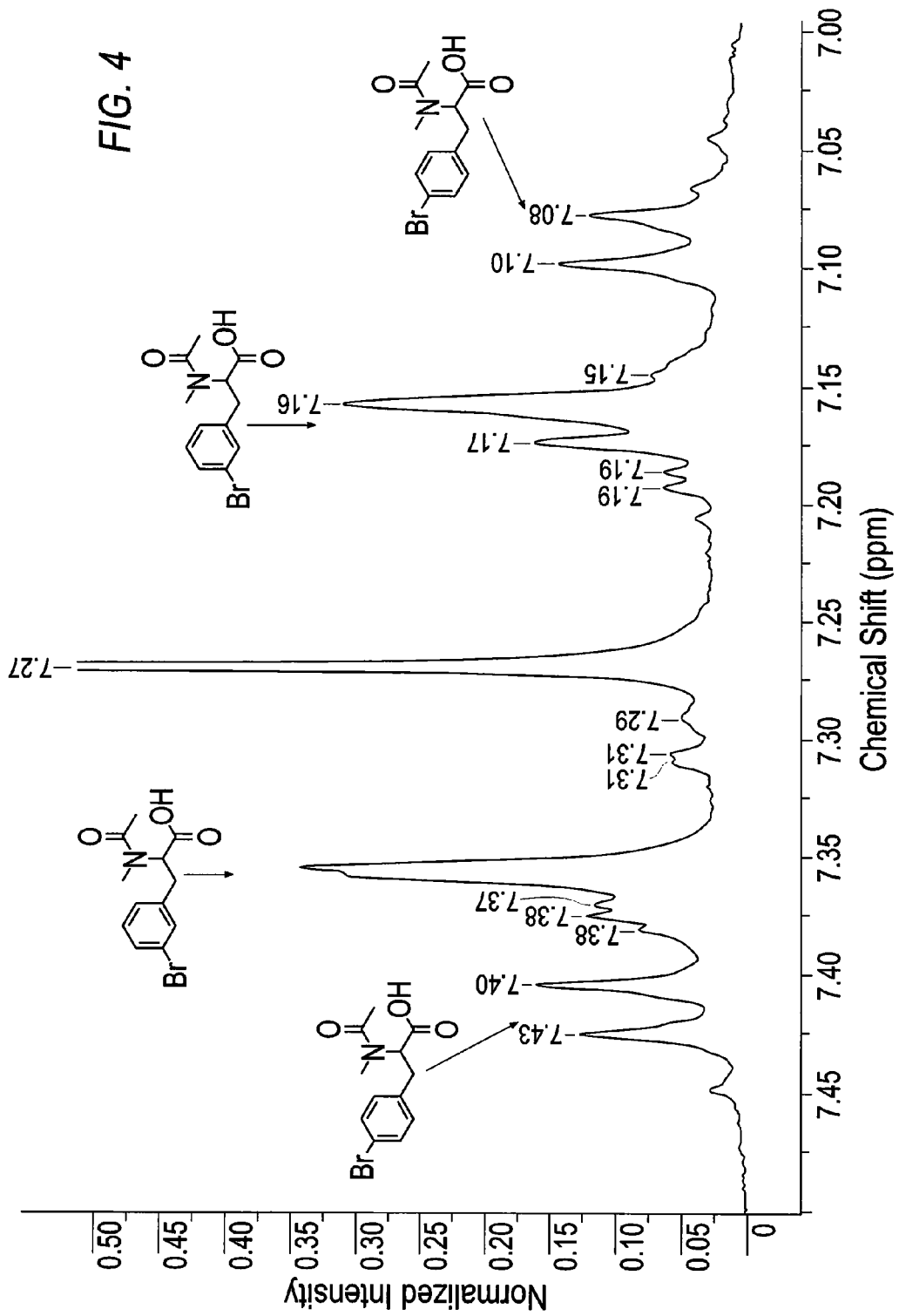
FIG. 4 presents a normalized $^1$H NMR spectrum for exemplary acetamide fragments of reaction products in accordance with one aspect of the present invention.

Referring to FIGS. 3 and 4, acetamides of the reaction products underwent ¹H NMR analysis using deuterated chloroform as the solvent.

Example 6

MIC-Studies

The activities of several exemplary compounds of the present invention were assayed according to the CLSI standard M38-A2 titled "Reference Method for Broth Dilution Antifungal Susceptibility Testing of Filamentous Fungi". However, the RPMI-1640 broth is substituted for a YPD medium formulated according to the following steps:

1. Dissolve 10 g of BactoYeast extract in 500 ml water
2. Dissolve 20 g of BactoPeptone in the above solution
3. Dissolve 20 g Dextrose in the above solution*

*Ordinary table sugar (sucrose) substituted for dextrose routinely.

4. q.s. to 1000 ml with water
5. Autoclave

The results of this study are provided in Tables 2 and 3, below.

TABLE 2

MICs for AbA-derivatives.

| Compound | MIC for C. albicans (ug/ml) | MIC for A. fumigatus (pg/ml) |
|---|---|---|
| AbA (native) | <0.05 | >25 |
| Boronate-mPhe⁴-AbA | <0.5 | 10 |
| Br-mPhe⁴-AbA | 0.031 | 2.5 |
| MeO-φ-mPhe⁴-AbA | 5 | N/A |
| B(OH)₂-mPhe⁴-AbA | <0.05 | >100 |
| Asp³-Br-mPhe⁴-AbA | 5 | 10 |
| Br-Phe³-Br-mPhe⁴-AbA | 5 | >100 |
| Asp³-mAsp⁴-AbA | 10 | >100 |
| I-mPhe⁴-AbA | 2.5 | >5 |
| Phenyl-mPhe⁴-AbA | <0.05 | <0.94 |
| 5-methyl-furanyl-mPhe⁴-AbA | N/A | >5 |
| 4-N-methylaminocarboxyphenyl-mPhe⁴-AbA | N/A | >5 |
| 5-methylthiophenyl-mPhe⁴-AbA | N/A | >5 |
| 5-pyrimidyl-mPhe⁴-AbA | N/A | >5 |
| 3-pyridyl-mPhe⁴-AbA | <0.05 | <0.94 |
| Cyclohexenyl-mPhe⁴-AbA | N/A | >5 |
| 4-acetamidophenyl-mPhe⁴-AbA | N/A | >5 |
| Cl-mPhe⁴-AbA | N/A | >5 |
| Octene--mPhe⁴-AbA | N/A | >5 |
| 2-Cl-Phenyl-mPhe⁴-AbA | N/A | <1.25 |
| 4-Cl-Phenyl-mPhe⁴-AbA | N/A | <2.5 |
| 4-pyridyl-mPhe⁴-AbA | N/A | <1.25 |
| 3-biphenyl-mPhe⁴-AbA | N/A | >5 |

TABLE 2-continued

MICs for AbA-derivatives.

| Compound | MIC for C. albicans (ug/ml) | MIC for A. fumigatus (pg/ml) |
|---|---|---|
| 4-biphenyl-mPhe$^4$-AbA | N/A | >5 |
| 2-chloropyridin-5-yl-mPhe$^4$-AbA | N/A | >1.25 |

Table 3, below, demonstrates the broad-spectrum antifungal activity for the AbA derivative 3-pyridyl-mPhe$^4$-AbA, as determined according to the procedures described above.

TABLE 3

Antifungal activity of 3-pyridyl-mPhe$^4$-AbA.

| Organism | MIC for 3-pyridyl-mPhe$^4$-AbA (μg/ml) 48 hr reading 72 hr reading | MIC for Amphotericin (μg/ml) 48 hr reading 72 hr reading |
|---|---|---|
| Aspergillus amstelodami 641 (ATCC16464) | No growth at 96 hrs | No growth at 96 hrs |
| Aspergillus fumigatus 891 (ATCC204305) | 1 / 2 | 0.25 / 1 |
| Aspergillus flavus 4787 (ATCC204304) | 1 / 2 | 0.25 / 0.25 |
| Aspergillus flavus 122 (ATCC22546) | 2 / 64 | 0.25 / 0.25 |
| Aspergillus flavus 626 (ATCC64025) | 1 / 2 | 0.5 / 0.5 |
| Aspergillus candidus 450 (ATCC13686) | 0.008 / 0.015 | 0.03 / 0.06 |
| Aspergillus clavatus 638 (ATCC10058) | 0.03 / 0.03 | ≤0.004 / 0.015 |
| Aspergillus niger 624 (ATCC16888) | 0.125 / 0.25 | 0.03 / 0.125 |
| Aspergillus ochraceus 625 (ATCC96919) | 0.25 / 0.5 | 0.25 / 0.5 |
| Emericella nidulans 637 (ATCC96921) | 0.125 / 0.25 | 1 / 2 |
| Fonsecaea pedrosoi 4784 (ATCC10221) | No growth at 96 hrs | No growth at 96 hrs |
| Fusarium oxysporum 0893 (ATCC48112) | >64 at 96 hr | 1 at 96 hr |
| Madurella grisea 4786 (ATCC10794) | N/A | N/A |
| Phialophora verrucosa 4785 (ATCC10223) | No growth at 96 hrs | No growth at 96 hrs |
| Rhizopus oryzae 0890 (ATCC11886) | >64 / >64 | 0.03 / 0.03 |
| Sporothrix schenkii 892 (ATCC14284) | >64 at 96 hrs | 0.5 at 96 hrs |
| Trychophyton mentagrophytes 5278 (ATCC MYA-4439) | 0.5 at 96 hrs | 0.06 at 96 hrs |
| Trychophyton mentagrophytes 640 (ATCC 28185) | 1 / 1 | 0.06 / 0.25 |
| Trychophyton rubrum 5279 (ATCC MYA-4438) | 2 at 72 hrs | 0.03 at 72 hrs |
| Aspergillus fumigatus 5280 (ATCC MYA-3626) | 2 / 16 | 0.25 / 0.5 |
| Aspergillus fumigatus 5280 (ATCC MYA-3626) no Tween | 4 / 64 | 1 / 2 |
| Amphotericin B CLSI QC Range for A. Fumigatus ATCC MYA-3626 | | 0.5-4 at 48 hrs |
| Candida albicans 104 (ATCC90028) | 0.015 / 0.015 | 0.3 / 0.6 |
| Candida albicans 633 (ATCC90029) | 0.5 / 1 | 0.3 / 0.6 |
| Candida albicans 2000 (ATCC10231) | 1 / 1 | 0.3 / 0.6 |
| Candida albicans 2486 | 0.03 | 0.06 |
| (ATCC204276) | 0.03 | 0.06 |
| Candida albicans 2487 (ATCC MYA-2732) | 0.3 / 0.3 | 0.06 / 0.06 |
| Candida albicans 4782 (ATCC24433) | 0.125 / 0.25 | 0.3 / 0.6 |
| Candida guilliermondii 628 (ATCC34134) | 0.03 / 0.03 | 0.008 / 0.015 |
| Candida krusei 629 (ATCC14243) | 0.06 / 0.06 | 0.125 / 0.125 |
| Candida lusitaniae 631 (ATCC66035) | 0.125 / 0.25 | 0.015 / 0.03 |
| Candida parapsilosis 0630 (ATCC90018) | 0.03 / 0.03 | 0.06 / 0.125 |
| Candida glabrata 635 (ATCC90030) | 0.03 / 0.06 | 0.03 / 0.125 |
| Candida tropicalis 4783 (ATCC750) | 0.03 / 0.03 | 0.06 / 0.125 |
| Candida tropicalis 636 (ATCC90874) | 0.015 / 0.06 | 0.06 / 0.125 |
| Cryptococcus neoformans 0634 (ATCC90112) | 0.03 / 0.06 | 0.015 / 0.03 |
| Issatchenkia orientalis 2322 (ATCC6258) | 0.06 / 0.06 | 0.125 / 0.125 |
| Saccharomyces cerevisiae 0639 (ATCC7754) | 0.03 / 0.06 | 0.06 / 0.06 |
| Candida parapsilosis 2323 (ATCC22019) | 0.06 / 0.06 | 0.125 / 0.125 |
| Candida parapsilosis 2323 (ATCC22019) no Tween | 0.5 / 0.5 | 0.25 / 1 |
| Amphotericin B CLSI QC Range for C. parapsilosis | | 0.25-2 (24 hrs) 0.5-4 (48 hrs) |

Note that the AbA compounds used to generate the MIC data in Tables 2 and 3 had a purity of ~85%.

Example 7

Pharmacokinetic Studies of 3-pyridyl-mPhe$^4$-AbA

Figure 5:
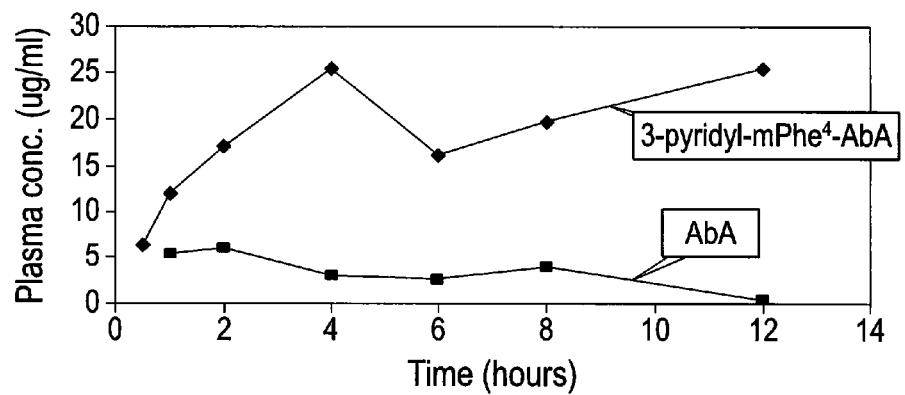
FIG. 5 presents blood plasma concentrations of AbA and an AbA derivative as a function of time in a mouse model.

Referring to FIG. 5, mice were administered a single 200 mg/kg bolus dose of 3-pyridyl-mPhe$^4$-AbA (diamonds) or AbA (squares), by oral gavage. Blood was collected a timed intervals after administration of the drug and analyzed for compound content by HPLC-MS.

An evaluation of 3-pyridyl-mPhe$^4$-AbA's pharmacokinetic (PK) properties in mice revealed that oral administration of 200 mg/kg of the compound generated significantly higher plasma concentrations than the same dose, also administered orally, in the same vehicle, of native AbA. Moreover, the 3-pyridyl-mPhe$^4$-AbA plasma concentration, at the end of the 12 hour experiment appears not to be decreasing as is does for native AbA, but rather to still be increasing. This demonstrates an enhanced bioavailability and/or a slower clearance of 3-pyridyl-mPhe$^4$-AbA, as compared to the native drug. The experiment also shows that, A. fumigatus therapeutic concentrations, in mice, may be achievable with a considerably smaller dose.

Figure 6:
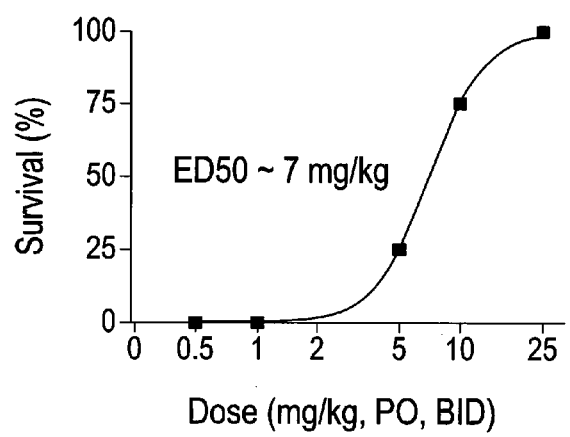
FIG. 6 presents mortality as a function of dose for an AbA derivative in a mouse model.

Referring to FIG. 6, Mice, immunosuppressed with cyclophosphamide, were inoculated with 8 log 10 CFU Candida albicans SC5413 and dosed (following inoculation) with 3-pyridyl-mPhe$^4$-AbA (or a control antibiotic) orally, BID, for four consecutive days. Efficacy was determined by enumerating mortality. The ED50 of native AbA, in this Candidiasis model, was about 25 mg/kg, i.e. almost four times higher that of 3-pyridyl-mPhe⁴-AbA.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of generating a compound of Formula I

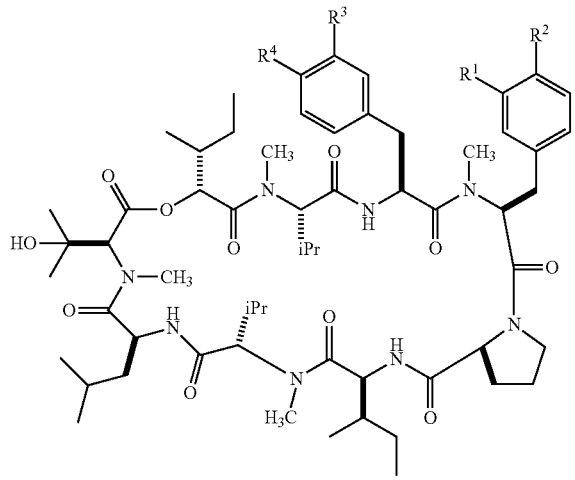

wherein one of $R^1$, $R^2$, $R^3$, or $R^4$ is —X, and the remainder are —H, wherein X is a halogen; comprising:

reacting a compound of Formula V with a halogenating reagent in the presence of a first solvent to form the compound of Formula I

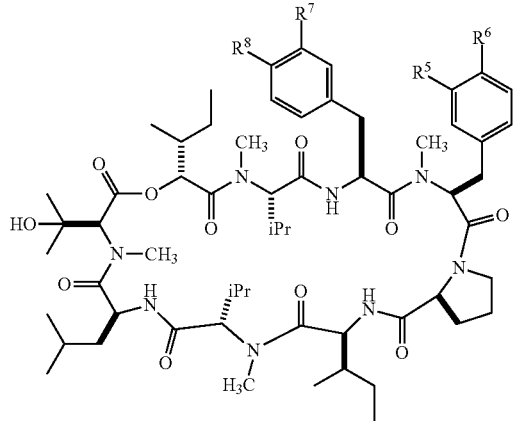

wherein one of $R^5$, $R^6$, $R^7$, or $R^8$ is

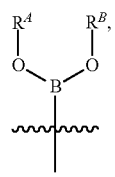

and the remainder are —H; and each of $R^A$ and $R^B$ are independently —$C_{1-4}$ alkyl, —$C_{3-6}$ cycloalkyl; or $R^A$ and $R^B$ together with the oxygen atoms to which they are attached form a 5-6 membered ring optionally substituted with 1-4 of —$C_{1-3}$ alkyl, —$C_{1-3}$ alkoxycarbonyl, —$C_{1-3}$ alkylaminocarbonyl, or any combination thereof; or $R^A$ and $R^B$ together with the oxygen atoms to which they are attached form a 7-10 membered bicyclic or tricyclic ring optionally substituted with 1-4 of —$C_{1-3}$ alkyl, —$C_{1-3}$ alkoxycarbonyl, —$C_{1-3}$ alkylaminocarbonyl, or any combination thereof.

2. The method of claim 1, further comprising reacting a compound of Formula 2

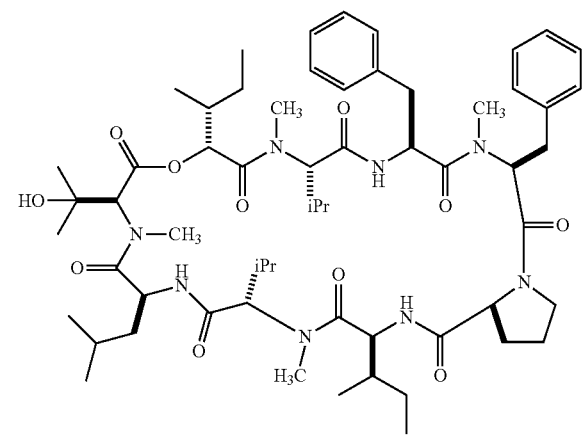

with a borylating reagent in the presence of a catalyst and a second solvent to generate a compound of Formula V.

3. The method of claim 1, wherein —X is selected from —Cl, —Br, or —I.

4. The method of claim 1, wherein the halogenating reagent comprises copper(II)halide.

5. The method of claim 2, wherein the borylating reagent is selected from 4,4,5,5-tetramethyl-1,3,2-dioxaborolane, catecholborane, bis(neopentyl glycolato)diboron, bis(pinacolato)diboron, bis(hexylene glycolato)diboron, bis(catecholato)diboron, bis[(+)-pinanediolato]diboron, bis[(−)-pinanediolato]diboron, bis(diethyl-D-tartrate glycolato)diboron, bis(diethyl-L-tartrate glycolato)dibhron, bis(diisopropyl-D-tartrate glycolato)diboron, bis(diisopropyl-L-tartrateglycolato)diboron, bis(N,N,N',N'-tetramethyl-D-tartaramideglycolato)diboron, bis(N,N,N',N'-tetramethyl-L-tartaramideglycolato)diboron, or any combination thereof.

6. The method of claim 2, wherein the transition metal catalyst is a catalyst selected from an Ir catalyst, a Re catalyst, a Rh catalyst, a Pd catalyst, a Pt catalyst, a Ni catalyst, or any combination thereof.

7. A method of generating a compound of Formula Ia

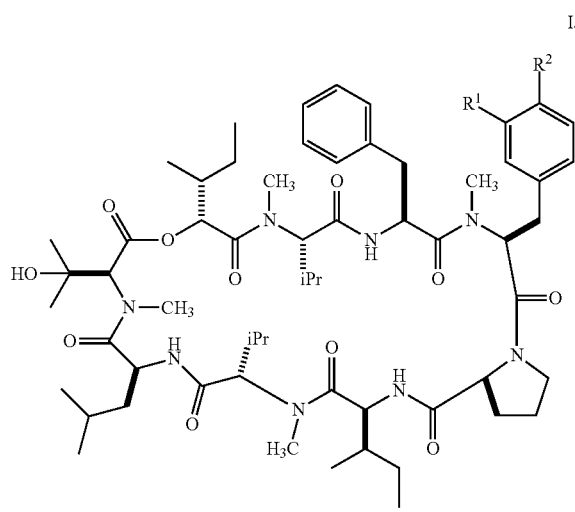

wherein one of $R^1$ or $R^2$ is —Br or —I, and the remainder is —H, comprising:

reacting a compound of Formula Va with a brominating reagent or iodinating reagent in the presence of a first solvent to form a compound of Formula Ia

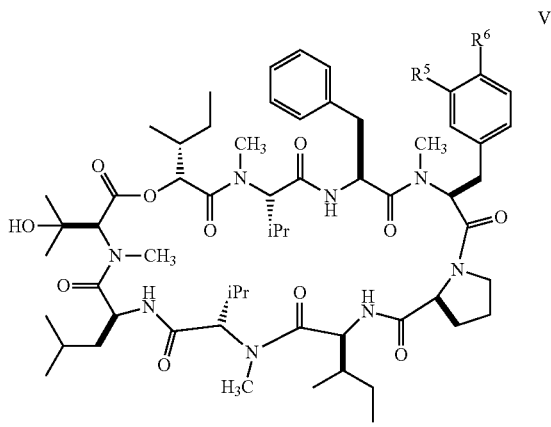

wherein one of $R^5$ or $R^6$ is

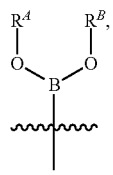

and the remainder is —H; and each of $R^A$ and $R^B$ are independently —$C_{1-4}$ alkyl, —$C_{1-4}$ cycloalkyl; or $R^A$ and $R^B$ together with the oxygen atoms to which they are attached form a 5-6 membered ring optionally substituted with 1-4 of —$C_{1-3}$ alkyl, —$C_{1-3}$ alkoxycarbonyl, —$C_{1-3}$ alkylaminocarbonyl, or any combination thereof; or $R^A$ and $R^B$ together with the oxygen atoms to which they are attached form a 7-10 membered bicyclic or tricyclic ring optionally substituted with 1-4 of —$C_{1-3}$ alkyl, —$C_{1-3}$ alkoxycarbonyl, —$C_{1-3}$ alkylaminocarbonyl, or any combination thereof.

8. The method of claim 7, further comprising reacting a compound of Formula 2

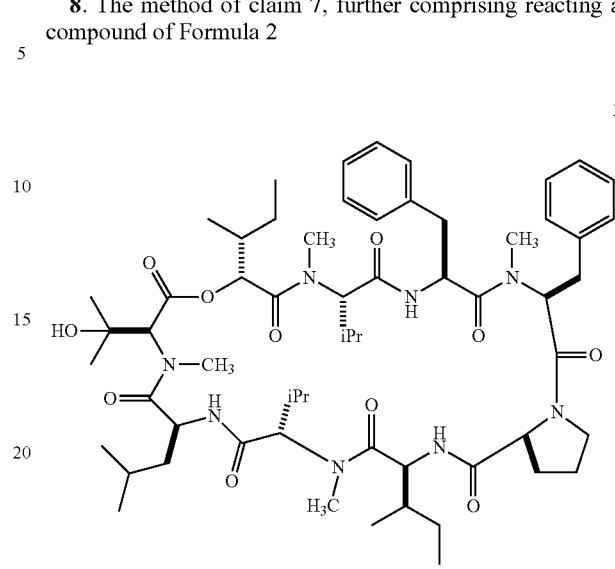

with a borylating reagent in the presence of a catalyst and a second solvent to generate a compound of Formula Va.

9. The method of claim 7, wherein the compound of Formula Ia is

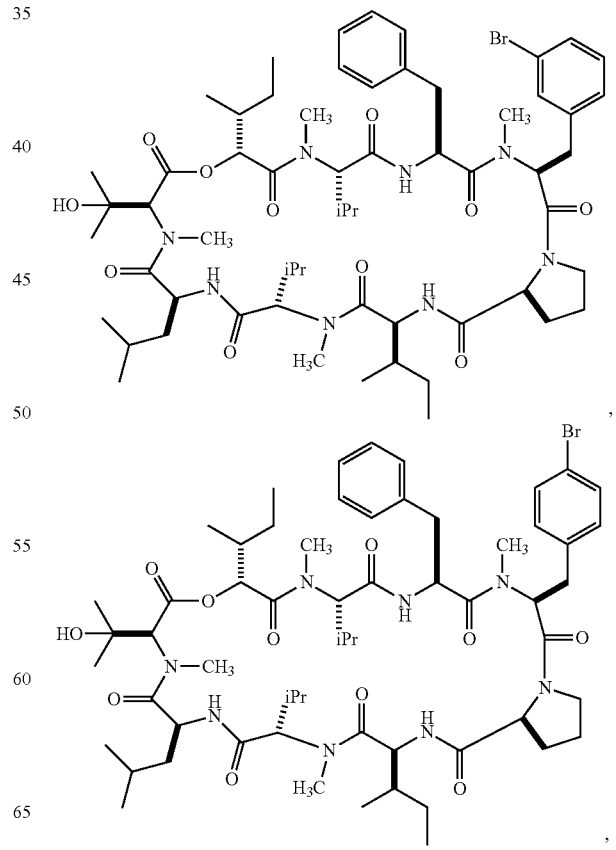

-continued

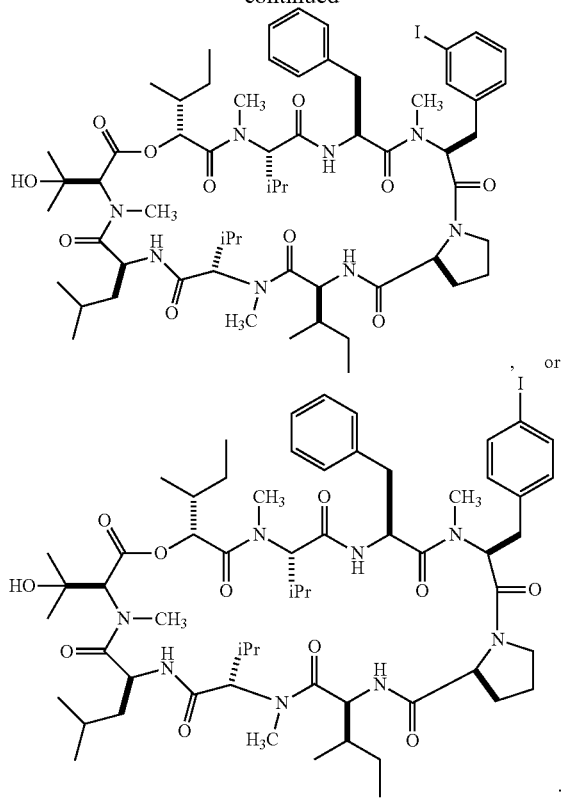

, or

10. The method of claim 7, wherein the brominating reagent is selected from copper(II)bromide or the iodinating reagent is selected from copper(II)iodide.

11. The method of claim 8, wherein one of $R^5$ or $R^6$ is

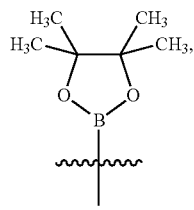

and the remainder is —H.

12. The method of claim 8, wherein the borylating reagent is selected from bis(pinacolato)diboron, bis(neopentylglycolato)diboron, 1,3,2-dioxaborolane, 4,5-dimethyl-1,3,2-dioxaborolane, bis(N,N,N',N',N'-tetramethyl-L-tartaramide glycolato)diboron, bis(diethyl-D-tartrate glycolato)diboron, bis(diethyl-L-tartrate glycolato)diboron, bis(diisopropyl-D-tartrate glycolato)diboron, bis[(+)-pinanediolato]diboron, or any combination thereof.

13. The method of claim 8, wherein the transition metal catalyst is a catalyst selected from an Ir catalyst, a Re catalyst, a Rh catalyst, a Pd catalyst, a Pt catalyst, a Ni catalyst, or any combination thereof.

14. A method of generating a compound of Formula IV

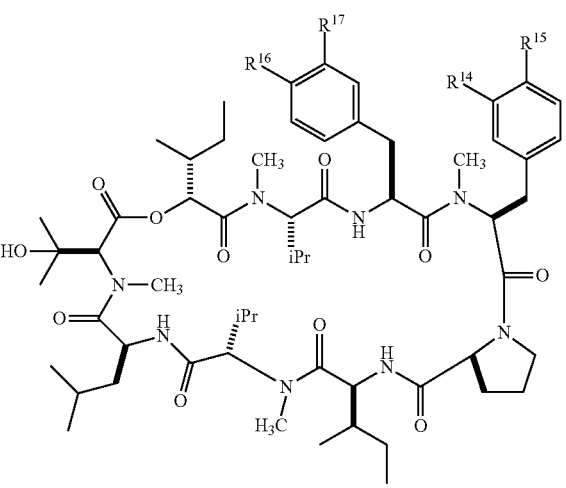

wherein
one of $R^{14}$, $R^{15}$, $R^{16}$, or $R^{17}$ is optionally substituted aryl or optionally substituted heteroaryl, and the remainder are —H, comprising:
reacting a compound of Formula I

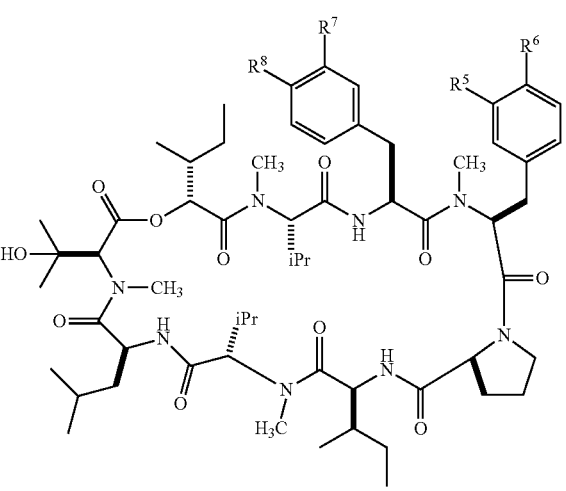

wherein one of $R^1$, $R^2$, $R^3$, or $R^4$ is —X, and the remainder are —H, and X is a halogen, with $R^{18}$—B(OH)$_2$, in the presence of a catalyst comprising Pd, wherein $R^{18}$ is an aryl or heteroaryl that is optionally substituted with one or more additional moieties.

15. The method of claim 14, wherein the compound of Formula IV is a compound of Formula IVA

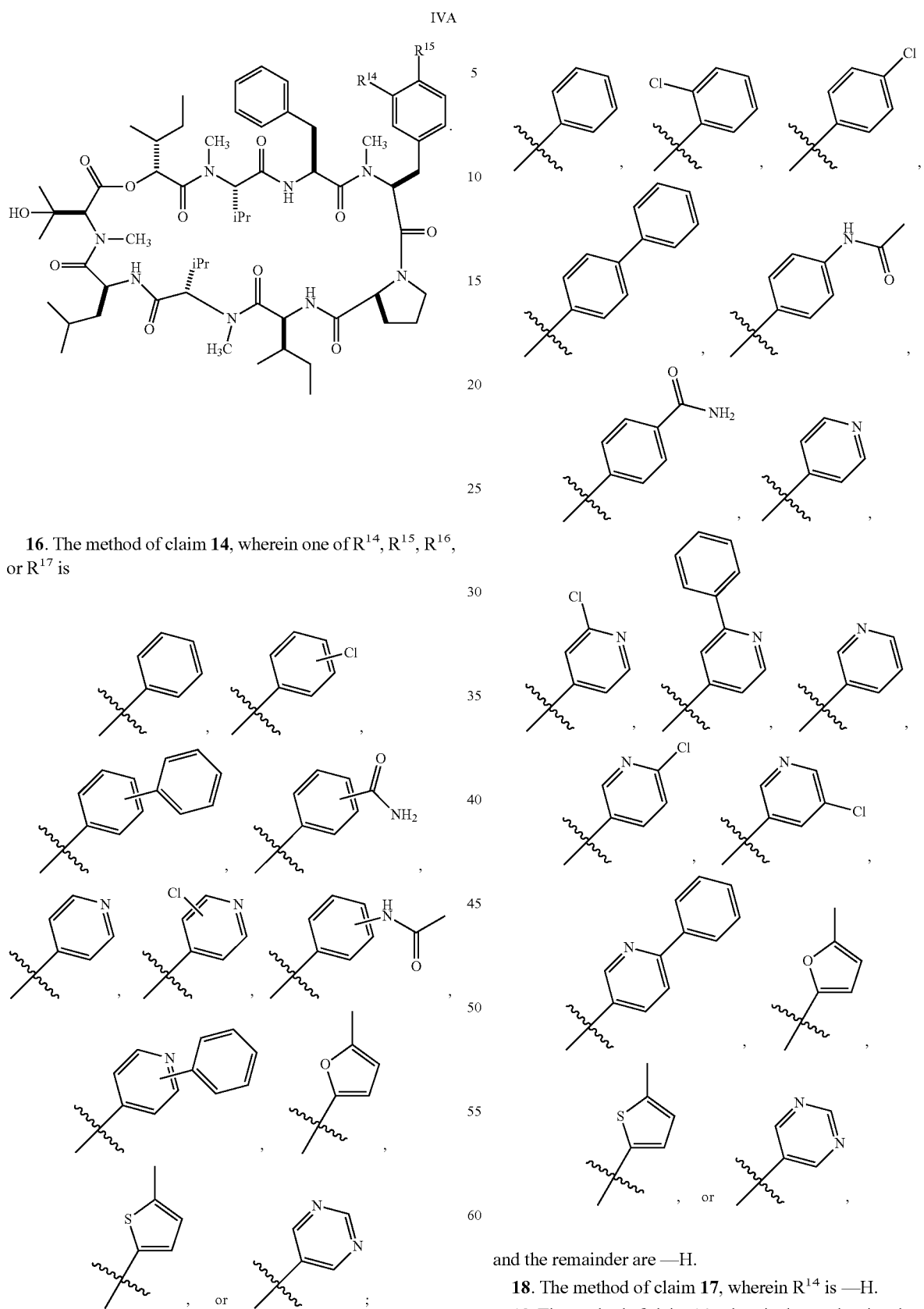
16. The method of claim 14, wherein one of $R^{14}$, $R^{15}$, $R^{16}$, or $R^{17}$ is
and the remainder are —H.
17. The method of claim 14, wherein one of $R^{14}$ or $R^{15}$ is
and the remainder are —H.
18. The method of claim 17, wherein $R^{14}$ is —H.
19. The method of claim 14, wherein the catalyst is selected from Pd(PPh$_3$)$_4$, Pd$_2$(dba)$_3$, PdCl$_2$(dppf), or any combination thereof.

20. A compound selected from

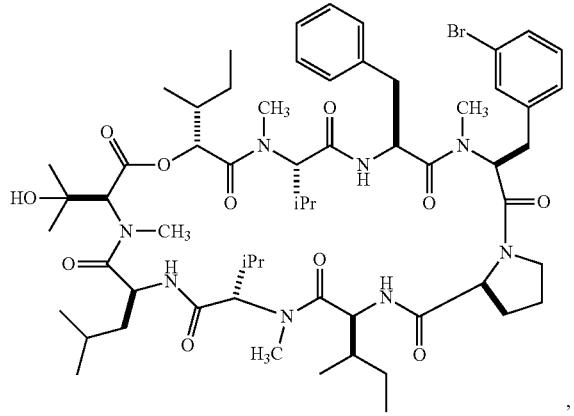

,

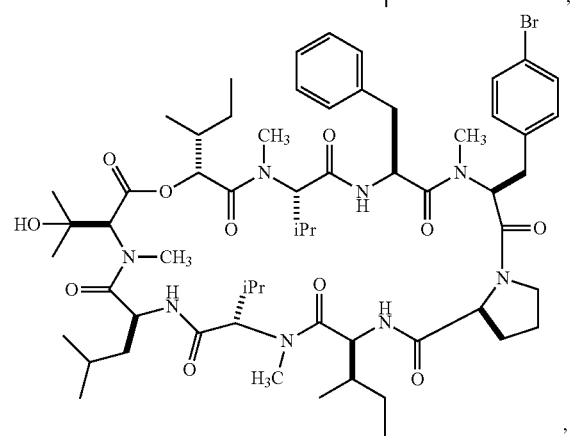

,

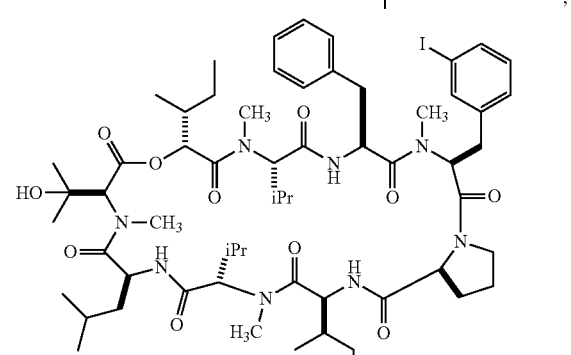

, or

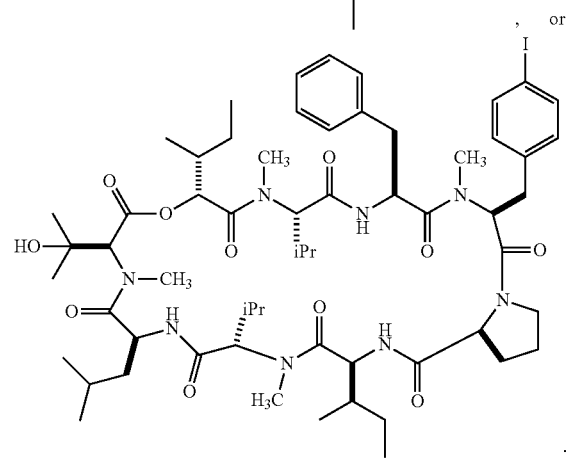

.

21. A compound of Formula Va

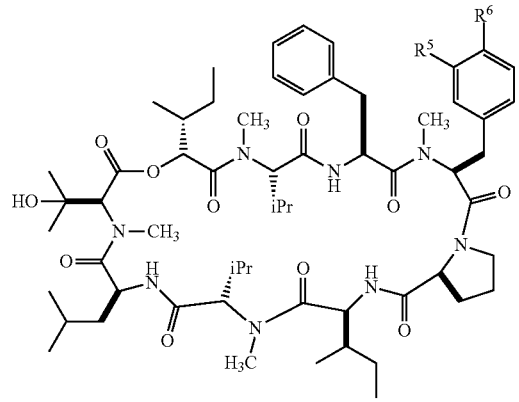

or a pharmaceutically acceptable salt thereof, wherein one of $R^5$ or $R^6$ is

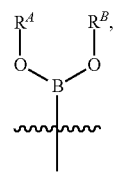

and the remainder is —H; and each of $R^A$ and $R^B$ are independently —$C_{1-4}$ alkyl, —$C_{1-4}$ cycloalkyl; or $R^A$ and $R^B$ together with the oxygen atoms to which they are attached form a 5-6 membered ring optionally substituted with 1-4 of —$C_{1-3}$ alkyl, —$C_{1-3}$ alkoxycarbonyl, —$C_{1-3}$ alkylaminocarbonyl, or any combination thereof; or $R^A$ and $R^B$ together with the oxygen atoms to which they are attached form a 7-10 membered bicyclic or tricyclic ring optionally substituted with 1-4 of —$C_{1-3}$ alkyl, —$C_{1-3}$ alkoxycarbonyl, —$C_{1-3}$ alkylaminocarbonyl, or any combination thereof.

22. The compound of claim 21, wherein the

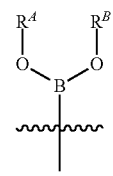

group is selected from

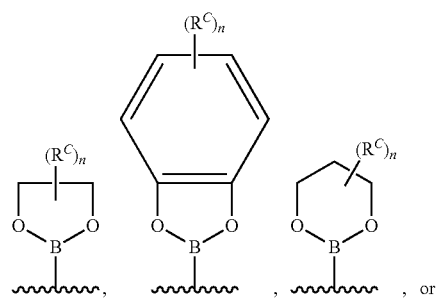

, or

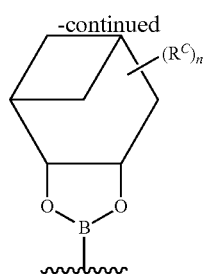

wherein each $R^C$ is independently selected from —H, —$C_{1-3}$ alkyl, —$C_{1-3}$ alkoxycarbonyl, —$C_{1-3}$ alkylaminocarbonyl, or any combination thereof, and n is 1-4.

23. A compound selected from

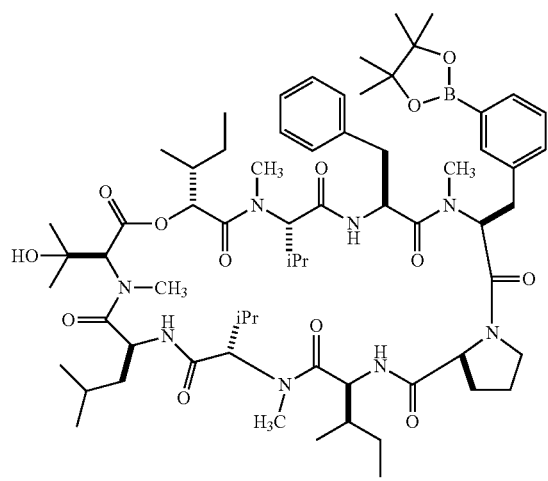

or

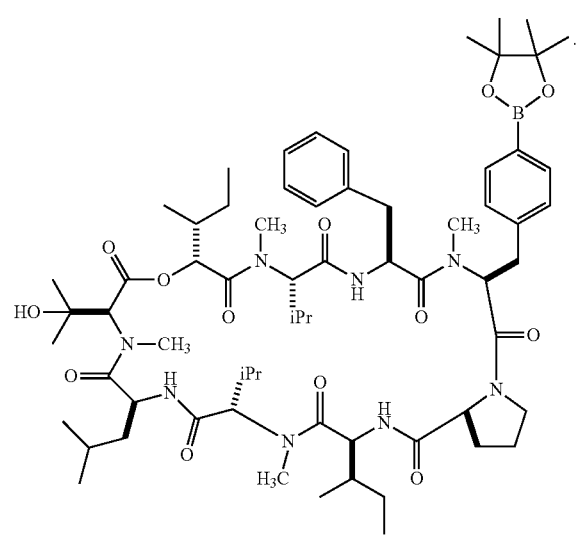

24. A compound of Formula II

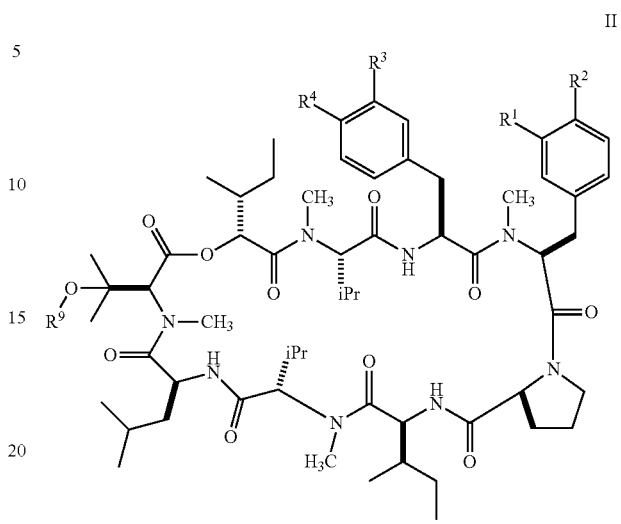

wherein
one of $R^1$, $R^2$, $R^3$, or $R^4$ is —X, and the remainder are —H, wherein X is a halogen, and $R^9$ is —Si($R^{10}$)$_3$, wherein each $R^{10}$ is independently selected from an unsubstituted linear or branched $C_{1-6}$ alkyl.

25. A compound of Formula III

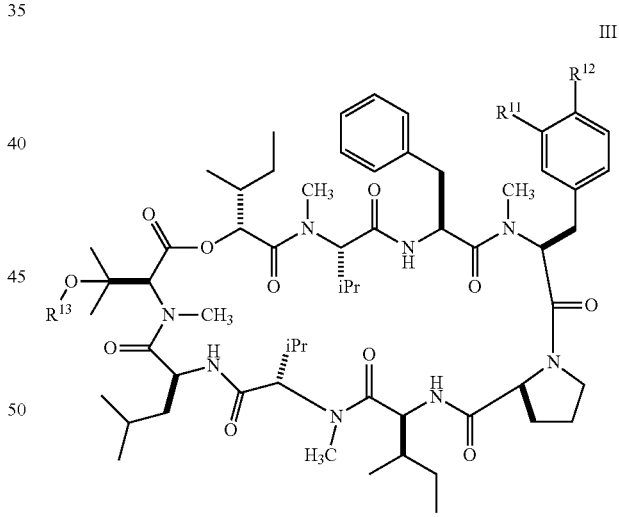

wherein
one of $R^{11}$ and $R^{12}$ is —H, and the remainder is —I, —Cl, —B(OH)$_2$,

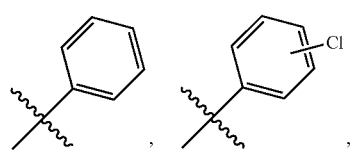

-continued

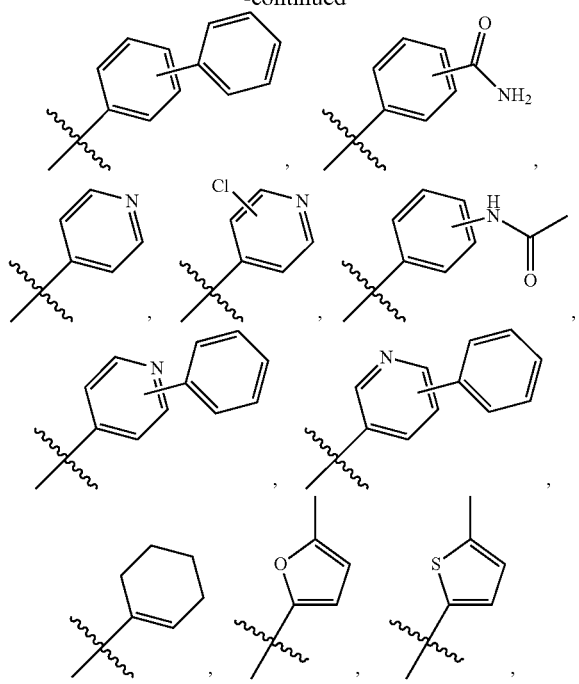

-continued

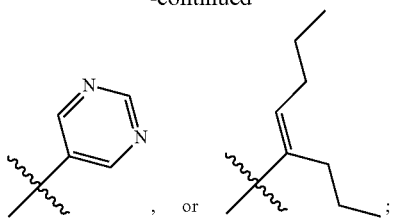

and $R^{13}$ is —H or —Si($R^{10}$)$_3$, wherein each $R^{10}$ is independently selected from an unsubstituted linear or branched $C_{1-4}$ alkyl.

26. The compound of claim 25, wherein $R^{13}$ is —H.

27. The compound of claim 25, wherein $R^{12}$ is —H.

28. A pharmaceutical composition comprising a compound of claim 25 and a pharmaceutically acceptable carrier, vehicle, or adjuvant.

29. A method of inhibiting IPC synthase in a biological sample comprising contacting said sample with a compound according to claim 25.

30. A method of treating a fungal infection in a patient, comprising administering to a patient in need thereof a compound according to claim 25.

* * * * *